(12) United States Patent
Spellberg et al.

(10) Patent No.: US 11,957,750 B2
(45) Date of Patent: Apr. 16, 2024

(54) TRIPLE VACCINE PROTECTS AGAINST BACTERIAL AND FUNGAL PATHOGENS VIA TRAINED IMMUNITY

(71) Applicant: University of Southern California, Los Angeles, CA (US)

(72) Inventors: Brad Spellberg, Los Angeles, CA (US); Travis Nielsen, Los Angeles, CA (US); Brian Luna, Los Angeles, CA (US); Jun Yan, Los Angeles, CA (US)

(73) Assignee: UNIVERSITY OF SOUTHERN CALIFORNIA, Los Angeles, CA (US)

( * ) Notice: Subject to any disclaimer, the term of this patent is extended or adjusted under 35 U.S.C. 154(b) by 0 days.

(21) Appl. No.: 18/213,127

(22) Filed: Jun. 22, 2023

(65) Prior Publication Data
US 2023/0346925 A1    Nov. 2, 2023

Related U.S. Application Data

(63) Continuation of application No. PCT/US2023/011209, filed on Jan. 20, 2023.

(60) Provisional application No. 63/321,961, filed on Mar. 21, 2022.

(51) Int. Cl.
| | |
|---|---|
| *A61K 36/06* | (2006.01) |
| *A61K 39/00* | (2006.01) |
| *A61K 39/02* | (2006.01) |
| *A61K 39/085* | (2006.01) |
| *A61K 39/09* | (2006.01) |
| *A61K 39/104* | (2006.01) |
| *A61K 39/108* | (2006.01) |
| *A61K 39/39* | (2006.01) |
| *A61P 37/04* | (2006.01) |

(52) U.S. Cl.
CPC .............. *A61K 39/39* (2013.01); *A61K 36/06* (2013.01); *A61K 39/0002* (2013.01); *A61K 39/025* (2013.01); *A61K 39/0258* (2013.01); *A61K 39/0266* (2013.01); *A61K 39/085* (2013.01); *A61K 39/104* (2013.01); *A61P 37/04* (2018.01); *A61K 2039/545* (2013.01); *A61K 2039/55505* (2013.01); *A61K 2039/55572* (2013.01)

(58) Field of Classification Search
None
See application file for complete search history.

(56) References Cited

U.S. PATENT DOCUMENTS

| | | |
|---|---|---|
| 5,817,643 A | 10/1998 | Jamas et al. |
| 9,061,066 B2 | 6/2015 | Gorvel et al. |
| 9,694,070 B2 | 7/2017 | Gorden et al. |
| 11,672,857 B2 * | 6/2023 | Spellberg ............... A61K 39/39 424/9.2 |
| 2006/0068448 A1 | 3/2006 | Takesako et al. |
| 2006/0165700 A1 | 7/2006 | Ostroff et al. |
| 2010/0166751 A1 | 7/2010 | Ostroff et al. |
| 2014/0302076 A1 | 10/2014 | Middelberg et al. |
| 2016/0058859 A1 | 3/2016 | Garrido-Lestache et al. |
| 2017/0224811 A1 | 8/2017 | Van Haren et al. |
| 2017/0239349 A1 | 8/2017 | Agadjanyan et al. |
| 2019/0314471 A1 | 10/2019 | Scholler et al. |
| 2020/0353075 A1 | 11/2020 | Spellberg et al. |
| 2021/0000947 A1 | 1/2021 | Hargis et al. |
| 2021/0299250 A1 | 9/2021 | Levy et al. |
| 2022/0105167 A1 | 4/2022 | Desvaux et al. |
| 2023/0355751 A1 | 11/2023 | Spellberg et al. |

FOREIGN PATENT DOCUMENTS

WO    WO-2015/161218 A1    10/2015

OTHER PUBLICATIONS

Non-Final Office Action on U.S. Appl. No. 16/760,389 dated Sep. 21, 2022 (9 pages).
Notice of Allowance on U.S. Appl. No. 16/760,389 dated Feb. 15, 2023 (9 pages).
Toussi et al., "Immune Adjuvant Effect of Molecularly-defined Toll-Like Receptor Ligands", Vaccines, Apr. 25, 2014, vol. 2, No. 2, (pp. 323-353).
International Search Report and Written Opinion on International Patent Application No. PCT/US2023/011209 dated Mar. 27, 2023 (10 pages).

* cited by examiner

*Primary Examiner* — S. Devi
(74) *Attorney, Agent, or Firm* — Foley & Lardner LLP

(57) ABSTRACT

An optimized protein-free tripartite vaccine that protects against lethal blood and lung infections caused by a variety of nosocomial pathogens across taxonomic kingdoms, including Gram-positive bacteria, Gram-negative bacteria, and fungi.

15 Claims, 44 Drawing Sheets

|         | Median Binding (%) | |
|---------|-----------|--------------|
|         | _S. aureus_ | _A. baumannii_ |
| Isotype | 1% | 0% |
| Day 0 | 1% | 0% |
| Day -1 | 1% | 0% |
| Day -3 | 1% | 0% |
| Day -7 | 1% | 0% |
| Day -14 | 1% | 0% |
| Day -21 | 1% | 0% |
| Immune Serum | 57% | 94% |

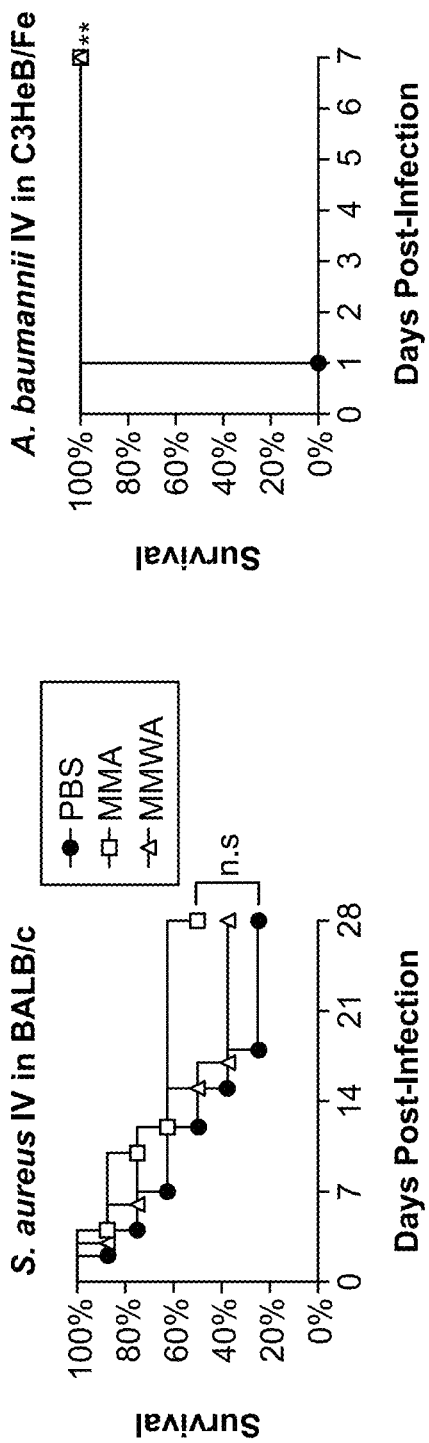
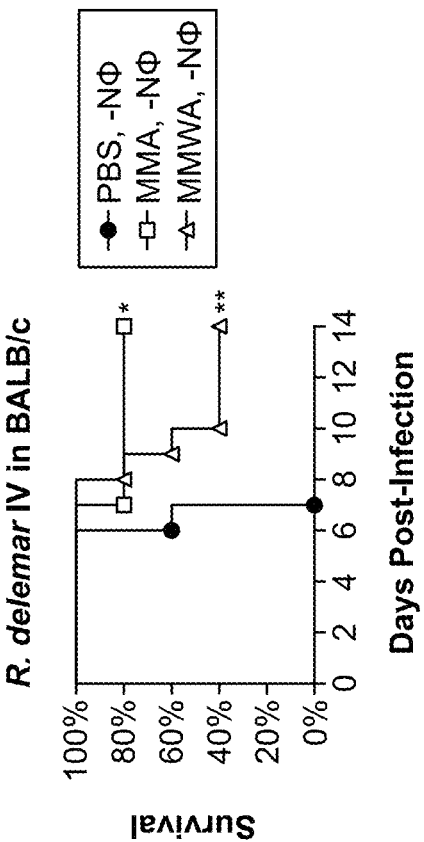
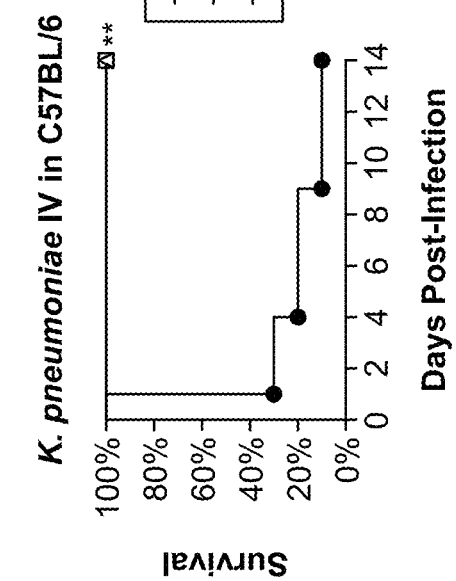
FIG. 17A
FIG. 17B
FIG. 17C
FIG. 17D

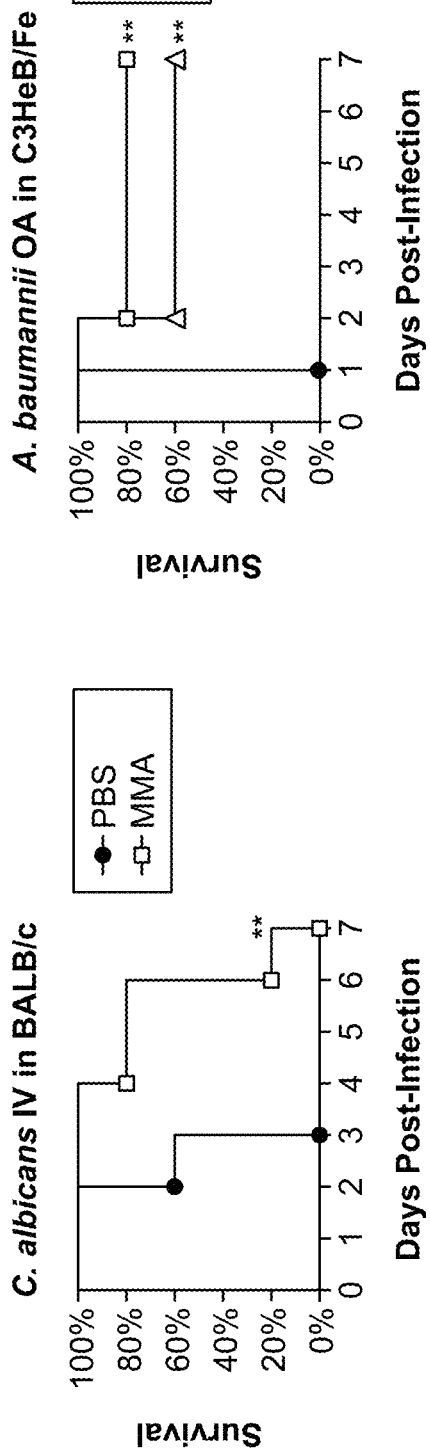
FIG. 17E
FIG. 17F
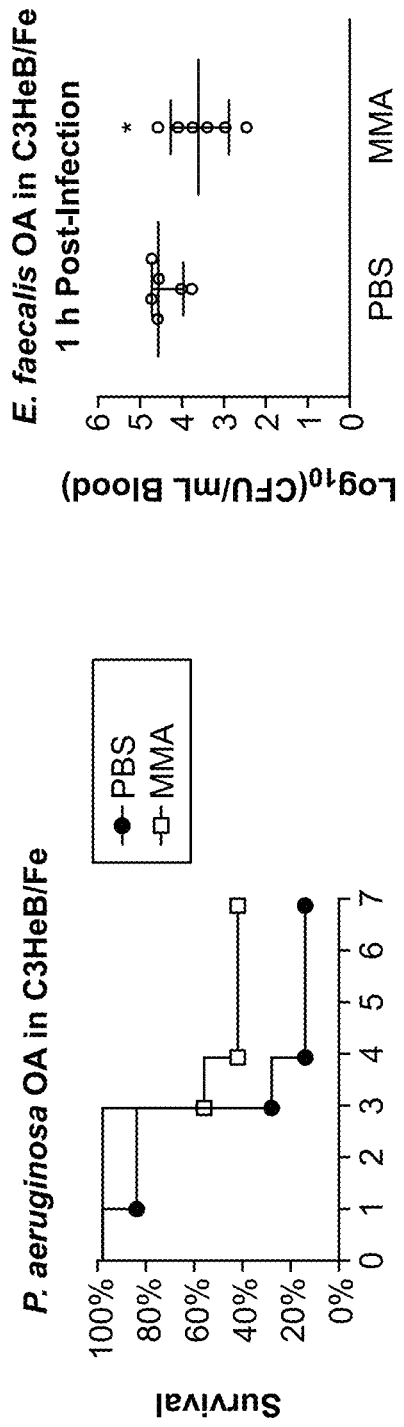
FIG. 17H
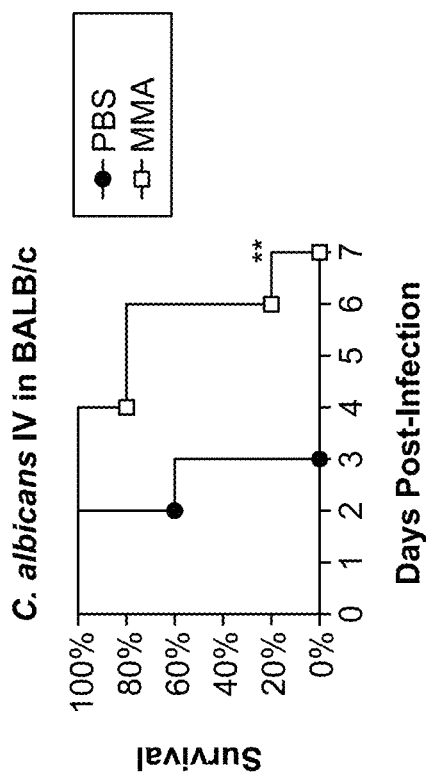
FIG. 17G

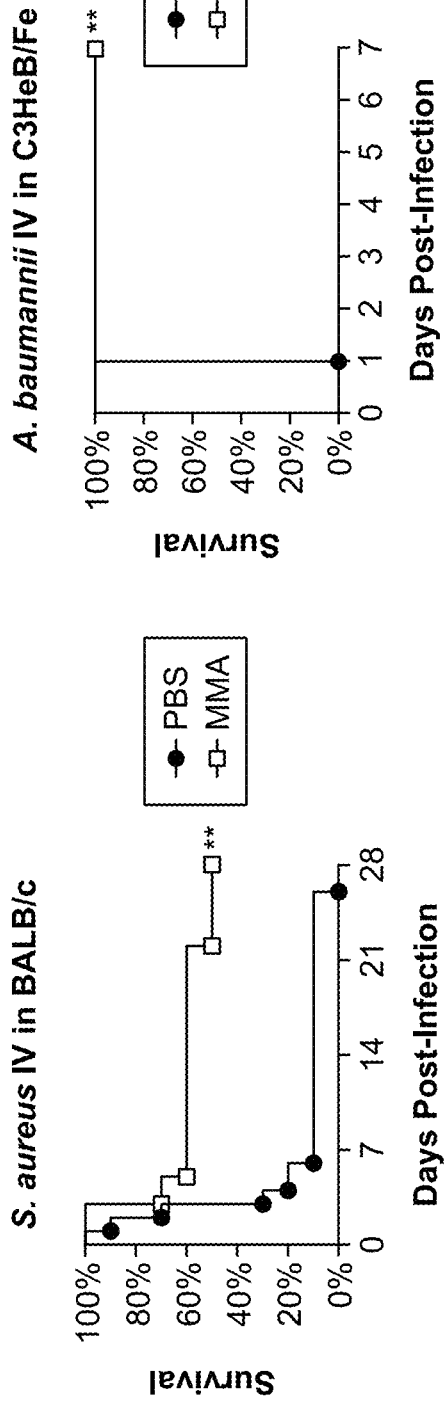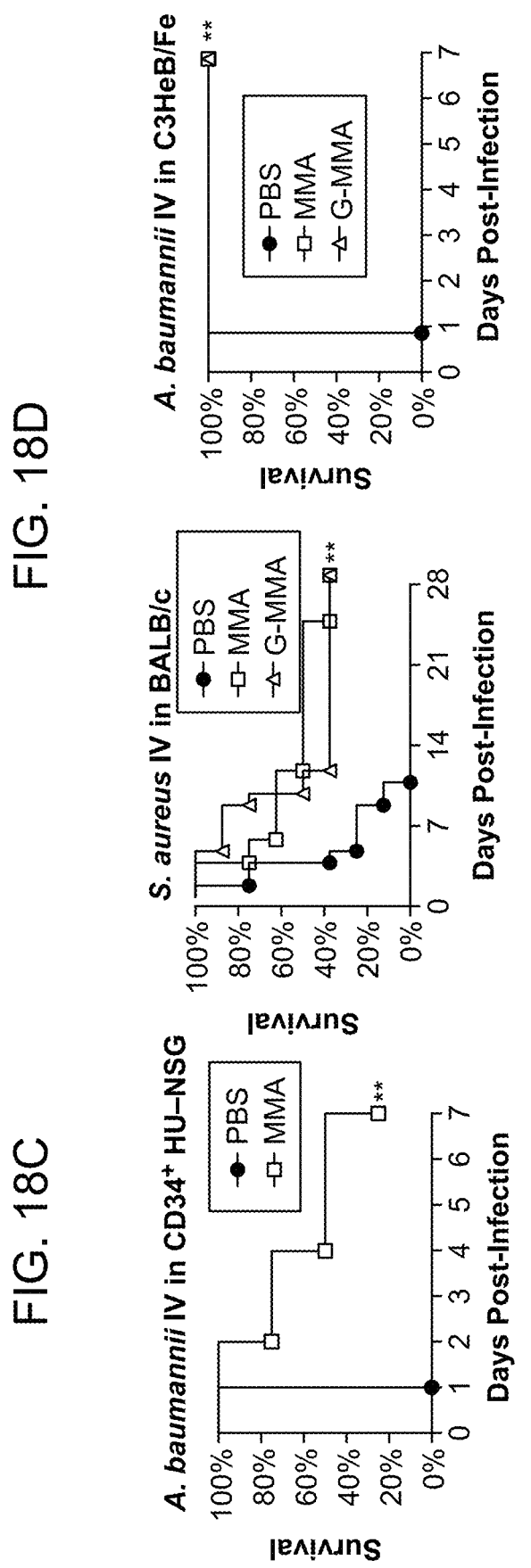

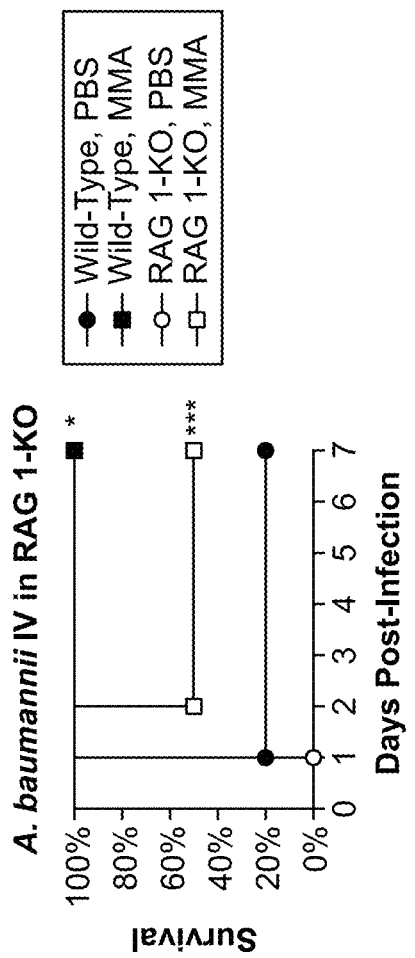
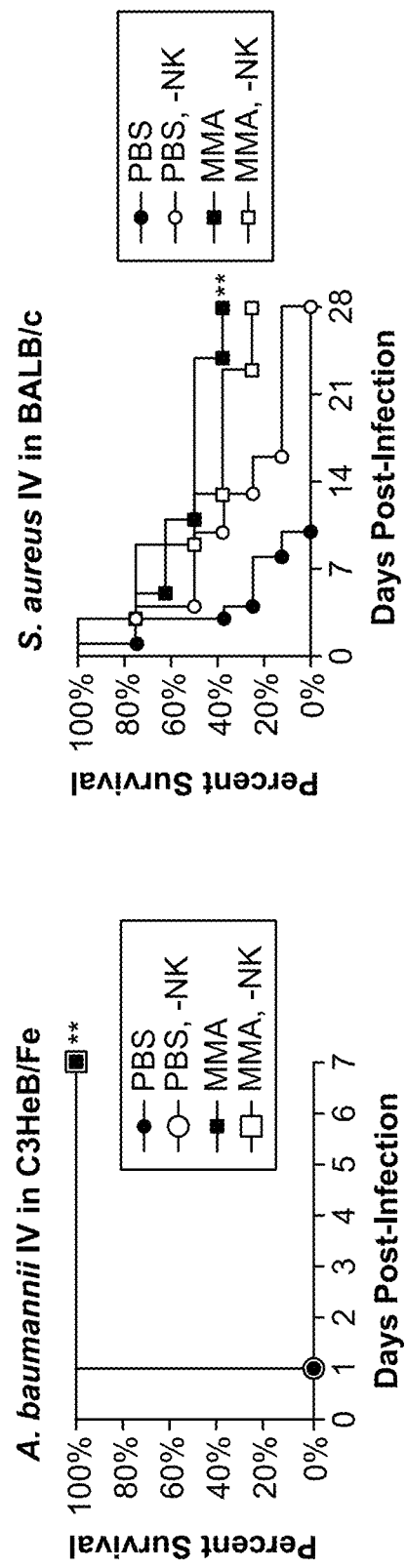
FIG. 20A
FIG. 20B
FIG. 20C

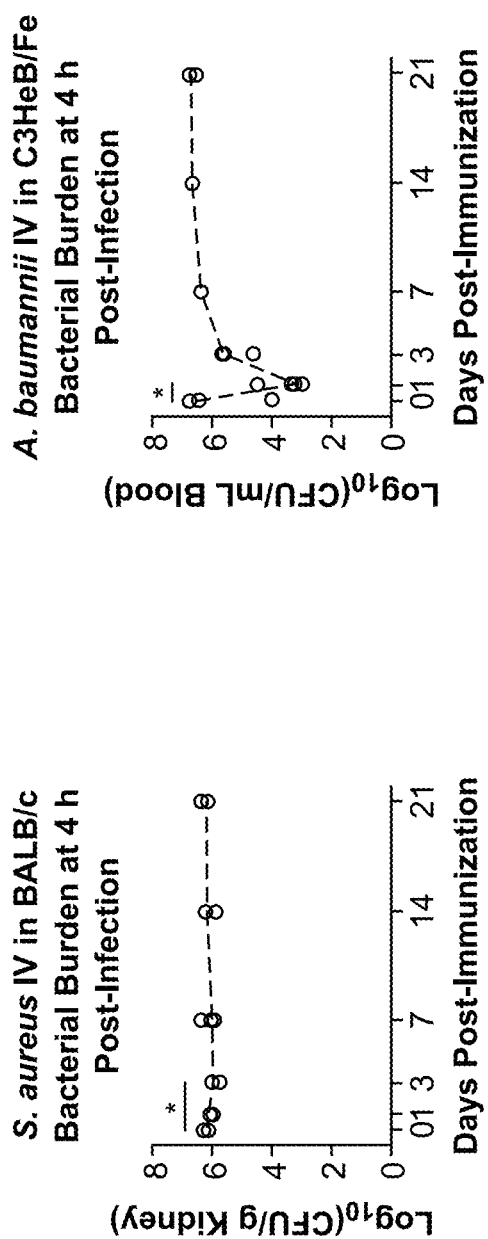
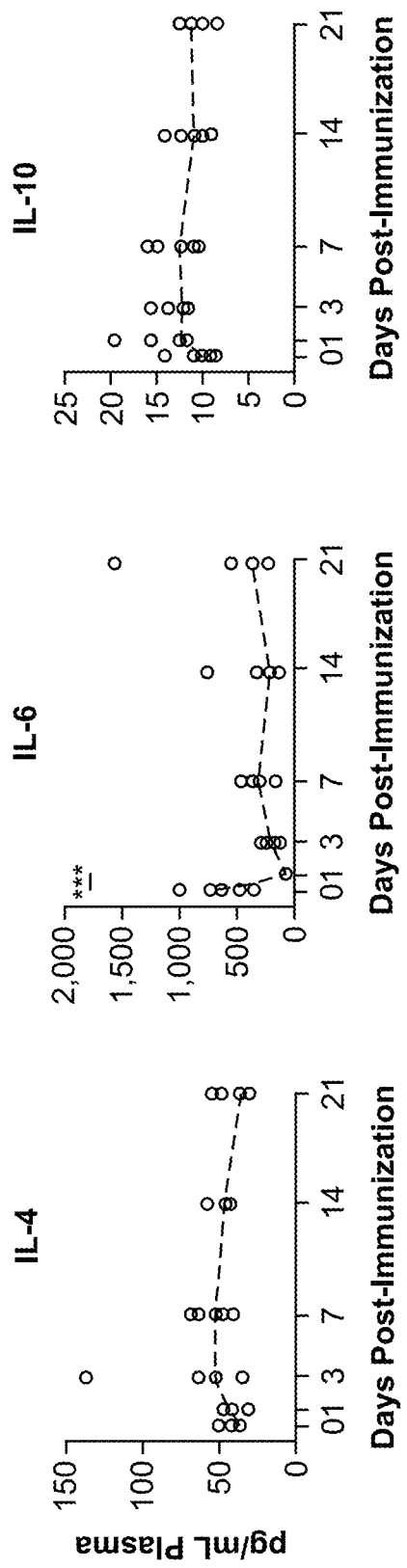
FIG. 22C
FIG. 22D
FIG. 22E

TRIPLE VACCINE PROTECTS AGAINST BACTERIAL AND FUNGAL PATHOGENS VIA TRAINED IMMUNITY

CROSS-REFERENCE TO RELATED APPLICATION

This application claims priority under 35 U.S.C. § 120 to PCT/US2023/011209, filed Jan. 20, 2023 which in turn claims priority under 35 U.S.C. § 119(e) to U.S. Provisional Application No. 63/321,961, filed Mar. 21, 2022, the contents of each of which are incorporated herein by reference in their entireties.

STATEMENT OF GOVERNMENT SUPPORT

This invention was made with government support under Grant Nos. AI145759, AI130060, AI106375, and AI139052, awarded by the National Institutes of Health (NIH). The government has certain rights in the invention.

BACKGROUND

Throughout this application, several technical publications are referenced by an Arabic numeral. The complete bibliographic citation for each reference is found immediately preceding the claims. The contents of each publication so referenced, and the publications referenced within the specification are hereby incorporated into the present disclosure to more fully describe the state of the art to which this invention pertains.

Approximately 7% of inpatients will develop a healthcare-associated infection (HAI), approximately half of which are comprised of pneumonia, bloodstream infection, or wound infections, which are likely the most amenable to immunological intervention (W. H. Organization). On any given day, approximately 3% of hospital inpatients have an HAI (S. S. Magill et al., N Engl J Med 370, 2014). At acute-care hospitals in the US, this results in 722,000 HAIs, more than 75,000 deaths, and a financial burden exceeding $100 billion, every year (A. Marchetti et al., J Med Econ 16, 2013). In most cases, HAIs are caused by antimicrobial-resistant bacterial and fungal pathogens, which are associated with worse mortality and morbidity than antimicrobial-susceptible pathogens (L. M Weiner et al., Infect Control Hosp Epidemiol 37, 2016). Despite the high incidence of HAIs, there are no FDA-approved vaccines against the most commonly encountered and antibiotic-resistant pathogens, like methicillin-resistant *Staphylococcus aureus* (MRSA), carbapenem-resistant *Acinetobacter baumannii* (CRAB), and carbapenem-resistant Enterobacterales (CRE).

Broadly speaking, there are two approaches to preventing infections: horizontal and vertical (R. P. Wenzel et al., Int J Infect Dis 14 Suppl 4, 2010). Horizontal approaches protect against a wide range of pathogens; examples include disinfecting hospital rooms with ultraviolet light or bleach, hand washing, and personal protective equipment (PPE). Horizontal approaches provide protection against a broad spectrum of infectious organisms and offer the best overall value, although the implementation and maintenance of these approaches are generally challenging. By comparison, vertical approaches provide specific protection against only one organism. Vertical approaches are thus much narrower in focus; examples include active surveillance and testing of specific pathogenic species, decolonizing hospitalized patients with MRSA, and vaccinating against certain pathogens (e.g., pneumococcus, influenza). While offering a powerful way to prevent infections through long-term adaptive immunity, traditional vaccines only protect against one specific pathogen. Moreover, the development of vaccines is costly, time-consuming, and scientifically challenging. Although the merits of both approaches are often debated, horizontal approaches have been shown to have a broader impact at lower costs (E. Septimus et al., Infect Control Hosp Epidemiol 35, 2014). Nevertheless, a strategy that seeks to integrate both approaches will be most successful in preventing a greater disease burden than either approach alone.

SUMMARY OF THE DISCLOSURE

This disclosure provides an entirely new vaccine-derived approach, based on adjuvants without a protein or polypeptide antigen, to mediate broad spectrum short-to-intermediate term protection against deadly, HAIs caused by bacteria (including antibiotic-resistant bacteria) and fungi. This approached is based on entirely new horizontal rather than vertical infection prevention strategy. In one aspect, the vaccine or composition does not contain, comprise, consist essentially of, or consist of a substance such as a protein or polypeptide that induces or raises lymphocyte-mediated (T cell or B cell) adaptive immunity. In several embodiments, the antigen can be a protein or polypeptide derived from a virus, fungus or bacteria, that can induce or raise a T cell and/or B cell adaptive immunity.

"Horizontal" infection prevention strategy intends an approach that prevent infections caused by many different pathogens at once, which are preferred to approaches that prevent infections one pathogen at a time (7). This disclosure utilizes a horizontal infection prevention strategy by immunizing with broadly-active adjuvants to provide innate immune protection against the Gram-positive and Gram-negative bacterial pathogens and fungal pathogens.

The results show that the combination comprising, consisting essentially of, or consisting of an effective amount of each of: mannan, a mono-phosphoryl lipid (MPL), and an aluminum hydroxide (in combination referred to herein as "MMA or MMMA") induced protection and is linked to epigenetic changes in macrophages. Depletion of macrophages, but not B and T lymphocytes, prevented MMA from protecting against infection. Without being bound by theory, this suggests MMA induced protection is likely induced by macrophage immune memory, and not lymphocyte-mediated adaptive immunity. Without being bound by theory, Applicant demonstrated immunomodulation by macrophages is the key contributing reason MMA improved survival during lethal infections of a variety of pathogens from across taxonomic kingdoms, including Gram-positive bacteria, Gram-negative bacteria, and fungi.

Thus, in one aspect, provided herein is a composition comprising, or consisting essentially of, or yet further consisting of an effective amount of each of: MPL mono-phosphoryl lipid (MPL), mannan, and aluminum hydroxide ("MMA"), with the proviso that the composition does not comprise an antigen effective to induce a B-cell or T-cell memory immune response against any pathogen, e.g., a viral, a fungal or a bacterial pathogen. In another aspect, provided herein is a composition consisting essentially of an effective amount of each of: MPL mono-phosphoryl lipid (MPL), mannan, and aluminum hydroxide (collectively "MMA"), with the proviso that the composition does not comprise an antigen effective to induce an immune response against any pathogen, e.g., a viral, a fungal or a bacterial pathogen. Yet further provided is a composition consisting of as active immune inducing agents, an effective amount of each of: MPL mono-phosphoryl lipid (MPL), mannan, and aluminum hydroxide (collectively "MMA"). In a yet further aspect, the effective amount of the aluminum hydroxide, MPL mono-phosphoryl lipid (MPL), and mannan in combination, is effective to induce an immune response when administered to a subject in need thereof, wherein in one embodiment, the immune response is neither a T cell nor B cell adaptive immunity Applicant unexpectedly found that the triple combination "MMA" resulted in superior protection against *S. aureus* than a combination of triple adjuvants comprised of aluminum hydroxide, MPL, and whole glucan particles, and that the triple combination of MMA was more effective than even a quadruple regimen including aluminum hydroxide, MPL, whole glucan particle, and mannan against *A. baumannii* blood and lung infection and against mucormycosis. Thus, the unique triple combination "MMA" is superior to protect against Gram positive, Gram negative, and fungal infections than a triple combination in which whole glucan particles are used in lieu of mannan, or even a quadruple combination including both whole glucan particles and mannan.

For the purpose of this disclosure, the aluminum hydroxide is $Al(OH)_3$ typically found in nature as the mineral Gibbsite. It is commercially available and can be an aluminum hydroxide gel or wet suspension, optionally commercially available Alhydrogel® (Sigma-Aldrich) or $Al(OH)_3$ gel (Accurate Chemical & Scientific Corporation Cat. #A1090S or $Al(OH)_3$ gel, Croda Cat. #AJV3012). The percentage of $Al(OH)_3$ in the source material can be any percentage, non-limiting examples of such include a 2% or 1% composition and combinations thereof.

In one embodiment the components of the MMA are combined in total volumes of 0.5 to 1 ml liquid suspension, containing 0.2 to 1 mg of aluminum hydroxide; from about 0.01 to 1.5 mg of MPL; and from about 0.1 to 5 mg of mannan.

As is apparent to the skilled artisan, the compositions can be combined with a pharmaceutically acceptable carrier, such as phosphate buffered saline (PBS) and DMSO, for ease of storage and for administration. The compositions can further contain stabilizers and components for example, maintaining stability during storage or lyophilization.

This disclosure also provides a method to enhance immunity in a subject against an infection caused by a pathogen, e.g., a bacterial or fungal pathogen, by a method comprising, or consisting essentially of, or yet further consisting of administering to the subject an effective amount of a composition (e.g., MMA) as described herein. This disclosure also provides compositions or medicaments for use to enhance immunity in a subject against an infection caused by a pathogen, e.g., bacterial or fungal pathogen, the medicament comprising, or consisting essentially of, or yet further consisting of a composition (e.g., MMA) as described herein. To enhance immunity intends a result of protection from disease or symptoms and can be monitored clinically (e.g., fever, cough or pain) or sub-clinically (enhanced innate immunity as measure by, for example, the presence or increased presence of macrophages and/or monocytes, lowered bacterial or fungal burden, lower proinflammatory cytokines, e.g., (IL-6, IL-12, TNF) and elevated IL-10/TNF).

Further provided are methods to treat or prevent a bacterial or fungal infection or a disorder caused by a bacterial or fungal infection in a subject in need thereof, the methods comprising, or alternatively consisting essentially of, or yet further consisting of, administering an effective amount of the composition (e.g., MMA) of this disclosure. Also provided are compositions for use or medicaments as described herein to treat or prevent a bacterial or fungal infection or a disorder caused by a bacterial or fungal infection in a subject in need thereof.

Non-limiting examples of bacterium are selected from *S. aureus, A. baumannii*, K *Pneumoniae, P. aeruginosa, E. coli, Enterobacter* spp., *Serratia, Stenotrophomonas*, and the fungus can be *Candida* spp or species that cause the disease mucormycosis (e.g., *Rhizopus* spp).

Any appropriate method of administration can be used. Non-limiting examples include a method comprising topical, inhalation, intramuscular, subcutaneous, or intravenous administration as determined by the treating physician. The composition can be administered once, twice, or three times over the period of one to three months or more.

In one aspect, the subject is infected with the bacterial or fungal microorganism. Alternatively the subject is at risk of the bacterial or fungal infection.

The therapeutic methods, uses and medicaments can be further combined with appropriate diagnostics to assaying the subject for a bacterial or fungal infection prior to, during, and/or administration of the composition.

Subjects to be treated include mammals, e.g., rats, mice, canines, felines, humans and the like. When practiced in non-human animal, the method provides an appropriate animal model for testing against new disease pathogens or combination therapies. When practiced in a human subject, the method is a viable therapeutic modality.

Further provided are kits comprising the composition of as described herein and instructions for use.

Yet further provided are method to identify an compound or agent that provides a benefit selected from one or more of: enhances immunity against a bacterial or fungal microbial infection or treats a bacterial or fungal infection or a disease related to a bacterial or fungal microbial infection, the method comprising admixing the compound or agent with the composition as disclosed herein and administering the admixed composition to a non human subject infected with a bacterial or fungal microorganism and assaying for post-administration infection or survival, wherein the compound or agent that enhances the activity of the composition of this disclosure. Methods determine if a benefit is provided are known in the art and briefly described herein.

BRIEF DESCRIPTION OF THE DRAWINGS

(FIG. 1A) Female BALB/c mice (N=8 per group) were immunized subcutaneously (SC) and boosted three weeks later with 10 μg monophosphoryl lipid A (MPL), 100 μg whole glucan particles (WGP), 200 μg of $Al(OH)_3$, 0.826 μg LPS, and/or recombinant protein antigens (Ag). Three weeks after the boost, mice were infected intravenously (IV) via the tail vein with $4.5 \times 10^7$ CFU *S. aureus* LAC. (FIG. 1B) Female BALB/c mice (N=8 per group) were immunized SC with 10 μg MPL, 100 μg WGP, and 200 μg $Al(OH)_3$; half of mice were boosted three weeks after the initial immunization. Three, seven, or 21 days after the final immunization, mice were infected IV via the tail vein with $4.9 \times 10^7$ CFU *S. aureus* LAC. (FIG. 1C) Male C3HeB/Fe mice (N=6 per group) were immunized SC with 10 μg MPL, 100 μg WGP, and 200 μg $Al(OH)_3$. Three or seven days after the immunization, mice were infected IV via the tail vein with $1.74 \times 10^7$ CFU *A. baumannii* HUMC 1. (FIG. 1D) Male C3HeB/Fe mice (N=6 per group) were immunized SC with zero, one, two, or all three adjuvants at 10 μg MPL, 100 μg WGP, and 0.2 mg Al(OH)$_3$. Three days later, mice were infected IV via the tail vein with $2.5 \times 10^7$ CFU *A. baumannii* HUMC 1. (FIG. 1E) Male C3HeB/Fe mice (N=8 per group) were immunized SC with 10 μg MPL, 100 μg WGP, and 0.2 mg Al(OH)$_3$. Three days after the immunization, mice were infected via oral aspiration (OA) with $1.5 \times 10^8$ CFU *A. baumannii* HUMC 1. (FIG. 1F) Male C3HeB/Fe mice (N=6 per group) were immunized SC with 10 μg MPL, 100 μg WGP, and 0.2 mg Al(OH)$_3$. Three or seven days after the immunization, mice were infected IV via the tail vein with $3.8 \times 10^8$ CFU *K. pneumoniae* KP3. (FIG. 1G) Female BALB/c mice (N=10 per group) were immunized SC with phosphate-buffered saline (PBS), MWA (10 μg MPL, 100 μg WGP, and 0.2 mg Al(OH)$_3$), MWA 10% (1 μg MPL, 10 μg WGP, and 0.2 mg Al(OH)$_3$), or MWA 1% (0.1 μg MPL, 1 μg WGP, and 0.2 mg Al(OH)$_3$). Three days after the immunization, mice were infected IV via the tail vein with $8.4 \times 10^7$ CFU *S. aureus* LAC. (FIG. 1H) Male C3HeB/Fe mice (N=5 per group) were immunized SC with PBS, MWA (10 μg MPL, 100 μg WGP, and 0.2 mg Al(OH)$_3$), MWA 10% (1 μg MPL, 10 μg WGP, and 0.2 mg Al(OH)$_3$), or MWA 30% (3 μg MPL, 30 μg WGP, and 0.2 mg Al(OH)$_3$). Three days after the immunization, mice were infected IV via the tail vein with $4.6 \times 10^7$ CFU *A. baumannii* HUMC1. Survival was compared by the non-parametric Log-Rank test with $\alpha=0.05$. *$p \leq 0.05$, $p \leq 0.01$, *$p \leq 0.001$ vs PBS group.

(FIG. 3C) Male C3HeB/Fe and female BALB/c mice (N=5 per group) immunized with MMA did not develop antibodies specific to *S. aureus* or *A. baumannii*. (FIG. 3D) Female BALB/c mice (N=10 per group) were infected IV via the tail vein with $1.2 \times 10^8$ CFU *S. aureus* LAC and (FIG. 3E) male C3HeB/Fe mice (N=5 per group) were infected IV via the tail vein with $2.9 \times 10^7$ CFU *A. baumannii* HUMC1 24-h post-immunization. (FIG. 3F) Male C57BL/6 mice with humanized CD34$^+$ cells (N=4 per group) were infected IV via the tail vein with $1.4 \times 10^7$ CFU *A. baumannii* HUMC1 three days post MMA immunization. (FIG. 3G) Male C3HeB/Fe mice (N=5 per group) were infected IV via the tail vein with $2.4 \times 10^7$ CFU *A. baumannii* HUMC1 and (FIG. 3H) female BALB/c mice (N=8 per group) were infected IV via the tail vein with $3 \times 10^8$ CFU *S. aureus* LAC three days post research grade and GMP grade MMA immunization. Survival was compared by the non-parametric Log-Rank test with $\alpha=0.05$. *$p \leq 0.05$, **$p \leq 0.01$ vs PBS group.

(FIG. 5A) Male C57BL/6J wild-type (WT) mice (N=5 per group) and RAG1 knockout (RAG1-KO) mice (N=6 per group) were immunized SC with a 0.2 ml suspension in PBS containing MMA (100 μg Mannan, 10 μg MPL, and 0.2 mg Al(OH)$_3$) and infected IV via the tail vein with $3.9$-$7.8 \times 10^7$ CFU *A. baumannii* HUMC1. (FIGS. 5B-5G) Male C3HeB/Fe mice (N=5 per group) and female BALB/c mice (N=8 per group) were depleted of neutrophils with cyclophosphamide, macrophages and monocytes with liposomal clodronate, or natural killer (NK) cells with anti-Asialo-GM1 antibody. Mice were then immunized with MMA (100 μg Mannan, 10 μg MPL, and 0.2 mg Al(OH)$_3$) and infected IV via the tail vein with *A. baumannii* HUMC 1 or *S. aureus* LAC. MMA stimulated (FIG. 5F) Primary human macrophage.

(FIG. 6A) Female BALB/c mice (N=5 per group) were infected IV via the tail vein with $1.5 \times 10^8$ CFU *S. aureus* LAC. Kidney bacterial burden was assessed 4 h post-infection. (FIG. 6B) Male C3HeB/Fe mice (N=5 per group) were infected IV via the tail vein with $1.8 \times 10^7$ CFU *A. baumannii* HUMC 1. Blood bacterial burden was assessed 4 h post-infection. (FIGS. 6C-6D) Plasma from each mouse was then analyzed by Luminex for five cytokines: IL-4, IL-6, IL-10, IL-12 p70, and TNF.

(FIG. 12A) Quadruple vaccine (MMA+WGP) protected mice. (FIG. 12B) MMA triple vaccine alone was more effective than quadruple vaccine (MMA+WGP) with higher inoculum. A modified triple in which WGP replaced MPL (containing 100 µg WGP+100 µg Mannan+200 µg aluminum hydroxide) was not effective, underscoring non-obviousness of the MMA triple combination. *p≤0.05 vs. PBS.

FIGS. 17A-17H Replacing whole glucan particles with mannan enhanced protection. Mice were immunized SC as a 0.2 ml suspension in PBS with MMA (100 µg Mannan, 10 µg MPL, and 0.2 mg Al(OH)$_3$), or MMWA (100 µg Mannan, 10 µg MPL, 100 µg WGP, and 0.2 mg Al(OH)$_3$). Three days later, (FIG. 17A) female BALB/c mice (N=8) were infected IV with 6.9×10$^7$ CFU MRSA LAC, (FIG. 17B) male C3HeB/Fe mice (N=5) were infected IV with 1.4-2.9×10$^7$ CFU XDR *A. baumannii* HUM1, (FIG. 17C) male C57BL/6 mice (N=5) were infected IV with 2.4×10$^8$ CFU carbapenem resistant *K pneumoniae* KPC-KP1, (FIG. 17D) female BALB/c mice (N=5) were infected IV with 3.0×10$^3$ CFU *R. delemar* 99-880, (FIG. 17E) male BALB/c mice (N=5) were infected IV with 1.7×10$^5$ *C. albicans*, (FIG. 17F) male C3HeB/Fe mice (N=5) were infected via OA with 1.6×10$^8$ CFU XDR *A. baumannii* HUMC1, (FIG. 17G) male C3HeB/Fe mice (N=3) were infected via OA with 5.7×10$^5$ CFU XDR *P. aeruginosa* PA9019, (FIG. 17H) Female C3HeB/Fe mice (N=6) were infected IV with 1.6-2.8×10$^8$ CFU VRE 51299 and blood bacterial burden was analyzed one hour post-infection. Survival was compared by the non-parametric log-rank test with α=0.05. Bacterial burdens were compared by the Wilcoxon rank-sum test for unpaired comparisons with α=0.05. *p≤0.05 and **p≤0.01 vs PBS.

FIGS. 18A-18G Larger doses help to extend the duration of protection. (FIG. 18A)-(FIG. 18B) Female BALB/c mice (N=8) and male C3HeB/Fe mice (N=5) were immunized SC with a 0.2 ml suspension of PBS containing MMA 1× (100 µg Mannan, 10 µg MPL, and 0.2 mg Al(OH)$_3$); MMA 3×(300 µg Mannan, 30 µg MPL, and 0.2 mg Al(OH)$_3$); or MMA 10×(1,000 µg Mannan, 100 µg MPL, and 0.2 mg Al(OH)$_3$). Seven, 14, or 21 days later, mice were infected IV with 9.7×10$^7$ CFU MRSA LAC and 2.9×10$^7$ CFU XDRA. *baumannii* HUMC1. (FIG. 18C)-(FIG. 18G) Female BALB/c mice (N=8-10), male C3HeB/Fe mice (N=5), and female NSG mice with adoptively transferred human CD34$^+$ hematopoietic stem cells (N=4) were immunized with PBS; research or GMP grade MMA (G-MMA) (100 µg Mannan, 10 µg MPL, and 0.1% Al(OH)$_3$). One or three days later, mice were infected IV with 1.2-3.0×10$^8$ CFU MRSA LAC and 1.4-2.9×10$^7$ CFU XDR *A. baumannii* HUMC1. Survival was compared by the non-parametric log-rank test with α=0.05. *p≤0.05 and **p≤0.01 vs PBS.

FIGS. 20A-20G Monocytes and macrophages are key effectors of MMA-mediated protection. (FIG. 20A) Male C57BL/6 wild-type mice (N=5) and RAG1-KO mice (N=6) were immunized SC with a 0.2 ml suspension of PBS containing MMA (100 μg Mannan, 10 μg MPL, and 0.2 mg Al(OH)$_3$) and infected IV with 3.9-7.8×10$^7$ CFU XDR *A. baumannii* HUMC1. (FIG. 20B)-(FIG. 20E) Male C3HeB/Fe mice (N=5) and female BALB/c mice (N=8) were depleted of natural killer (NK) cells or macrophages/monocytes. Mice were then immunized SC with a 0.2 ml suspension of PBS containing MMA (100 μg Mannan, 10 μg MPL, and 0.2 mg Al(OH)$_3$) and infected IV with 2.3-2.7×10$^7$ CFU XDR *A. baumannii* HUMC1 or 1.4-3.0×10$^8$ CFU MRSA LAC. (FIG. 20F) RAW 264.7 macrophages and (FIG. 20G) primary human monocytes were stimulated in vitro with MMA (5 μg/mL Mannan, 0.5 μg/mL MPL, 10 ng/mL Al(OH)$_3$) or IFNγ and evaluated for their ability to take up *A. baumannii* ATCC 17978. Survival was compared by the non-parametric log-rank test with α=0.05. Macrophage uptake was compared by the Wilcoxon rank-sum test for unpaired comparisons with α=0.05. *p≤0.05, p≤0.01, and *p≤0.001 respective to PBS.

(FIG. 21A) Summary of H3K27ac differential peaks between naïve, unvaccinated control mice, or samples taken at days 3 or 21 after vaccination of mice SC with 0.2 ml of a PBS suspension containing MMA (100 μg Mannan, 10 μg MPL, and 0.2 mg Al(OH)$_3$). Differential peaks were identified as adjusted p≤0.05, fold change >2, reads/peak >50. (FIG. 21B) Summary of transcriptional analysis by RNA-seq. Differentially expressed genes (DEGs) between three, 21 days immunized and naive control. DEGs were identified as those showing p≤0.05, FC >2 and RPKM >1. (FIG. 21C) Heatmaps of selected H3K27ac differential peaks and transcriptome DEGs analysis between three, 21 days immunized and naive control. Differential peaks and DEGs that were different between three days and naive control were selected. 3 mice per group. (FIG. 21D) Pathway analysis of H3K27ac differential peaks and DEGs using genes expressed higher in three days immunized compared to naive control.

FIGS. 22A-22F Decrease in pro-inflammatory cytokines in mice immunized with MMA. Mice were immunized SC with 0.2 ml of a PBS suspension containing MMA (100 μg Mannan, 10 μg MPL, and 0.2 mg Al(OH)$_3$) one, three, seven, 14 or 21 days before infection. (FIG. 22A)-(FIG. 22B) Gene expression changes of cytokine related genes (FIG. 22C)-(FIG. 22D) Female BALB/c mice (N=5 per group) and male C3HeB/Fe mice (N=5 per group) were infected IV via the tail vein with 1.5×10$^8$ CFU MRSA LAC and 1.8×10$^7$ CFU XDR *A. baumannii* HUMC1. Bacterial burden was assessed 4 h post-infection. (FIG. 22E)-(FIG. 22F) Plasma from each mouse was then analyzed by Luminex for cytokines: IL-4, IL-6, IL-10, IL-12 p70, and TNF. Kruskal-Wallis test with a =0.05. *p≤0.05, p≤0.01, *p≤0.001 vs naive mice (0 day post-immunization).

DETAILED DESCRIPTION

Figure 1A:
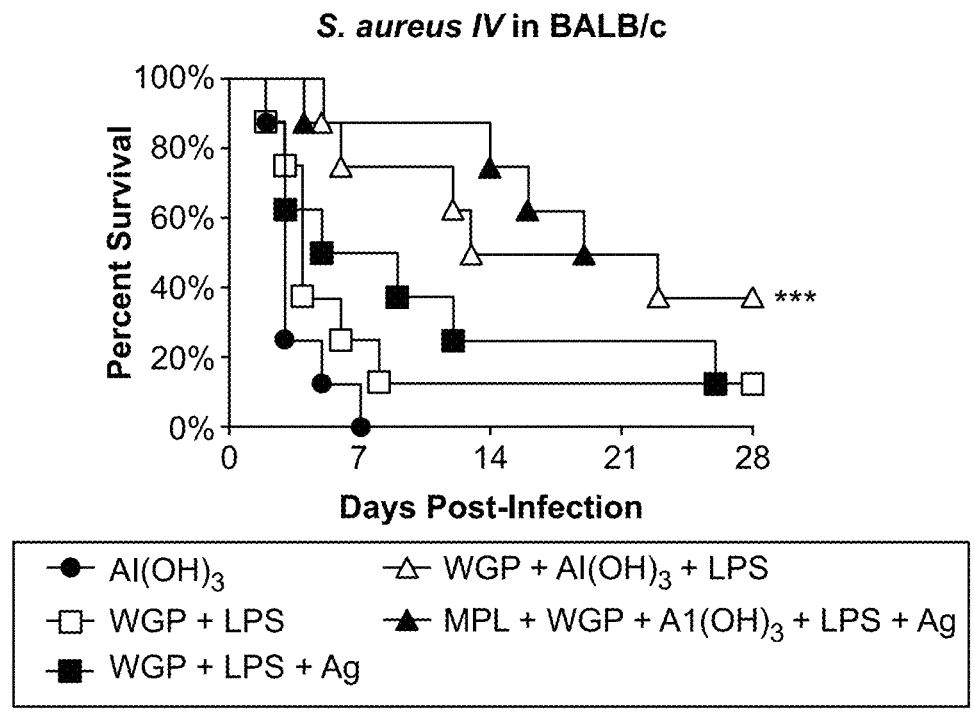
FIGS. 1A-1H show that Adjuvant-only vaccine provides short-term protection against lethal bloodstream infections in a dose-dependent manner. All vaccinations were administered as a 0.2 ml suspension in phosphate buffered saline (PBS).

Before the compositions and methods are described, it is to be understood that the invention is not limited to the particular methodologies, protocols, cell lines, assays, and reagents described, as these may vary. It is also to be understood that the terminology used herein is intended to describe particular embodiments of the present invention, and is in no way intended to limit the scope of the present invention as set forth in the appended claims.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All technical and patent publications cited herein are incorporated herein by reference in their entirety. Nothing herein is to be construed as an admission that the invention is not entitled to antedate such disclosure by virtue of prior invention.

The practice of the present invention will employ, unless otherwise indicated, conventional techniques of tissue culture, immunology, molecular biology, microbiology, cell biology and recombinant DNA, which are within the skill of the art. See, e.g., Sambrook and Russell eds. (2001) *Molecular Cloning: A Laboratory Manual*, 3rd edition; the series Ausubel et al. eds. (2007) *Current Protocols in Molecular Biology*; the series Methods in Enzymology (Academic Press, Inc., N.Y.); MacPherson et al. (1991) PCR 1: A Practical Approach (IRL Press at Oxford University Press); MacPherson et al. (1995) PCR 2: A Practical Approach; Harlow and Lane eds. (1999) Antibodies, *A Laboratory Manual*; Freshney (2005) *Culture of Animal Cells: A Manual of Basic Technique*, 5th edition; Gait ed. (1984) Oligonucleotid Synthesis; U.S. Pat. No. 4,683,195; Hames and Higgins eds. (1984) *Nucleic Acid Hybridization*; Anderson (1999) Nucleic Acid Hybridization; Hames and Higgins eds. (1984) Transcription and Translation; *Immobilized Cells and Enzymes* (IRL Press (1986)); Perbal (1984) *A Practical Guide to Molecular Cloning*; Miller and Calos eds. (1987) *Gene Transfer Vectors for Mammalian Cells* (Cold Spring Harbor Laboratory); Makrides ed. (2003) *Gene Transfer and Expression in Mammalian Cells*; and Mayer and Walker eds. (1987) Immunochemical Methods in Cell and Molecular Biology (Academic Press, London).

All numerical designations, e.g., pH, temperature, time, concentration, and molecular weight, including ranges, are approximations which are varied (+) or (−) by increments of 0.1. It is to be understood, although not always explicitly stated that all numerical designations are preceded by the term "about". It also is to be understood, although not always explicitly stated, that the reagents described herein are merely exemplary and that equivalents of such are known in the art.

All numerical designations, e.g., pH, temperature, time, concentration, and molecular weight, including ranges, are approximations which are varied (+) or (−) by increments of 0.1. It is to be understood, although not always explicitly stated that all numerical designations are preceded by the term "about". It also is to be understood, although not always explicitly stated, that the reagents described herein are merely exemplary and that equivalents of such are known in the art.

Definitions

As used in the specification and claims, the singular form "a", "an" and "the" include plural references unless the context clearly dictates otherwise. For example, the term "a cell" includes a plurality of cells, including mixtures thereof.

As used herein, the term "comprising" or "comprises" is intended to mean that the compositions and methods include the recited elements, but not excluding others. "Consisting essentially of" when used to define compositions and methods, shall mean excluding other elements of any essential significance to the combination for the stated purpose. Thus, a composition consisting essentially of the elements as defined herein would not exclude trace contaminants from the isolation and purification method and pharmaceutically acceptable carriers, such as phosphate buffered saline, preservatives and the like. "Consisting of" shall mean excluding more than trace elements of other ingredients and substantial method steps for administering the compositions of this invention or process steps to produce a composition or achieve an intended result. Embodiments defined by each of these transition terms are within the scope of this invention.

The term "isolated" as used herein with respect to nucleic acids, such as DNA or RNA, refers to molecules separated from other DNAs or RNAs, respectively that are present in the natural source of the macromolecule. The term "isolated peptide fragment" is meant to include peptide fragments which are not naturally occurring as fragments and would not be found in the natural state. The term "isolated" is also used herein to refer to polypeptides and proteins that are isolated from other cellular proteins and is meant to encompass both purified and recombinant polypeptides. In other embodiments, the term "isolated" means separated from constituents, cellular and otherwise, in which the cell, tissue, polynucleotide, peptide, polypeptide, protein, antibody or fragment(s) thereof, which are normally associated in nature. For example, an isolated cell is a cell that is separated form tissue or cells of dissimilar phenotype or genotype. As is apparent to those of skill in the art, a non-naturally occurring polynucleotide, peptide, polypeptide, protein, antibody or fragment(s) thereof, does not require "isolation" to distinguish it from its naturally occurring counterpart.

A "composition" is intended to mean a combination of the claimed elements and another compound or composition, inert (e.g. a detectable label) or active (with the exclusion of an antigen) alone or in combination with a carrier which can in one embodiment be a simple carrier like saline or pharmaceutically acceptable or a solid support as defined below.

A "pharmaceutical composition" is intended to include the combination of the claimed elements with a carrier, inert or active (with the exclusion of an antigen), making the composition suitable for diagnostic or therapeutic use in vitro, in vivo or ex vivo.

As used herein, the term "pharmaceutically acceptable carrier" encompasses any of the standard pharmaceutical carriers, such as a phosphate buffered saline solution, water, and emulsions, such as an oil/water or water/oil emulsion, DMSO, and various types of wetting agents. The compositions also can include stabilizers and preservatives. For examples of carriers, stabilizers and adjuvants, see Martin (1975) *Remington's Pharm. Sci.*, 15th Ed. (Mack Publ. Co., Easton).

"Administration" can be effected in one dose, continuously or intermittently throughout the course of treatment. Methods of determining the most effective means and dosage of administration are known to those of skill in the art and will vary with the composition used for therapy, the purpose of the therapy, the infection being treated, and the subject being treated. Single or multiple administrations can be carried out with the dose level and pattern being selected by the treating physician. Suitable dosage formulations and methods of administering the agents are known in the art. Route of administration can also be determined and method of determining the most effective route of administration are known to those of skill in the art and will vary with the composition used for treatment, the purpose of the treatment, the health condition or disease stage of the subject being treated, and the infecting bacteria or organism. Non-limiting examples of route of administration include oral administration, nasal administration, injection, and topical application.

The term "effective amount" refers to a quantity sufficient to achieve a desired effect. In the context of therapeutic or prophylactic applications, the effective amount will depend on the type and severity of the condition at issue and the characteristics of the individual subject, such as general health, age, sex, body weight, and tolerance to pharmaceutical compositions.

In the case of an in vitro application, in some embodiments the effective amount will depend on the size and nature of the application in question. It will also depend on the nature and sensitivity of the in vitro target and the methods in use. The skilled artisan will be able to determine the effective amount based on these and other considerations. The effective amount may comprise one or more administrations of a composition depending on the embodiment.

The routes of administration applicable to the methods of the invention include intravenous, intranasal, intramuscular, urethrally, intratracheal, subcutaneous, intradermal, topical application, rectal, nasal, oral, inhalation, and other enteral and parenteral routes of administration. Routes of administration may be combined, if desired, or adjusted depending upon the agent and/or the desired effect. An active agent can be administered in a single dose or in multiple doses. Embodiments of these methods and routes suitable for delivery, include systemic or localized routes.

Parenteral routes of administration other than inhalation administration include, but are not limited to, topical, transdermal, subcutaneous, intramuscular, intraorbital, intracapsular, intraspinal, intrasternal, and intravenous routes, i.e., any route of administration other than through the alimentary canal. Parenteral administration can be conducted to effect systemic or local delivery of the inhibiting agent. Where systemic delivery is desired, administration typically involves invasive or systemically absorbed topical or mucosal administration of pharmaceutical preparations.

The term "suffering" as it related to the term "treatment" refers to a subject or patient or individual who has been diagnosed with or is predisposed to a disease or infection. A patient may also be referred to being "at risk of suffering" from a disease or infection. This patient has not yet developed characteristic disease pathology or an active infection, however are known to be predisposed to the disease due to family history, being genetically predispose to developing the disease, being in an environment that puts the subject at substantial risk of being infected, or diagnosed with a disease or disorder that predisposes them to developing the disease to be treated.

Alhydrogel® is a commercially available (Accurate Chemical and Scientific Corporation, Catalogue #A1090S) wet gel colloidal suspension. The InvivoGen catalog (invivogen.com/PDF/AlhydrogelTDS.pdfd, last accessed on Oct. 23, 2017) describes Alhydrogel® adjuvant as an aluminium hydroxide wet gel suspension. Alhydrogel® particles have a net positive electrical charge at pH 5-7. Alhydrogel® adjuvant 2% is made by Brenntag Biosector, a leader in the global vaccine adjuvants market with along history of producing high quality products. Alhydrogel® adjuvant 2% was elected a the International Standard Preparation for aluminium hydroxide gels. Alhydrogel® adjuvant 2% is present in multiple commercial vaccine formulations.

100621 Whole glucan particles (WGP) intends particulate formulations of fungal glucan. It is a commercially available (InVivoGen Catalogue #tlrl-wgps) powder resuspended in water/saline. This has been used in the past as a vaccine adjuvant.

Mono-phosphoryl lipid (MPL) or lipid A intends a lipid component of an endotoxin held responsible for the toxicity of gram-negative bacteria. It has the chemical structure of:

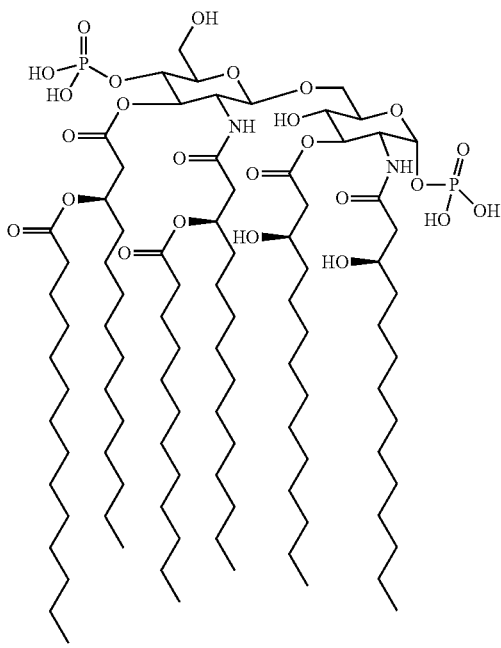 [SMILES: CCCCCCCCCCCCCC(=O)O[C@H](CCCCCCCCCCC)CC(=O)OC1C(NC(=O)C[C@@H](CCCCCCCCCCC)OC(=O)CCCCCCCCCCC)C(OCC2OC(OP(=O)(O)O)C(NC(=O)C[C@H](O)CCCCCCCCCCC)C(OC(=O)C[C@H](O)CCCCCCCCCCC)C2O)OC(CO)C1OP(=O)(O)O]

It is commercially available from InVivoGen (agog #tlrl-mpls) and Avanti Polar Lipids (catalogue #699800P). It has been used as a vaccine adjuvant.

As used herein, the term "mannan" intends polysaccharide found in fungi that is comprised of a mannose polymer (Sigma-Aldrich, catalogue number M7504, last accessed on Jan. 3, 2023 or Sigma Cat. #M3460-IG, or from MedicaPharma catalogue as "mannan", or from Newgreen Health Industry, catalogues as "mannan oligosaccharides").

As used herein, the term "antigen that induces an immune response against a bacterial or fungal pathogen" intends for example, conventional vaccine preparations used prophylactically and for treatment of infections and diseases associated with these infections and in one embodiment, intends only those which induce an immune response mediated by T and/or B lymphocytes against a pathogen, such as a viral, a bacterial or a fungal infection.

As used herein, the term "antigen" intends any substance that causes the body to make an adaptive immune response by T and/or B lymphocytes against that substance. Non-limiting examples of such antigens include toxins, chemicals, bacteria, viruses, or other substances that come from outside the body. Body tissues and cells, including cancer cells, also have antigens on them that can cause an immune response. These antigens can also be used as markers in laboratory tests to identify those tissues or cells. In one aspect, the term "antigen" as claimed herein intends only those which induce an immune response mediated by T and/or B lymphocytes against a pathogen, such as a viral, a bacterial or a fungal infection.

A "subject," "individual" or "patient" is used interchangeably herein, and refers to a vertebrate, preferably a mammal, more preferably a human. Mammals include, but are not limited to, murines, rats, rabbits, simians, bovines, ovines, porcines, canines, felines, farm animals, sport animals, pets, equines, and primates, particularly humans.

Compositions

This disclosure provides a composition comprising, or alternatively consisting essentially of, or yet further consisting of, an effective amount of each of: an aluminum hydroxide, a mono-phosphoryl lipid (MPL), and mannan (the combination referred to herein as "MMA"), with the proviso that the composition does not comprise an antigen effective to induce an immune response against a pathogen, e.g., a viral, fungal or bacterial pathogen. In one aspect, the "antigen" as claimed herein intends only those which induce an immune response mediated by T and/or B lymphocytes against a pathogen, such as a viral, a bacterial or a fungal infection.

In one aspect, the components are combined to achieve a final concentration. For example, the compositions have an combined concentration in a range from about 0.1 mg/ml to about 20 mg/ml, or alternatively from about 0.5 mg/ml to about 20 mg/ml, or alternatively from about 1.0 mg/ml to about 20 mg/ml, or alternatively from about 0.1 mg/ml to about 15 mg/ml, or alternatively from about 0.1 mg/ml to about 12 mg/ml, or alternatively from about 0.1 mg/ml to about 10 mg/ml, or alternatively from about 0.1 mg/ml to about 5 mg/ml, or alternatively from about 0.1 mg/ml to about 3 mg/ml, or alternatively from 0.1 mg/ml to about 2 mg/ml, or alternatively from about 200 µg/ml to about 20 mg/ml, or alternatively from about 0.1 mg/ml to about 15 mg/ml, or alternatively from about 0.1 mg/ml to about 13 mg/ml, or alternatively from about 0.5 mg/ml to about 13 mg/ml, or alternatively from about 0.5 mg/ml to about 12 mg/ml, or about 0.5 mg/ml, or about 1.0 mg/ml, or about 1.5 mg/ml, or about or about 1.5 mg/ml, or about 2.0 mg/ml, or about 3.5 mg/ml, or about 4.0 mg/ml, or about 8.0 mg/ml, or about 10 mg/ml, or about 12.0 mg/ml, or about 13 mg/ml, or about 15 mg/ml, or about 15.5 mg/ml, or about 6.0 mg/ml, or about 6.5 mg/ml, or about 7.0 mg/ml, or about 7.5 mg/ml, or about 8.0 mg/ml, or about 8.5 mg/ml, or about 9.0 mg/ml, or about 9.5 mg/ml or about 10 mg/ml.

The MMA is suspended in a carrier such as a pharmaceutically acceptable carrier such as PBS, to a concentration in a range from about 0.1 mg/ml to about 20 mg/ml, or alternatively from about 0.5 mg/ml to about 20 mg/ml, or alternatively from about 1.0 mg/ml to about 20 mg/ml, or alternatively from about 0.1 mg/ml to about 15 mg/ml, or alternatively from about 0.1 mg/ml to about 12 mg/ml, or alternatively from about 0.1 mg/ml to about 10 mg/ml, or alternatively from about 0.1 mg/ml to about 5 mg/ml, or alternatively from about 0.1 mg/ml to about 3 mg/ml, or alternatively from 0.1 mg/ml to about 2 mg/ml, or alternatively from about 200 µg/ml to about 20 mg/ml, or alternatively from about 0.1 mg/ml to about 15 mg/ml, or alternatively from about 0.1 mg/ml to about 13 mg/ml, or alternatively from about 0.5 mg/ml to about 13 mg/ml, or alternatively from about 0.5 mg/ml to about 12 mg/ml, or about 0.5 mg/ml, or about 1.0 mg/ml, or about 1.5 mg/ml, or about or about 1.5 mg/ml, or about 2.0 mg/ml, or about 3.5 mg/ml, or about 4.0 mg/ml, or about 8.0 mg/ml, or about 10 mg/ml, or about 12.0 mg/ml, or about 13 mg/ml, or about 15 mg/ml, or about 15.5 mg/ml, or about 6.0 mg/ml, or about 6.5 mg/ml, or about 7.0 mg/ml, or about 7.5 mg/ml, or about 8.0 mg/ml, or about 8.5 mg/ml, or about 9.0 mg/ml, or about 9.5 mg/ml or about 10 mg/ml.

The components of the MMA are combined in any appropriate combination and it is not intended that the ratios of each component be identical, although they can be combined in a 1:1:1 (Mannan:MPL:aluminum hydroxide) ratio. Alternatively the MMA in a ratio of about 0.5:0.05:1; about 1.5:0.15:1; about 1:0.1:1, about 3:0.3:1, about 5:0.5:1; about 10:3:1.

In some aspects, the MMA is combined with a carrier such as a pharmaceutically acceptable carrier such as saline, to provide a concentration from about 0.1 mg/ml to about 10 mg/ml, or alternatively from about 0.5 mg/ml to about 10 mg/ml, or alternatively from about 1.0 mg/ml to about 10 mg/ml, or alternatively from about 0.1 mg/ml to about 9 mg/ml, or alternatively from about 0.1 mg/ml to about 7 mg/ml, or alternatively from about 0.1 mg/ml to about 5 mg/ml0, or alternatively from about 0.1 mg/ml to about 3 mg/ml, or alternatively from about 0.1 mg/ml to about 2 mg/ml, or alternatively from about 0.1 mg/ml to about 1 mg/ml, or alternatively from about 200 µg/ml to about 8 mg/ml, or alternatively from about 0.1 mg/ml to about 5 mg/ml, or alternatively from about 0.1 mg/ml to about 3 mg/ml, or alternatively from about 0.5 mg/ml to about 3 mg/ml, or alternatively from about 0.5 mg/ml to about 2 mg/ml, or about 0.5 mg/ml, or about 1.0 mg/ml, or about 1.5 mg/ml, or about or about 0.5 mg/ml, or about 1.0 mg/ml, or about 1.5 mg/ml, or about 2.0 mg/ml, or about 3.0 mg/ml, or about 3.5 mg/ml, or about 4.0 mg/ml, or about 4.5 mg/ml, or about 5 mg/ml, or about 5.5 mg/ml, or about 6.0 mg/ml, or about 6.5 mg/ml, or about 7.0 mg/ml, or about 7.5 mg/ml, or about 8.0 mg/ml, or about 8.5 mg/ml, or about 9.0 mg/ml, or about 9.5 mg/ml or about 10 mg/ml.

The components of the MMA can be sourced from commercial vendors.

The compositions can be formulated for in vivo administration (in one or more doses) to administer from about 5 mcg/kg body weight to about 50 mcg/kg body weight, or alternatively 10 mcg/kg body weight to 50 mcg/kg body, or alternatively 20 mcg/kg body weight to about 50 mcg/kg body weight, or alternatively 10 mg/kg body weight to about 100 mcg/kg body weight, or alternatively from about 15 mcg/kg body weight to about 150 mcg/kg body weight, or alternatively from about 20 to mcg/kg body weight to about 200 mcg/kg body weight.

The compositions can be further formulated for storage and distribution such as by lyophilization or freeze-drying. In addition, preservative and stabilizing agents can be added to further enhance the shelf-life of the compositions.

Methods of Treatment

This disclosure also provides methods to enhance immunity in a subject against an infection caused by a bacterial or fungal pathogen by administering to the subject an effective amount of a composition as described above. The subject to be treated is any animal or human patient at risk of or has developed infection from a bacterial (gram-positive or gram-negative bacteria) or fungus. Non-limiting examples include sport and farm animals, pets and human patients. As used herein, the term "enhance immunity" intends to augment innate immune responses, including macrophage, neutrophil, dendritic cells, and gamma delta T cells and/or NK T cells, but does not include B-cell mediated antibody or T-cell stimulation that are characteristics of traditional, protein antigen-induced adaptive immunity. Methods to determine if an immune response has been elicited are known in the art and include, for example taking a suitable sample (blood, saliva or plasma) from a patient and assaying by ELISA cytokine levels, measuring the counts per ml of blood of various types of white blood cells, and whether antibodies against the pathogen or bacteria are present. In addition, non-invasive means such as a reduction in temperature of the subject can be used alone or in combination with clinical methods.

In one aspect, the bacterium is selected from *S. aureus, A. baumannii, K. Pneumoniae, P. aeruginosa, E. coli, Enterobacter* spp., *Serratia, Stenotrophomonas*, and the fungus is selected from *Candida* spp and fungi that cause the disease mucormycosis, including *Rhizopus* spp.

The composition can be administered in any suitable dose as determined by the treating physician, health care professional or veterinarian. Non-limiting examples of suitable methods of administration comprise intramuscular, subcutaneous, or intravenous administration. The effective amount to be administered is from about 5 mcg/kg body weight to about 50 mcg/kg body weight, or alternatively 10 mcg/kg body weight to 50 mcg/kg body, or alternatively 20 mcg/kg body weight to about 50 mcg/kg body weight, or alternatively 10 mg/kg body weight to about 100 mcg/kg body weight, or alternatively from about 15 mcg/kg body weight to about 150 mcg/kg body weight, or alternatively from about 20 to mcg/kg body weight to about 200 mcg/kg body weight.

In one aspect, the doses of MPL and aluminum are 50 µg and 500 µg, respectively to provide doses at from about 0.3, or about 0.4, or about 0.7 µg/kg (MPL) and from about 3, or about 4, or about 7 µg/kg (aluminum) weight-adjusted for a 70 kg adult.

In another aspect, the range of components in the MMA are as provided below in Table 1.

TABLE 1

| Component | Exemplary Dose* | Exemplary Human Dose |
| --- | --- | --- |
| Aluminum | 500 mg = 7 mg/kg | 500 mg = 7 mg/kg |
| MPL | 50 µg = 0.7 µg/kg | 1500 µg = 21 µg/kg |
| Mannan | N/A | 5,000 µg = 70 µg/kg |

*Assuming 70 kg adult human and 0.03 kg (30 gram) adult mouse

The doses are repeated as needed, e.g., a second, third or fourth dose as necessary. The MMA can be combined with PBS (e.g., 0.5 ml carrier), administered intra-muscularly.

TABLE 2

Exemplary Dosage Schemes

| | 1st Dose (day 1) | 2nd Dose (21-35 days) |
| --- | --- | --- |
| 1 | 500 µg aluminum + 50 µg MPL + 500 µg mannan | 500 µg aluminum + 50 µg MPL + 500 µg mannan |
| 2 | 500 µg aluminum + 150 µg MPL + 1500 µg mannan | 500 µg aluminum + 150 µg MPL + 1500 µg mannan |
| 3 | 500 µg aluminum + 500 µg MPL + 5000 µg mannan | 500 µg aluminum + 500 µg MPL + 5000 µg mannan |
| 4 | 500 µg aluminum + 1500 µg MPL + 5000 µg mannan | 500 µg aluminum + 1500 µg MPL + 5000 µg mannan |

Administration of the MMA vaccine can be combined with pre-administration monitoring, e.g., blood can be obtained prior to vaccination, and repeated at 1 and 2 weeks. Blood can be tested for standard complete blood count, chemistries, and liver function tests, and will also be stored for immunological testing.

In one aspect, the composition is once, twice, or three times over the period of one to three months.

In another aspect, the method further comprises assaying the subject for a bacterial or fungal infection prior to administration of the composition using methods known in the art or as described herein.

The composition can be administered in any suitable dose as determined by the treating physician, health care professional or veterinarian. Non-limiting examples of suitable methods of administration comprise intramuscular, subcutaneous, or intravenous administration. The effective amount to be administered is from about 25 to mcg/kg body weight to about 200 mcg/kg body weight, or alternatively from about 50 mcg/kg body weight to about 175 mcg/kg body weight, or alternatively from about 75 to mcg/kg body weight to about 200 mcg/kg body weight, or from about 25 to mcg/kg body weight to about 100 mcg/kg body weight, or from about 25 to mcg/kg body weight to about 175 mcg/kg body weight, or from about 25 to mcg/kg body weight to about 150 mcg/kg body weight, or from about 75 to mcg/kg body weight to about 200 mcg/kg body weight, or from about 75 to mcg/kg body weight to about 150 mcg/kg body weight, or from about 25 to mcg/kg body weight to about 150 mcg/kg body weight, or from about 50 to mcg/kg body weight to about 125 mcg/kg body weight, or from about 50 to mcg/kg body weight to about 100 mcg/kg body weight, or alternatively about 25 mcg/kg body weight, or alternatively about 75 mcg/kg body weight, or alternatively about 100 mcg/kg body weight, or alternatively about 125 mcg/kg body weight, or alternatively about 150 mcg/kg body weight, or alternatively about 175 mcg/kg body weight, or alternatively about 200 mcg/kg body weight.

The methods also can be used to treat or prevent a disorder caused by a bacterial or fungal infection in a subject in need thereof, the method comprising administering an effective amount of the composition as described above. The subject to be treated is any animal or human patient at risk of or has developed infection from a bacterial (gram-positive or gram-negative bacteria) or fungus. Methods to determine if a subject has been treated include, for example taking a suitable sample (blood, saliva or plasma) from a patient and assaying by ELISA cytokine levels, and whether antibodies against the pathogen or bacteria are present. In addition, non-invasive means such as a reduction in temperature of the subject can be used alone or in combination with clinical methods. In addition, depending on the disease being treated, a reduction of clinical or symptoms of the disease is an indication of effective treatment.

In one aspect, the bacterium is selected from *S. aureus, A. baumannii*, K. *Pneumoniae, P. aeruginosa, E. coli, Enterobacter* spp., *Serratia, Stenotrophomonas*, and the fungus is selected from *Candida* spp and the fungi that cause the disease mucormycosis, including *Rhizopus* spp.

The composition can be administered in any suitable dose as determined by the treating physician, health care professional or veterinarian. Non-limiting examples of suitable methods of administration comprise intramuscular, subcutaneous, or intravenous administration. The effective amount to be administered is from about 25 to mcg/kg body weight to about 200 mcg/kg body weight, or alternatively from about 50 mcg/kg body weight to about 175 mcg/kg body weight, or alternatively from about 75 to mcg/kg body weight to about 200 mcg/kg body weight, or from about 25 to mcg/kg body weight to about 100 mcg/kg body weight, or from about 25 to mcg/kg body weight to about 175 mcg/kg body weight, or from about 25 to mcg/kg body weight to about 150 mcg/kg body weight, or from about 75 to mcg/kg body weight to about 200 mcg/kg body weight, or from about 75 to mcg/kg body weight to about 150 mcg/kg body weight, or from about 25 to mcg/kg body weight to about 150 mcg/kg body weight, or from about 50 to mcg/kg body weight to about 125 mcg/kg body weight, or from about 50 to mcg/kg body weight to about 100 mcg/kg body weight, or alternatively about 25 mcg/kg body weight, or alternatively about 75 mcg/kg body weight, or alternatively about 100 mcg/kg body weight, or alternatively about 125 mcg/kg body weight, or alternatively about 150 mcg/kg body weight, or alternatively about 175 mcg/kg body weight, or alternatively about 200 mcg/kg body weight.

In one aspect, the composition is once, twice, or three times over the period of one to three months. In one aspect, the immunization is boosted at from about 14 to about 28 days, post-immunization, or from at from about 16 to about 26 days, post-immunization, or at from about 18 to about 24 days, post-immunization, or from about 20 to about 26 days, post-immunization, or from about 22 to about 23 days post-immunization, or from at about 3 weeks post-immunization.

The administration can be boosted with multiple administrations and/or administered in about 0.5×, or about 1×, or about 2×, or about 3×, or about 4×, or about 5×, or about 6×, or about 7×, or about 8×, or about 9×, or about 10×, or about 11×, or about 12×, or about 13, or about 14×, or about 15×or more of the base line dose, as determined by the treating physician. 1×MMA comprises 100 μg, 10 μg MPL and 200 μg aluminum hydroxide (2%); 3×MMA comprises 300 μg Mannan, 30 μg MPL, and 200 μg 2% aluminum hydroxide; and 10×comprise 1000 μg Mannan, 100 μg MPL, and 200 μg 2% aluminum hydroxide.

In another aspect, the method further comprises assaying the subject for a bacterial or fungal infection prior to administration of the composition using methods known in the art or as described herein.

Kits

Also provided herein is a kit comprising the compositions or formulations as described herein and instructions for use.

Drug Screening Assay

Also provided herein is a method to identify an compound or agent that provides a benefit selected from one or more of: enhances immunity against a bacterial or fungal microbial infection or treats a bacterial or fungal infection or a disease related to a bacterial or fungal microbial infection, the method comprising admixing the compound or agent with the composition as described herein and administering the admixed composition to a non human subject infected with a bacterial or fungal microorganism and assaying for post administration infection or survival, wherein the compound or agent that enhances the activity of the composition as described herein is a compound or an agent that provides the benefit. Methods to determine if an immune response has been elicited are known in the art and include, for example taking a suitable sample (blood, saliva or plasma) from a patient and assaying by ELISA cytokine levels, and whether antibodies against the pathogen or bacteria are present. In addition, non-invasive means such as a reduction in temperature of the subject can be used alone or in combination with clinical methods. Methods to determine if a subject has been treated include, for example taking a suitable sample (blood, saliva or plasma) from a patient and assaying by ELISA whether antibodies against the pathogen or bacteria are present. In addition, non-invasive means such as a reduction in temperature of the subject can be used alone or in combination with clinical methods. In addition, depending on the disease being treated, a reduction of clinical or symptoms of the disease is an indication of effective treatment.

The data generated from Experiments 1 through 7 are found in FIGS. 1 through 16. The data generated from Experiments 8 and 9 are found in FIGS. 17 to 22.

Preparation of Compositions

To prepare the compositions, the preferred amount of aluminum hydroxide is suspended in saline solution to a concentration in a range from about 0.1 mg/ml to about 10 mg/ml, or alternatively from about 0.5 mg/ml to about 10 mg/ml, or alternatively from about 1.0 mg/ml to about 10 mg/ml, or alternatively from about 0.1 mg/ml to about 9 mg/ml, or alternatively from about 0.1 mg/ml to about 7 mg/ml, or alternatively from about 0.1 mg/ml to about 5 mg/ml0, or alternatively from about 0.1 mg/ml to about 3 mg/ml, or alternatively from about 0.1 mg/ml to about 2 mg/ml, or altern0.1 mg/ml to about 1 mg/ml, or alternatively from about 200 μg/ml to about 8 mg/ml, or alternatively from about 0.1 mg/ml to about 5 mg/ml, or alternatively from about 0.1 mg/ml to about 3 mg/ml, or alternatively from about 0.5 mg/ml to about 3 mg/ml, or alternatively from about 0.5 mg/ml to about 2 mg/ml, or about 0.5 mg/ml, or about 1.0 mg/ml, or about 1.5 mg/ml, or about or about 0.5 mg/ml, or about 1.0 mg/ml, or about 1.5 mg/ml, or about 2.0 mg/ml, or about 3.0 mg/ml, or about 3.5 mg/ml, or about 4.0 mg/ml, or about 4.5 mg/ml, or about 5 mg/ml, or about 5.5 mg/ml, or about 6.0 mg/ml, or about 6.5 mg/ml, or about 7.0 mg/ml, or about 7.5 mg/ml, or about 8.0 mg/ml, or about 8.5 mg/ml, or about 9.0 mg/ml, or about 9.5 mg/ml or about 10 mg/ml.

In some aspect, mannan is dissolved in saline to provide a concentration of from about 0.1 mg/ml to about 10 mg/ml, or alternatively from about 0.5 mg/ml to about 10 mg/ml, or alternatively from about 1.0 mg/ml to about 10 mg/ml, or alternatively from about 0.1 mg/ml to about 9 mg/ml, or alternatively from about 0.1 mg/ml to about 7 mg/ml, or alternatively from about 0.1 mg/ml to about 5 mg/ml0, or alternatively from about 0.1 mg/ml to about 3 mg/ml, or alternatively from about 0.1 mg/ml to about 2 mg/ml, or alternatively from about 0.1 mg/ml to about 1 mg/ml, or alternatively from about 200 μg/ml to about 8 mg/ml, or alternatively from about 0.1 mg/ml to about 5 mg/ml, or alternatively from about 0.1 mg/ml to about 3 mg/ml, or alternatively from about 0.5 mg/ml to about 3 mg/ml, or alternatively from about 0.5 mg/ml to about 2 mg/ml, or about 0.5 mg/ml, or about 1.0 mg/ml, or about 1.5 mg/ml, or about or about 0.5 mg/ml, or about 1.0 mg/ml, or about 1.5 mg/ml, or about 2.0 mg/ml, or about 3.0 mg/ml, or about 3.5 mg/ml, or about 4.0 mg/ml, or about 4.5 mg/ml, or about 5 mg/ml, or about 5.5 mg/ml, or about 6.0 mg/ml, or about 6.5 mg/ml, or about 7.0 mg/ml, or about 7.5 mg/ml, or about 8.0 mg/ml, or about 8.5 mg/ml, or about 9.0 mg/ml, or about 9.5 mg/ml or about 10 mg/ml, prior to combination with MPL and aluminum hydroxide.

The preferred amount of MPL is added to the aluminum hydroxide and MPL combination to a concentration in a range from about 0.1 mg/ml to about 10 mg/ml, or alternatively from about 0.5 mg/ml to about 10 mg/ml, or alternatively from about 1.0 mg/ml to about 10 mg/ml, or alternatively from about 0.1 mg/ml to about 9 mg/ml, or alternatively from about 0.1 mg/ml to about 7 mg/ml, or alternatively from about 0.1 mg/ml to about 5 mg/ml0, or alternatively from about 0.1 mg/ml to about 3 mg/ml, or alternatively from about 0.1 mg/ml to about 2 mg/ml, or altern0.1 mg/ml to about 1 mg/ml, or alternatively from about 200 μg/ml to about 8 mg/ml, or alternatively from about 0.1 mg/ml to about 5 mg/ml, or alternatively from about 0.1 mg/ml to about 3 mg/ml, or alternatively from about 0.5 mg/ml to about 3 mg/ml, or alternatively from about 0.5 mg/ml to about 2 mg/ml, or about 0.5 mg/ml, or about 1.0 mg/ml, or about 1.5 mg/ml, or about or about 0.5 mg/ml, or about 1.0 mg/ml, or about 1.5 mg/ml, or about 2.0 mg/ml, or about 3.0 mg/ml, or about 3.5 mg/ml, or about 4.0 mg/ml, or about 4.5 mg/ml, or about 5 mg/ml, or about 5.5 mg/ml, or about 6.0 mg/ml, or about 6.5 mg/ml, or about 7.0 mg/ml, or about 7.5 mg/ml, or about 8.0 mg/ml, or about 8.5 mg/ml, or about 9.0 mg/ml, or about 9.5 mg/ml or about 10 mg/ml.

The MMA is suspended in pharmaceutically acceptable carriers such as PBS and optionally DMSO, to a concentration in a range from about 0.1 mg/ml to about 10 mg/ml, or alternatively from about 0.5 mg/ml to about 10 mg/ml, or alternatively from about 1.0 mg/ml to about 10 mg/ml, or alternatively from about 0.1 mg/ml to about 9 mg/ml, or alternatively from about 0.1 mg/ml to about 7 mg/ml, or alternatively from about 0.1 mg/ml to about 5 mg/ml0, or alternatively from about 0.1 mg/ml to about 3 mg/ml, or alternatively from about 0.1 mg/ml to about 2 mg/ml, or altern0.1 mg/ml to about 1 mg/ml, or alternatively from about 200 μg/ml to about 8 mg/ml, or alternatively from about 0.1 mg/ml to about 5 mg/ml, or alternatively from about 0.1 mg/ml to about 3 mg/ml, or alternatively from about 0.5 mg/ml to about 3 mg/ml, or alternatively from about 0.5 mg/ml to about 2 mg/ml, or about 0.5 mg/ml, or about 1.0 mg/ml, or about 1.5 mg/ml, or about or about 0.5 mg/ml, or about 1.0 mg/ml, or about 1.5 mg/ml, or about 2.0 mg/ml, or about 3.0 mg/ml, or about 3.5 mg/ml, or about 4.0 mg/ml, or about 4.5 mg/ml, or about 5 mg/ml, or about 5.5 mg/ml, or about 6.0 mg/ml, or about 6.5 mg/ml, or about 7.0 mg/ml, or about 7.5 mg/ml, or about 8.0 mg/ml, or about 8.5 mg/ml, or about 9.0 mg/ml, or about 9.5 mg/ml or about 10 mg/ml.

In one aspect, the components are combined to achieve a final concentration. For example, the compositions have an combined concentration in a range from about 0.1 mg/ml to about 20 mg/ml, or alternatively from about 0.5 mg/ml to about 20 mg/ml, or alternatively from about 1.0 mg/ml to about 20 mg/ml, or alternatively from about 0.1 mg/ml to about 15 mg/ml, or alternatively from about 0.1 mg/ml to about 12 mg/ml, or alternatively from about 0.1 mg/ml to about 10 mg/ml, or alternatively from about 0.1 mg/ml to about 5 mg/ml, or alternatively from about 0.1 mg/ml to about 3 mg/ml, or alternatively from 0.1 mg/ml to about 2 mg/ml, or alternatively from about 200 μg/ml to about 20 mg/ml, or alternatively from about 0.1 mg/ml to about 15 mg/ml, or alternatively from about 0.1 mg/ml to about 13 mg/ml, or alternatively from about 0.5 mg/ml to about 13 mg/ml, or alternatively from about 0.5 mg/ml to about 12 mg/ml, or about 0.5 mg/ml, or about 1.0 mg/ml, or about 1.5 mg/ml, or about or about 1.5 mg/ml, or about 2.0 mg/ml, or about 3.5 mg/ml, or about 4.0 mg/ml, or about 8.0 mg/ml, or about 10 mg/ml, or about 12.0 mg/ml, or about 13 mg/ml, or about 15 mg/ml, or about 15.5 mg/ml, or about 6.0 mg/ml, or about 6.5 mg/ml, or about 7.0 mg/ml, or about 7.5 mg/ml, or about 8.0 mg/ml, or about 8.5 mg/ml, or about 9.0 mg/ml, or about 9.5 mg/ml or about 10 mg/ml.

The compositions can be formulated for in vivo administration (in one or more doses) to administer from about 5 mcg/kg body weight to about 50 mcg/kg body weight, or alternatively 10 mcg/kg body weight to 50 mcg/kg body, or alternatively 20 mcg/kg body weight to about 50 mcg/kg body weight, or alternatively 10 mg/kg body weight to about 100 mcg/kg body weight, or alternatively from about 15 mcg/kg body weight to about 150 mcg/kg body weight, or alternatively from about 20 to mcg/kg body weight to about 200 mcg/kg body weight. Exemplary doses are disclosed herein and incorporated herein by reference.

| Component | Starting Dose | Maximum Intended Human Dose |
|---|---|---|
| Aluminum | 500 µg = 7 µg/kg | 500 µg = 7 µg/kg |
| MPL | 50 µg = 0.7 µg/kg | 1500 µg = 21 µg/kg |
| Mannan | 500 µg = 7 µg/kg | 5,000 µg = 70 µg/kg |

Assuming 70 kg adult

Experiment 1: Discovery of Adjuvant-Induced Immunity—Materials and Methods Adjuvant Immunization Mannan (Sigma Cat. #M3640-1G), Monophosphoryl lipid A (MPL) (InvivoGen Cat. #tlrl-mpls), whole glucan particles (WGP) (InvivoGen Cat. #tlrl-wgp), 2% aluminum hydroxide (Al(OH)$_3$) gel (Accurate Chemical & Scientific Corporation Cat. #A1090S) are prepared and stored according to the manufacture protocol. Mannan (MedicaPharma Cat. #mannan), PHAD® (Avanti Polar Lipids Cat. #699800P), and 2% (Al(OH)$_3$)gel (Croda Cat. #AJV3012) were used as GMP grade MMA. Mice were immunized with 200 µL administered subcutaneously (SC) in the scruff of the neck with pre-mixed adjuvant mixtures in phosphate-buffered saline (PBS).

Intravenous (IV) Infection

Frozen stocks of *A. baumannii* and *K pneumoniae* bacteria grown to mid-log phase were prepared as previously described (15). Inocula were prepared by diluting these concentrated frozen stocks of bacteria in PBS. Inocula were confirmed by plating serial dilutions on tryptic soy agar (TSA) plates and incubating overnight at 37° C. Mice infected with *A. baumannii* were monitored for seven days and mice infected with *K pneumoniae* were monitored for 14 days, after which they were euthanized according to our IACUC protocol.

*S. aureus* inocula were prepared from mid-log phase subcultures of overnight cultures for each infection. Briefly, *S. aureus* was inoculated into tryptic soy broth (TSB) and incubated overnight at 37° C. with shaking set to 200 rpm. A subculture was set up from a 1:100 dilution of the overnight culture into sterile TSB and incubated for 3 h at 37° C. with shaking set to 200 rpm. The subculture was rinsed by pelleting in a refrigerated centrifuge at 4,000×g for 5 min and resuspending the pellet in PBS. After two more rinses (three total), the pellet was resuspended in PBS and adjusted the optical density at 600 nm (OD$_{600}$) to 0.5 using PBS. Applicant had used an established correlation coefficient at this optical density to estimate the inoculum concentration (OD$_{600}$ 0.5≈2.4×10$^8$ CFU/mL). Inocula were confirmed by plating serial dilutions on TSA plates and incubating overnight at 37° C. Mice infected with *S. aureus* were monitored for 28 days, after which they were euthanized according to our IACUC protocol.

Oral Aspiration (OA) Infection

Mice were infected using OA model as previously described (9). Briefly, *A. baumannii* HUMC1 inocula were prepared from subcultures of overnight cultures, as stated above, mice were infected by aspirating 50 µL of bacteria suspended in PBS. Mice infected with *A. baumannii* via OA were monitored for seven days, after which they were euthanized according to our IACUC protocol.

Mouse Knockout (KO) Strains

RAG1 KO (strain #034159) and human CD34$^+$ hematopoietic stem-cell-engrafted NSG mice were purchased from Jackson Laboratories.

Innate Immune Cell Depletion

Macrophages were depleted by injecting liposomal clodronate (C-010, Foundation Clodronate Liposomes) IP at 50 µg/g (e.g. 30-g mouse received 300 µL or 1.5 mg liposomal clodronate) three days before infection.

Neutrophils were depleted by injecting cyclophosphamide (Baxter) IP at 230 mg/kg three days before infection. Neutropenia last 6 days (14, 16).

NK cells were depleted by injecting anti-Asialo-GM1 antibody (Poly21460, Biolegend, 341/mouse) at every three to four days starting on the day of immunization (17).

Flow Cytometry Analysis

The spleens of mice were collected, mashed through a 70-µm cell strainer with a 35-mL syringe plunger, and rinsed with Dulbecco's modified Eagle medium (DMEM) supplemented with 10% fetal bovine serum (FBS) by volume (DMEM+10% FBS). The cell suspension was pelleted in a room-temperature centrifuge at 300×g for 5 min, and the supernatant was discarded. After two more rinses (three total), red blood cells (RBC) were lysed using RBC lysis buffer (BioLegend Cat. #420301) according to the manufacture's protocol. Splenocytes were resuspended in PBS with 5% Fetal Bovine Serum (FACS buffer), counted with a hemacytometer, incubated with Fc blocker (BD Biosciences Cat. #553141) for 30 min on ice. Splenocyte were pelleted in a room-temperature centrifuge at 300×g for 5 min, resuspended in FACS buffer, and incubated with fluorophore-conjugated antibodies for OMIP-032, a two-panel, multi-color immunophenotyping to assess innate and adaptive immune cells as previously described (18). After incubation, splenocytes were washed twice in a room-temperature centrifuge at 300×g for 5 min and resuspended in FACS buffer. Samples were analyzed using a BD FACS Canto II flow cytometer.

Statistics

Survival was compared by the non-parametric Log-Rank test with α=0.05. Mac assay, cfu, cytokines, chip-seq were compared by Wilcoxon-Mann-Whitney test with α=0.05.

J In an effort to develop a vaccine against *S. aureus* bacteremia, efficacy of prior combinations were compared. Mice were injected with a group of protein antigens combined with one or more adjuvants, and incorporating adjuvant-only immunized mice as negative controls. All mice were then challenged intravenously (IV) with a clinical blood isolate of *S. aureus* MRSA USA300 strain LAC. Applicant observed that mice immunized with multiple adjuvants experienced a survival advantage compared to mice immunized with only one adjuvant, regardless of whether the vaccine included protein antigens (FIG. 1A). Specifically, mice immunized with whole glucan particles (WGP) and lipopolysaccharide (LPS) (WGP+LPS) experienced the same level of survival as mice immunized with the same two adjuvants plus a group of recombinant *S. aureus* surface antigens (WGP+LPS+Ag). Similarly, mice additionally immunized with aluminum hydroxide (Al(OH)$_3$) (Al(OH)$_3$+WGP+LPS) survived at a similar level as mice additionally immunized with monophosphoryl lipid A (MPL) and the same group of recombinant protein antigens (Al(OH)$_3$+WGP+LPS+MPL+Ag) (FIG. 1A).

Figure 1B:
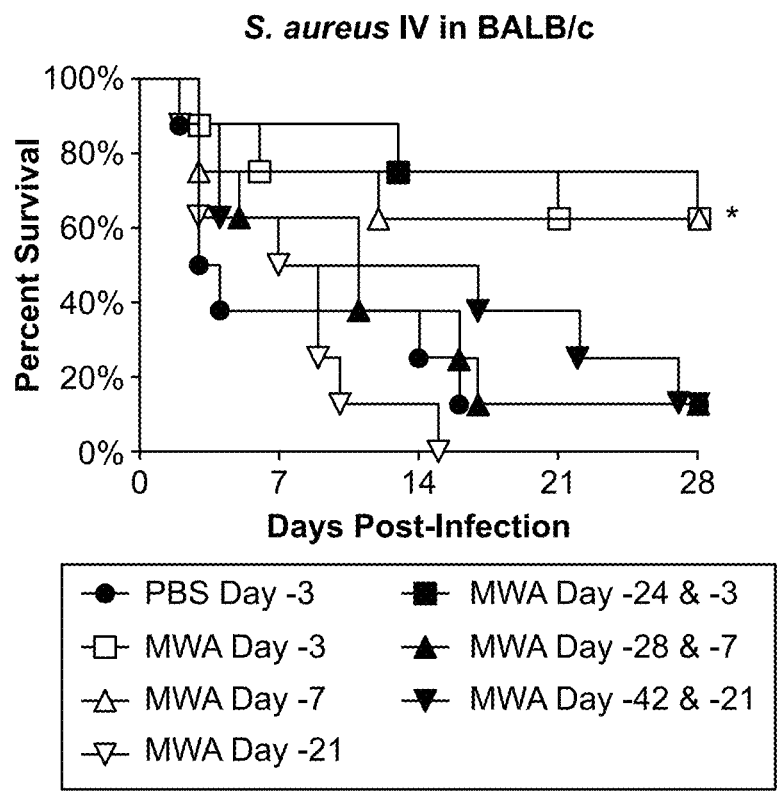

To evaluate the impact of immunizations booster shots on vaccine efficacy, Applicant immunized mice with phosphate-buffered saline (PBS) or MPL, WGP, and Al(OH)$_3$ (MWA); half of the mice were administered an identical booster shot three weeks after their first immunization. Mice were then challenged IV with *S. aureus* LAC three, seven, or 21 days after the final immunization. For the single dose recipients, protection against infection persisted for 3 and 7 days after the dose, but had waned by 21 days (FIG. 1B). These results demonstrated that an adjuvant-only vaccine provides short-term protection against *S. aureus* bacteremia with only a single immunization. The booster dose restored protection for a further 3 days, but not a further 21 days (FIG. 1B).

Figure 1C:
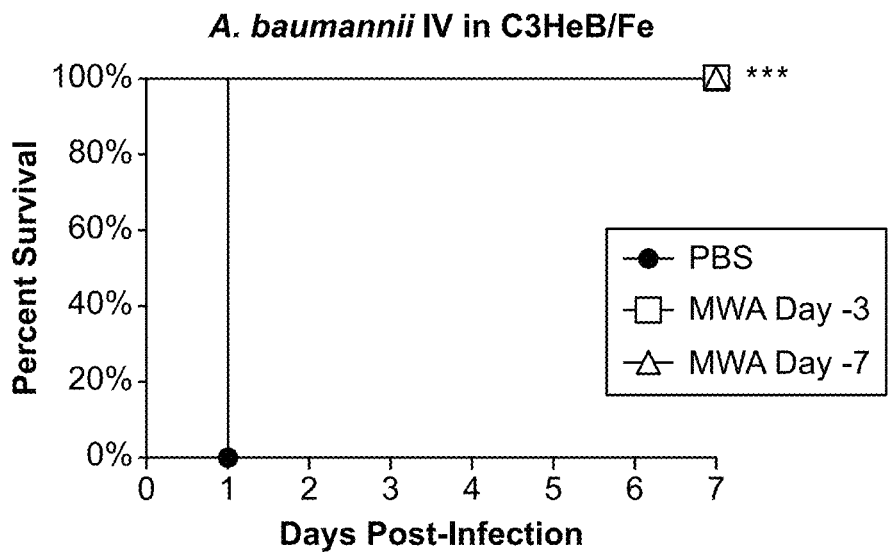

Since the innate immune stimulatory components of the tripartite vaccine do not specifically target *S. aureus*, Applicant investigated the ability of the vaccine to protect against bacteremia caused by the Gram-negative bacterium, *Acinetobacter baumannii*. Mice were immunized with PBS or MWA and infected three or seven days post-immunization with an extremely drug-resistant ( )CDR), clinical lung and blood isolate of *A. baumannii* HUMC1. Both groups of immunized mice were fully protected against an otherwise lethal infection (FIG. 1C).

Experiment 2: Defining Contributions of the Vaccine Components

Figure 1D:
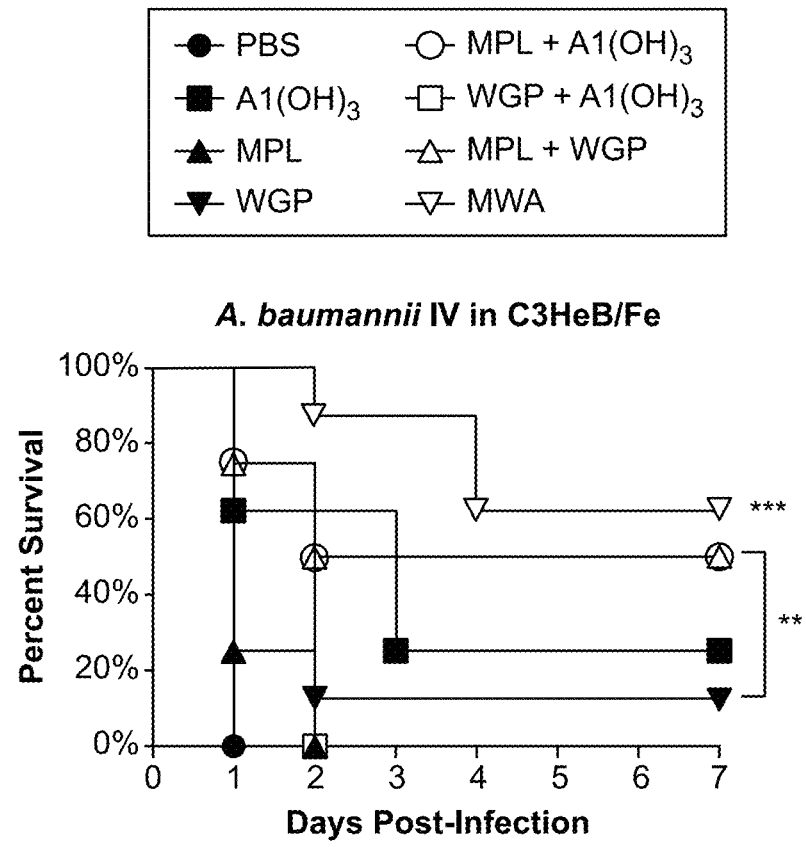

Although mice immunized with MWA were fully protected against *A. baumannii* bacteremia, they were only partially protected against *S. aureus* bacteremia. Thus, Applicant explored how each component of the vaccine contributed to protection against lethal infections. Applicant immunized mice with zero, one, two, or all three adjuvants and challenged them three days later with a larger inoculum of *A. baumannii*, enabling differentiation between the survival benefits conferred on each immunization group. Compared to other groups, MWA provided the greatest protection (FIG. 1D).

Figure 1E:
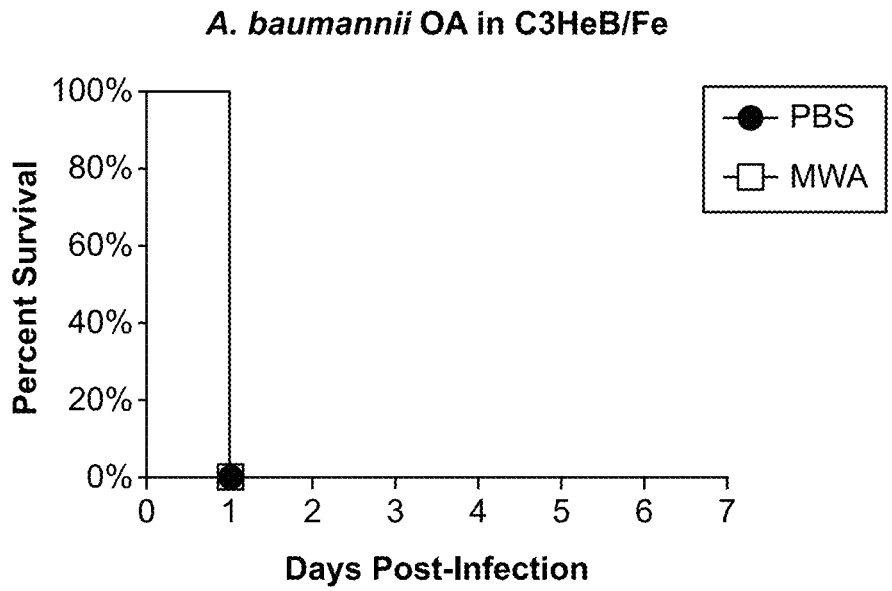

Having established the superiority of MWA, Applicant next considered whether the triple-adjuvant vaccine could protect against another common route of infection in hospitalized patients, aspiration pneumonia, using our previously described oropharyngeal aspiration (OA) pneumonia model (9). Despite protecting against bacteremia, MWA did not protect against *A. baumannii* pneumonia infection (FIG. 1E).

Figure 1F:
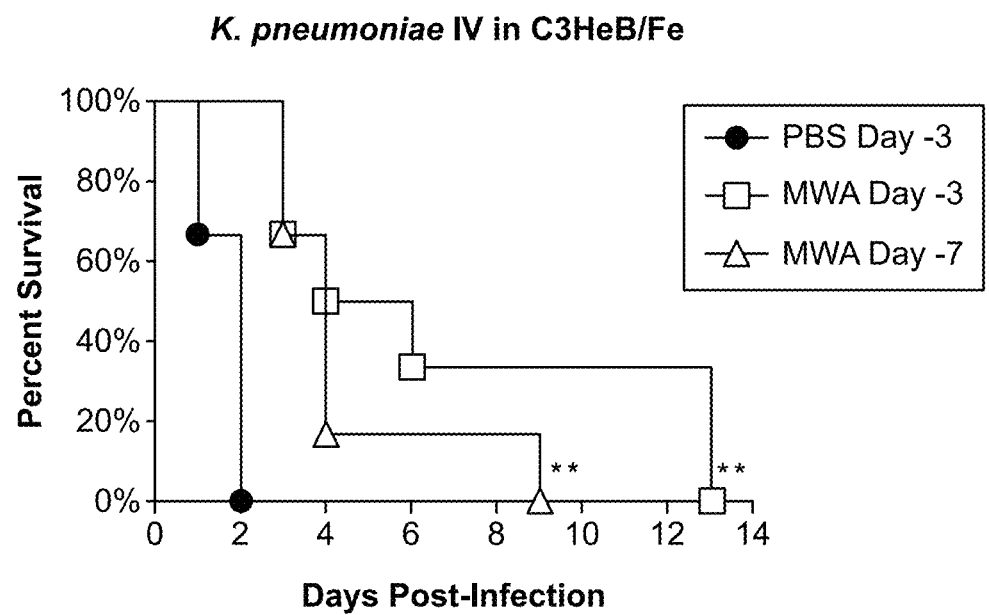
Figure 1G:
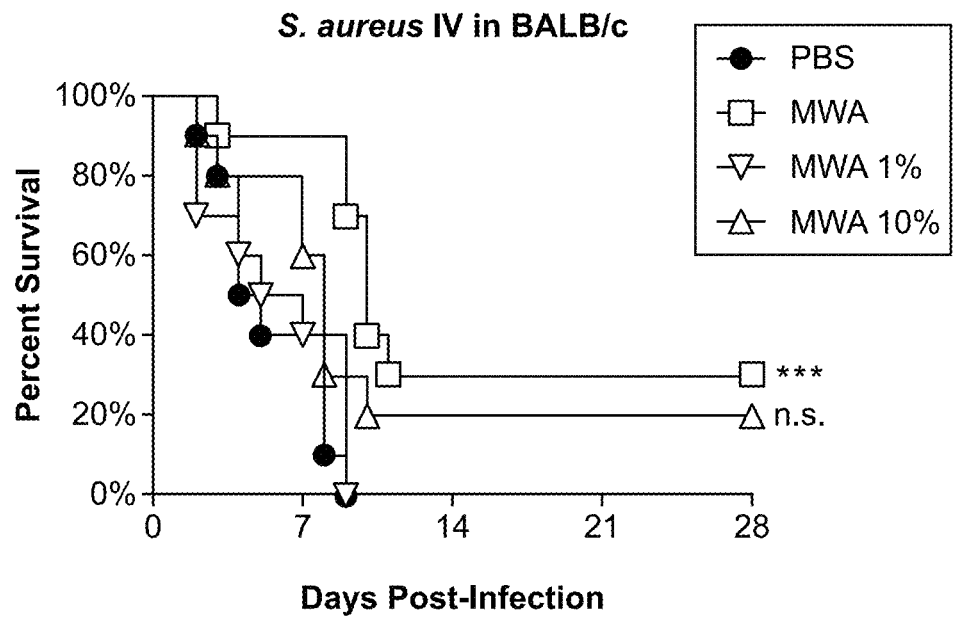
Figure 1H:
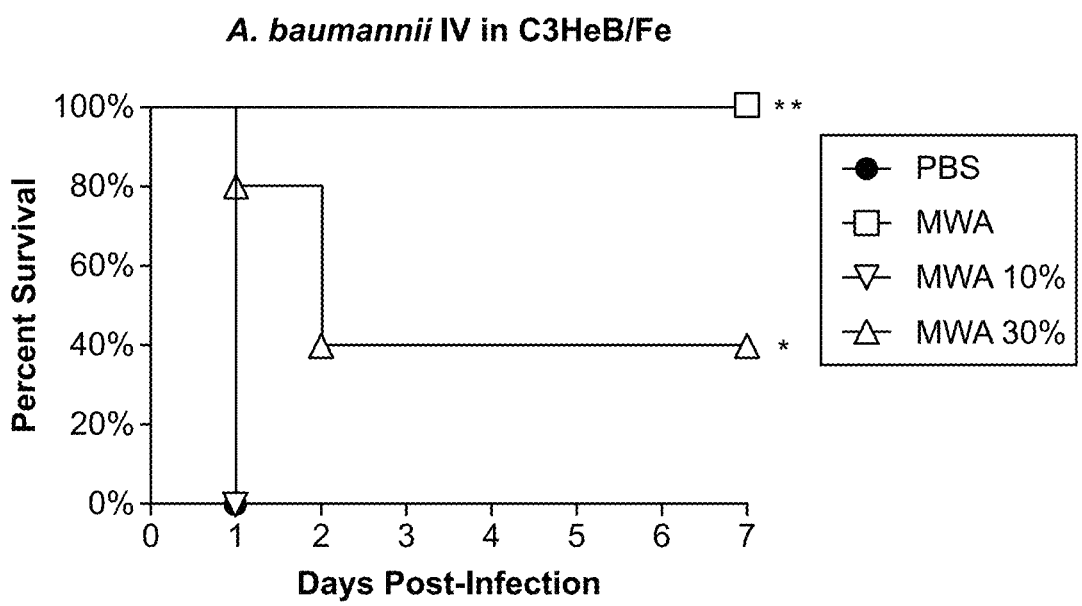

Applicant also assessed the ability of the vaccine to protect against lethal infection from *Klebsiella pneumoniae*, another Gram-negative bacterium in our bacteremia model. Although no mice survived, the immunized groups experienced delayed mortality compared to the placebo group when infected with the *K pneumoniae* clinical blood isolate KP3 (FIG. 1F). Finally, Applicant explored the effects of lowered dosing, and finding that reduced doses resulted in reduced efficacy in a dose-dependent manner (FIGS. 1G-H).

Experiment 3: Optimization of the Triple Regimen with Mannan

Figure 2A:
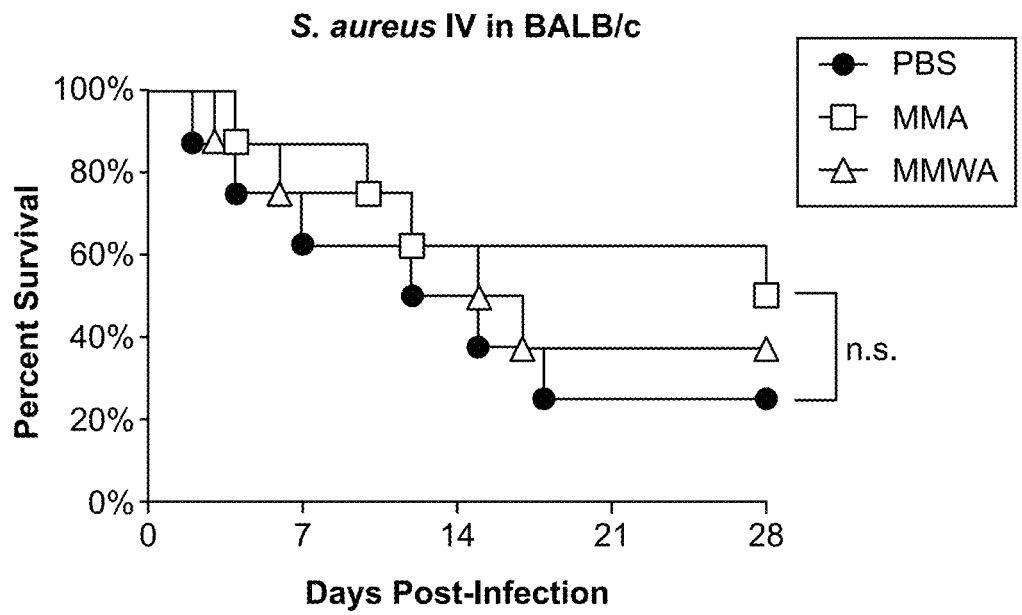
FIGS. 2A-2E show that replacing WGP with mannan expanded coverage and increased the efficacy of protection. All vaccinations were administered SC as a 0.2 ml suspension in PBS. MMA (100 μg Mannan, 10 μg MPL, and 0.2 mg Al(OH)$_3$); or MMWA (100 μg Mannan, 10 μg MPL, 100 μg WGP, and 0.2 mg Al(OH)$_3$). Three days after the immunization, (FIG. 2A) female BALB/c mice (N=8 per group) were infected IV via the tail vein with $6.9 \times 10^7$ CFU *S. aureus* LAC, (FIG. 2B) male C3HeB/Fe mice (N=5 per group) were infected IV via the tail vein with $1.4$-$2.9 \times 10^7$ CFU *A. baumannii* HUM1, (FIG. 2C) male C3HeB/Fe mice (N=5 per group) were infected IV via the tail vein with $2.4 \times 10^8$ CFU *K pneumoniae* KPC-KP 1, (FIG. 2D) female BALB/c mice (N=5 per group) were infected IV via the tail vein with $3.0 \times 10^3$ CFU *Rhizopus delemar* 99-880, and (FIG. 2E) male C3HeB/Fe mice (N=5 per group) were infected via oral aspiration (OA) with $1.6 \times 10^8$ CFU *A. baumannii* HUMC 1. Survival was compared by the non-parametric Log-Rank test with $\alpha=0.05$. *$p \leq 0.05$, **$p \leq 0.01$ vs PBS group.
Figure 2B:
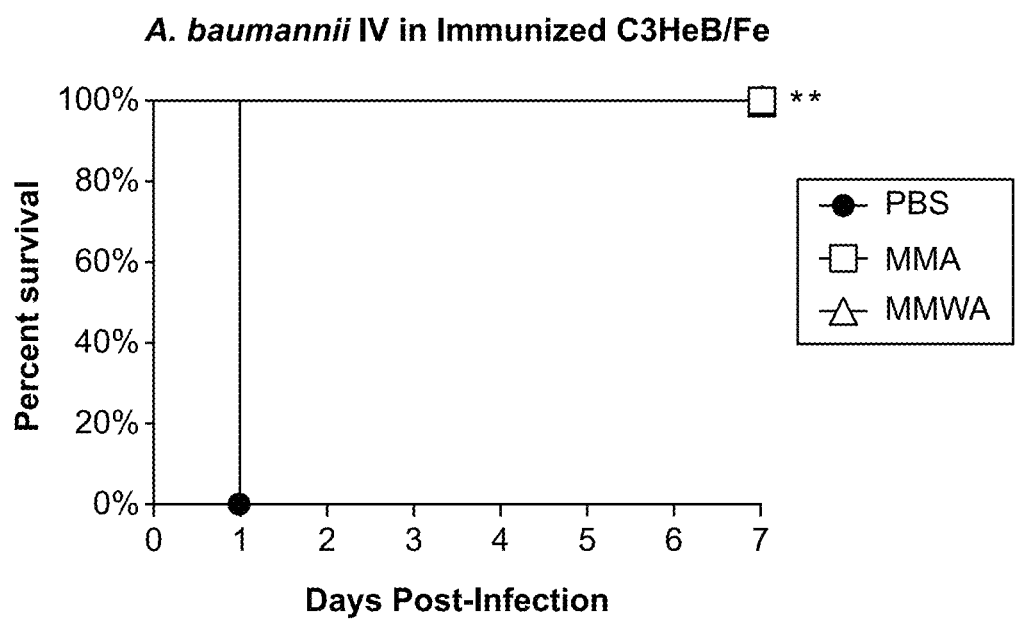
Figure 2C:
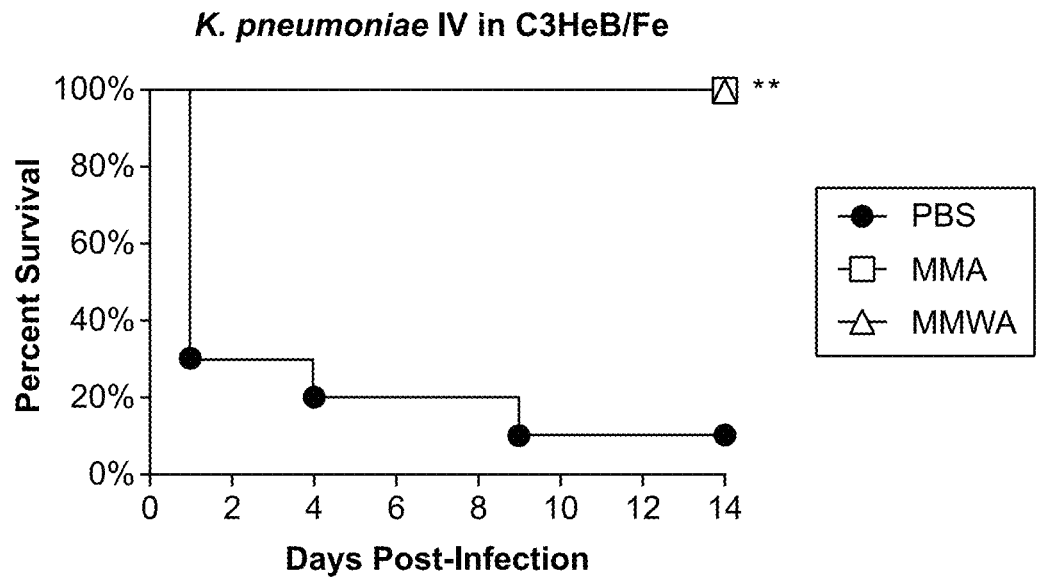
Figure 2D:
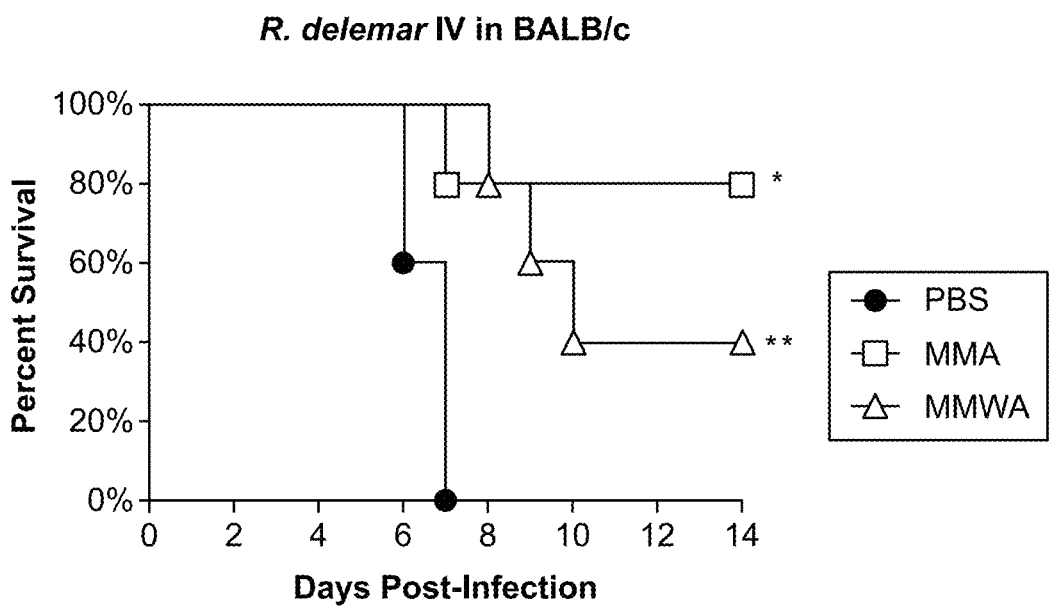
Figure 2E:
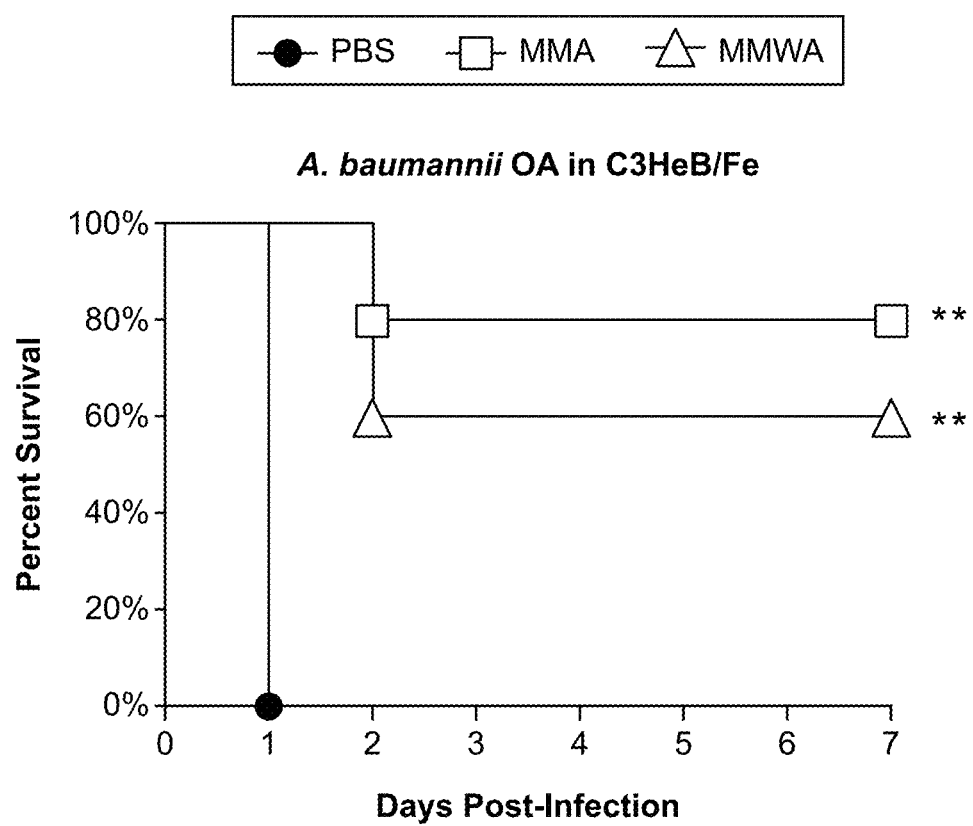

Based on prior experience working with mannosylated protein (10), Applicant sought to enhance vaccine efficacy by incorporating mannan, an oligosaccharide shown to have immunomodulating properties. Mice were immunized with either mannan in addition to MWA (MMWA) or mannan instead of WGP (MMA). Three days later, mice were challenged with a normally lethal inoculum of *S. aureus*, *A. baumannii, K pneumoniae*, or neutropenic mice infected with the fungus *Rhizopus delemar* (FIGS. 2A-D). Overall, the vaccine with mannan substituted for WGP (MMA) provided superior protection against lethal infections of all four pathogens, including in the neutropenic mouse model of mold infection (FIGS. 2A-D). Furthermore, mannan helped confer a dramatic survival advantage in mice infected with *A. baumannii* pneumonia (FIG. 2E).

Experiment 4: Optimization of Vaccine Dosage

Figure 3A:
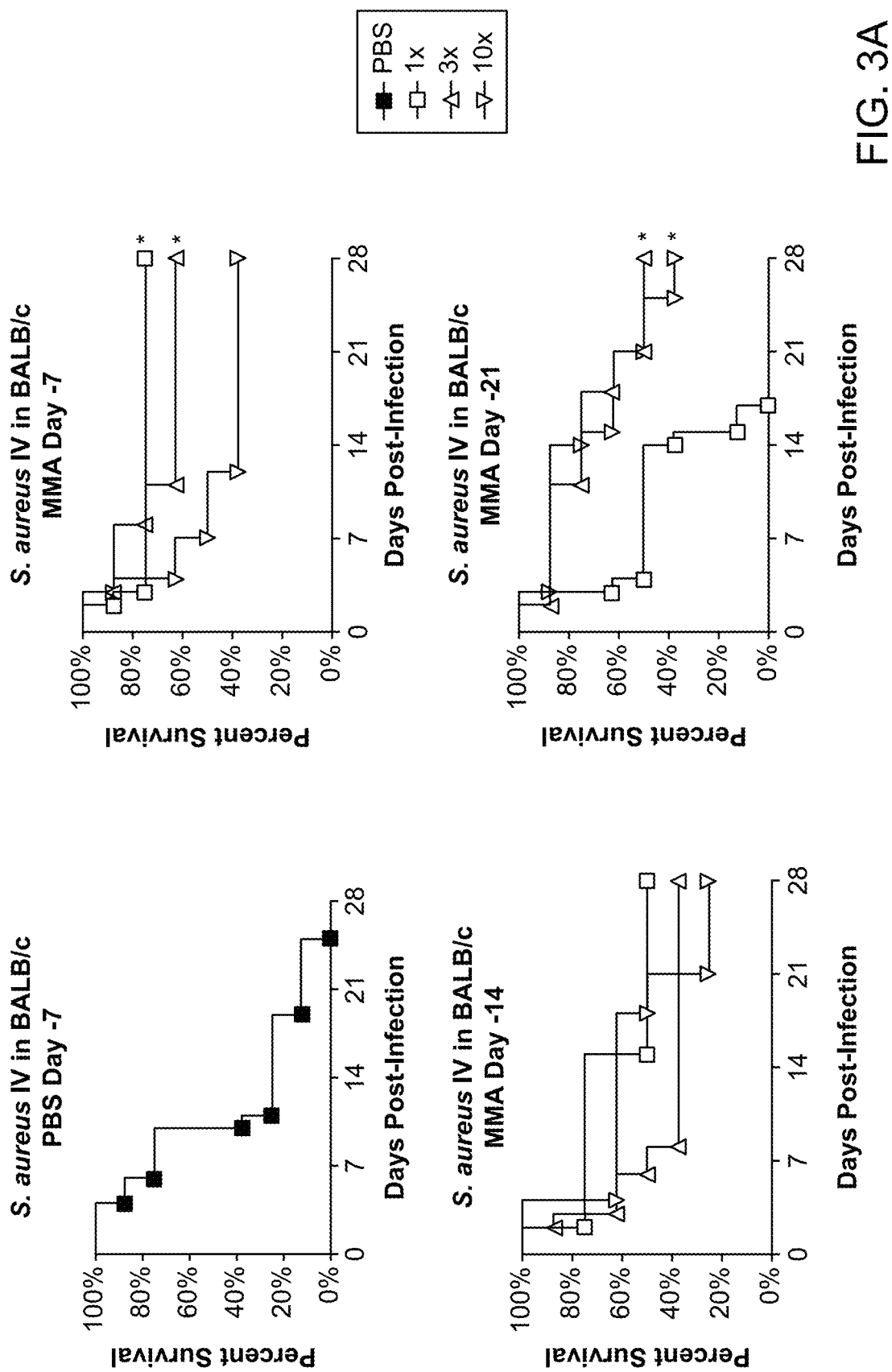
FIGS. 3A-3H show extending the duration of protection by higher adjuvants dosing and innate vs adaptive immunity. All vaccinations were administered SC as a 0.2 ml suspension in PBS. MMA 1×(100 μg Mannan, 10 μg MPL, and 0.2 mg Al(OH)$_3$); MMA 3×(300 μg Mannan, 30 μg MPL, and 0.2 mg Al(OH)$_3$), or MMA 10×(1,000m Mannan, 100 μg MPL, and 0.2 mg Al(OH)$_3$). Seven, 14, or 21 days after the immunization, (FIG. 3A) female BALB/c mice (N=8 per group) were infected IV via the tail vein with $9.7 \times 10^7$ CFU *S. aureus* LAC and (FIG. 3B) male C3HeB/Fe mice (N=5 per group) were infected IV via the tail vein with $2.9 \times 10^7$ CFU *A. baumannii* HUMC1.
Figure 3B:
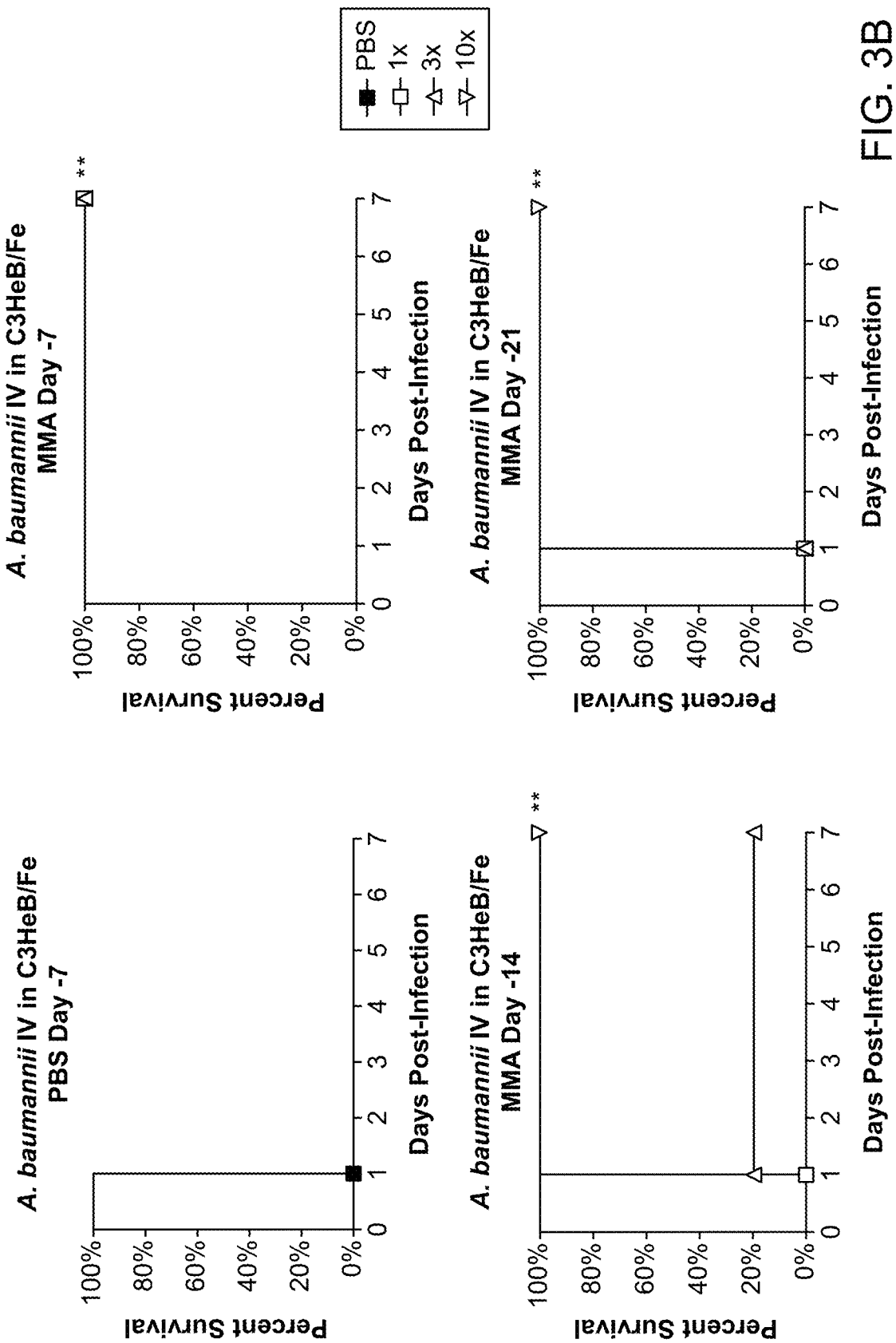

Having established that MMA was superior to MWA or MMWA, and that MMA protected mice three days post-immunization, Applicant next sought to evaluate whether increased doses could enhance protection and how long the vaccine would protect after immunization. Applicant immunized mice with three (3×) or ten times (10×) as much mannan and MPL, and challenged them one, two, or three weeks later with lethal *S. aureus* or *A. baumannii* bacteremia (FIGS. 3A-B). Higher doses resulted in protection out to 21 days, whereas protection ended more quickly with lower doses.

Figures 3C, 3D:
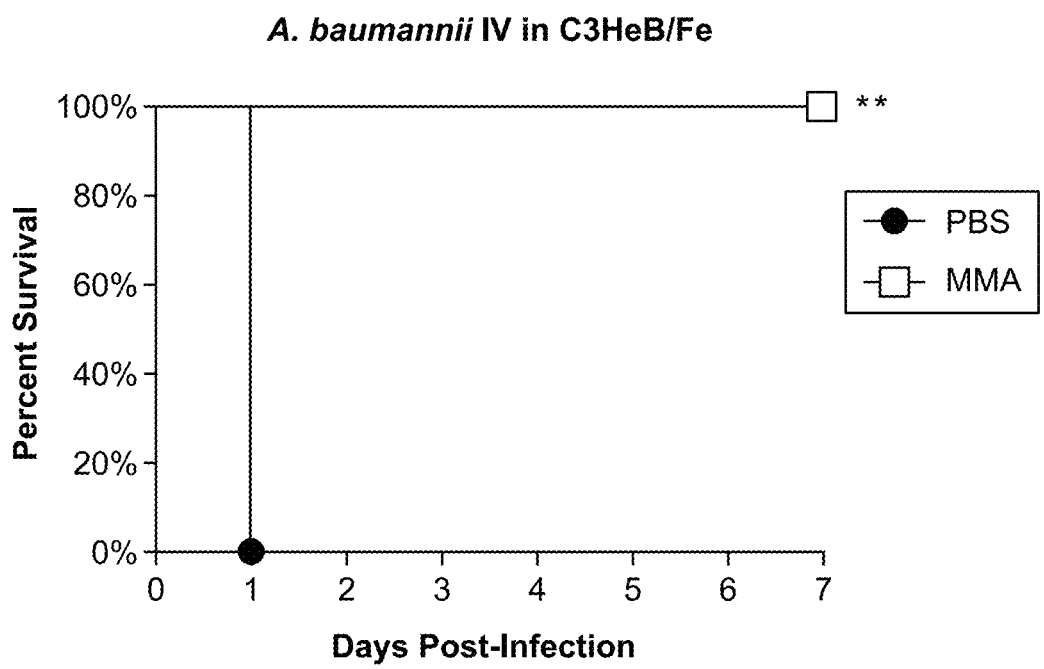

For *A. baumannii* bacteremia, all three doses provided full protection when mice were challenged one week post-immunization (FIG. 3B). However, only the largest dose (10×) provided full protection when mice were challenged two or three weeks post-immunization (FIG. 3B). To be sure that the protective effects were not due to antibody-mediated immunity, Applicant analyzed the serum of vaccinated mice and confirmed that immunizations did not result in antibodies specific to *A. baumannii* or *S.aureus* (FIG. 3C).

Figure 3E:
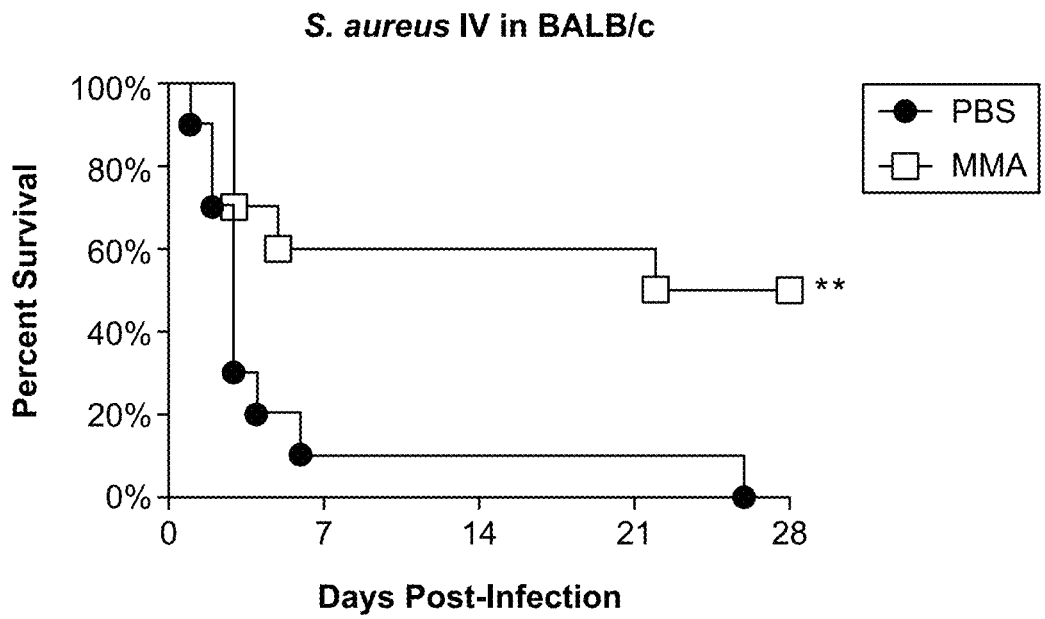
Figure 3F:
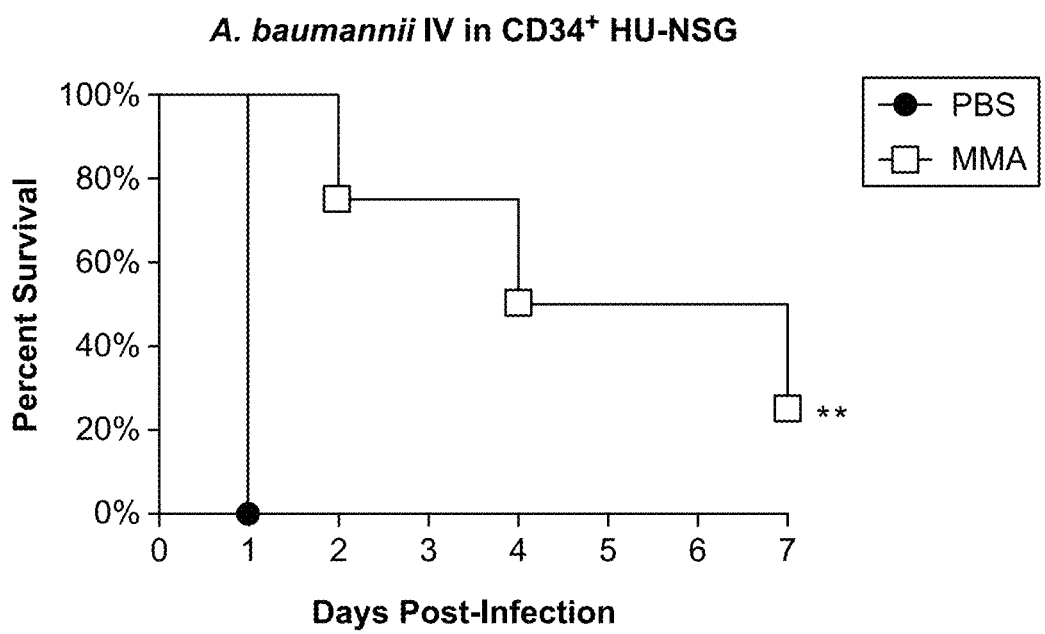
Figure 3G:
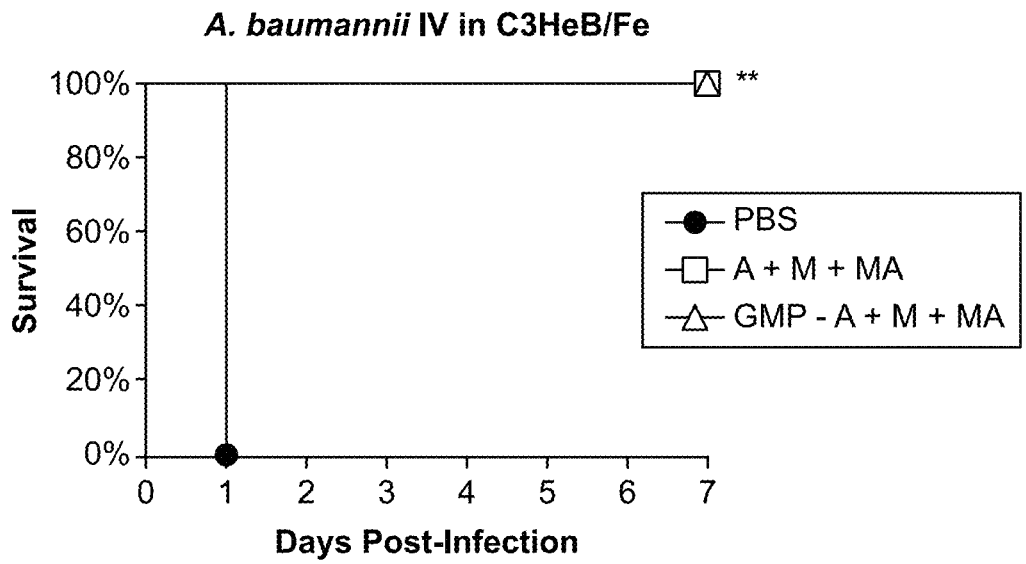
Figure 3H:
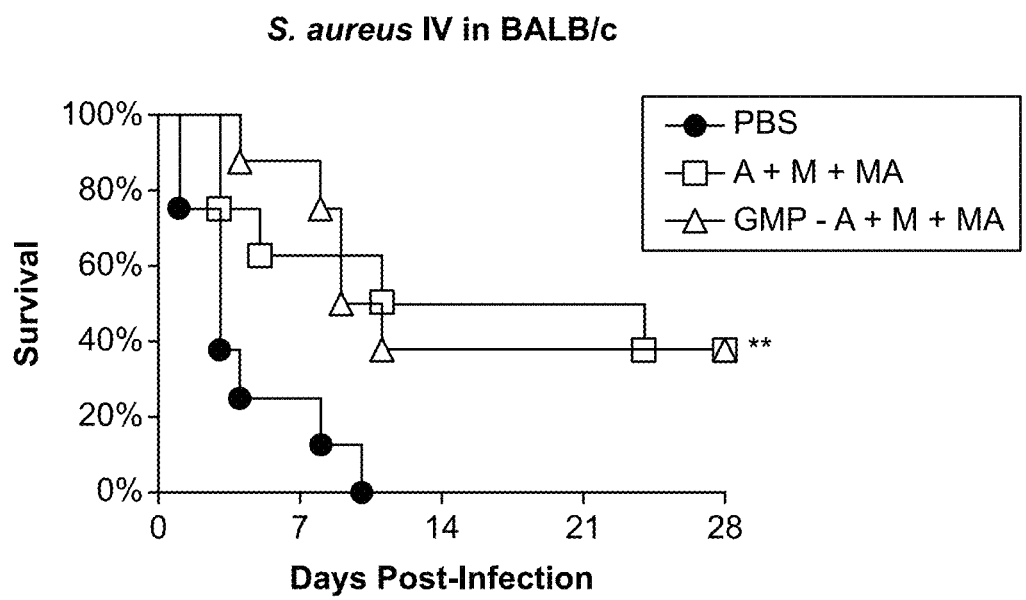

Applicant next sought to define the rapidity of onset of protection. Applicant immunized mice with the standard (1×) dose of MMA and challenged them with lethal *A. baumannii* or *S. aureus* bacteremia 24 h post-immunization; MMA provided full protection (FIG. 3D), or similar protection as Day −3 (FIG. 3E). To assess its translatability to humans, Applicant immunized CD34+ human stem-cell transplant-recipient mice with MMA three days pre-infection. Despite being severely immunocompromised, the vaccine still provided protection against *A. baumannii* bacteremia (FIG. 3F). Applicant also tested several good manufacturing practices (GMP) materials by immunizing mice GMP grade MMA (labeled as G-MMA in the figure) three days pre-infection, and G-MMA provided similar protection as MMA (FIGS. 3G-H).

Experiment 5: Cellular Source of Protection

Figure 4:
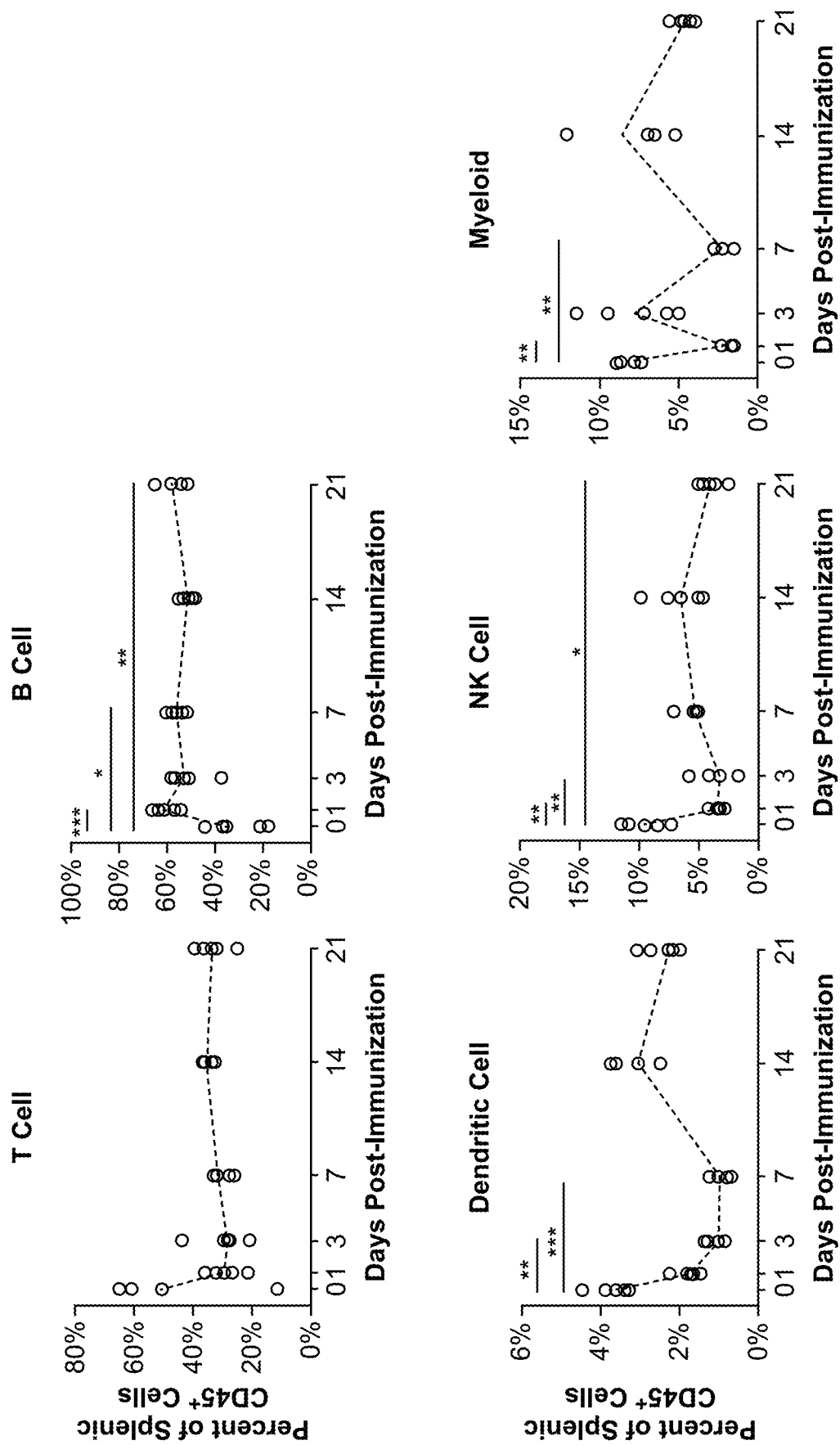
FIG. 4 (8 panels) shows proportions of CD45$^+$ immune cell populations change in response to MMA immunization. Male C3HeB/Fe mice (N=5 per group) were immunized SC as a 0.2 ml suspension in PBS containing MMA (100 μg Mannan, 10 μg MPL, and 0.2 mg Al(OH)$_3$). Splenocytes were harvested pre-immunization or one, three, seven, 14, or 21 days post-immunization, and cell populations were determined by multicolor flow cytometry. Proportion of CD45$^+$ cells that are T cells (TCRβ$^+$), B cells (CD19$^+$), dendritic cells (CD11C$^+$), natural killer (NK) cells (NKp46$^+$CD49b$^+$) and proportion of myeloid cells (CD45$^+$CD11b$^+$) that are neutrophils (Ly6C$^+$Ly6G$^+$), monocytes (Ly6C$^+$Ly6G), and macrophages (Ly6C$^-$Ly6G). Cell population was compared by Kruskal-Wallis test with a $=0.05$. *$p \leq 0.05$, **$p \leq 0.01$ vs Day 0.
Figure 4:
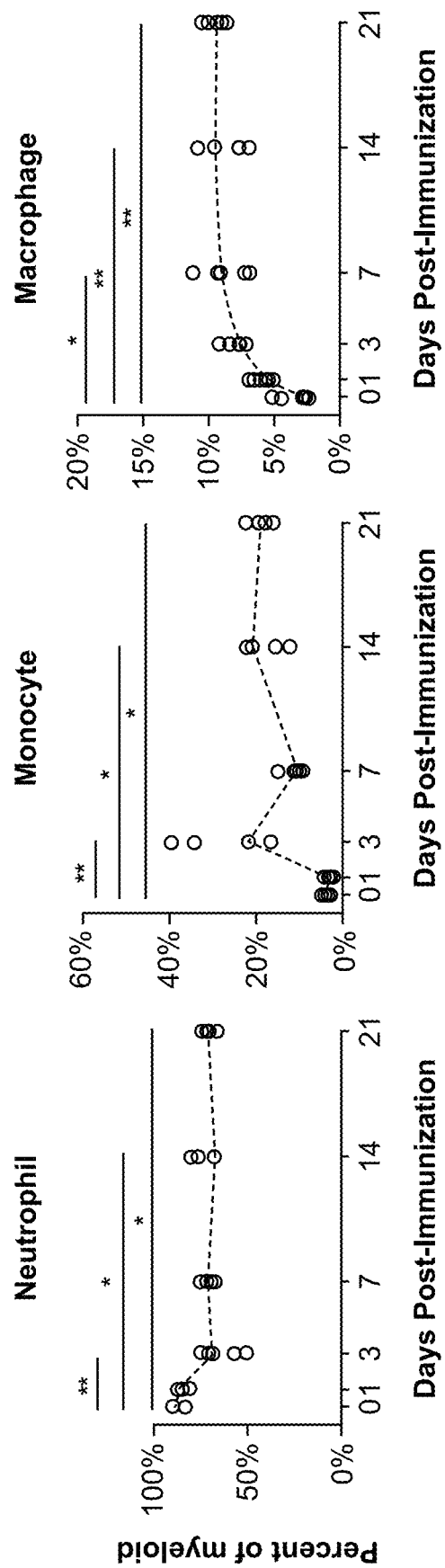

To begin to define the mechanism of protection, Applicant evaluated changes to seven immune cell populations sourced from the spleen of immunized and non-immunized mice. No significant change was observed in the proportion of CD45+ cells that were T cells (FIG. 4). Conversely, the proportion of CD45+ cells that were B cells was elevated for at least three weeks post-immunization (FIG. 4). Dendritic and natural killer (NK) cell populations decreased quickly as a proportion of CD45+ cells, but they reverted to pre-immunization levels by two weeks post-immunization (FIG. 4). No trend was observed in the proportion of CD45+ cells that were of the myeloid lineage (FIG. 4). Nevertheless, there was an immediate change in the proportion of neutrophils, monocytes, and macrophages (FIG. 4). Specifically, the proportion of neutrophils decreased, whereas the proportion of monocytes and macrophages rapidly increased and remained elevated for at least three weeks (FIG. 4).

Figure 5A:
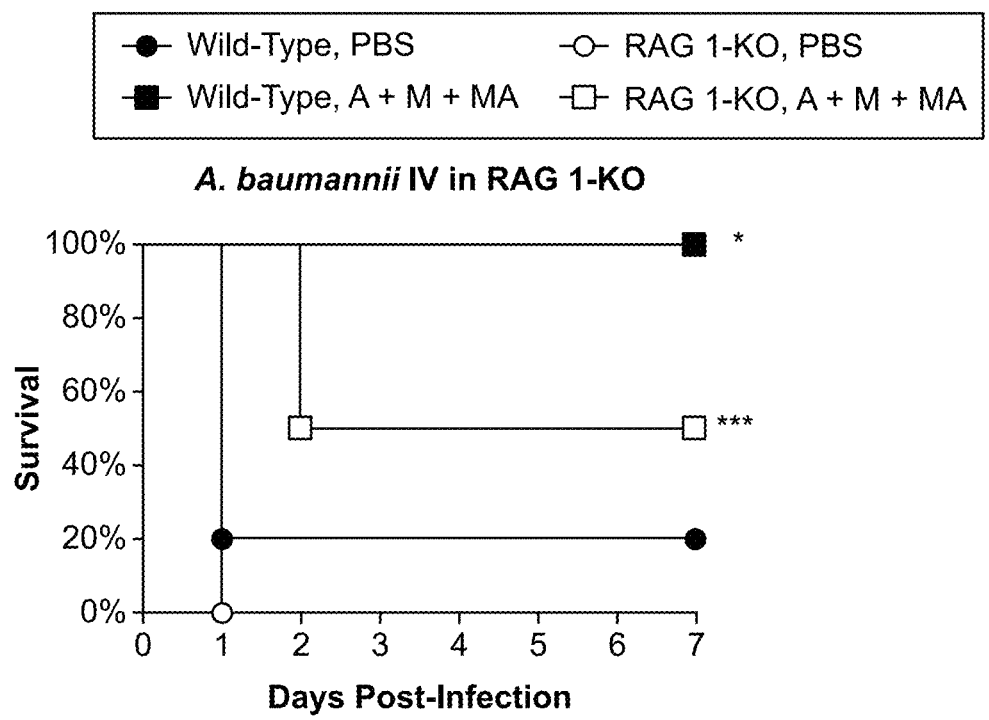
FIGS. 5A-5G show that macrophages are the key to inducing MMA-mediated protection.
Figure 5B:
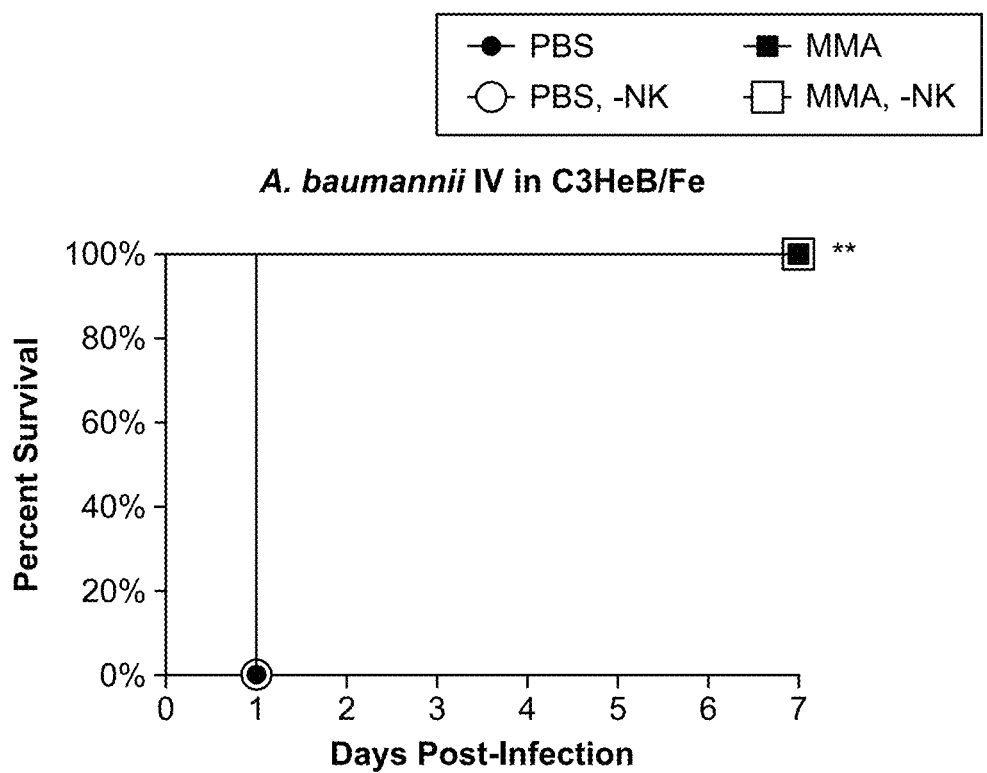
Figure 5C:
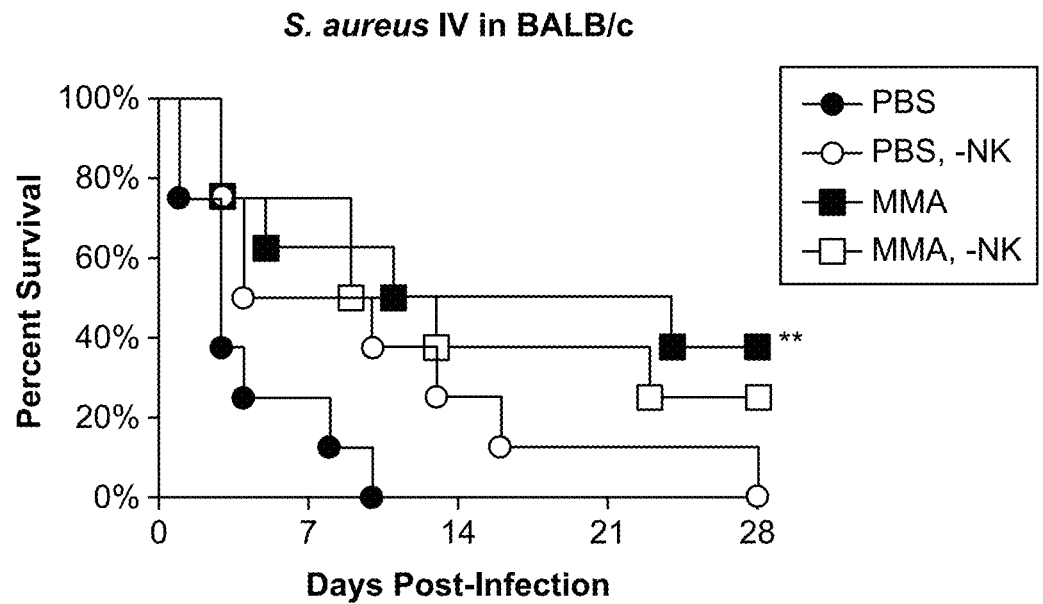
Figure 5D:
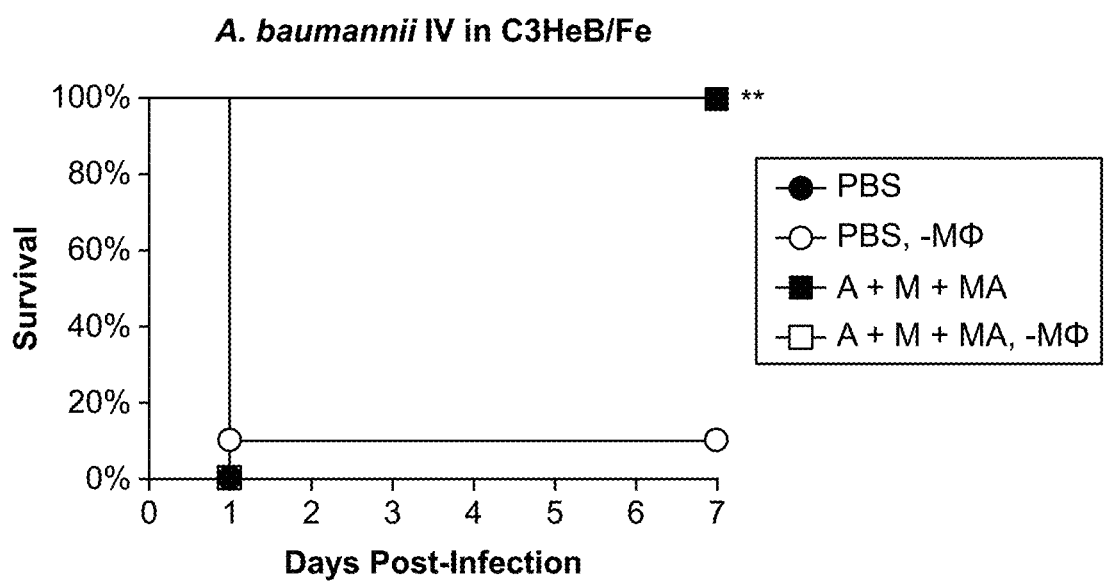
Figure 5E:
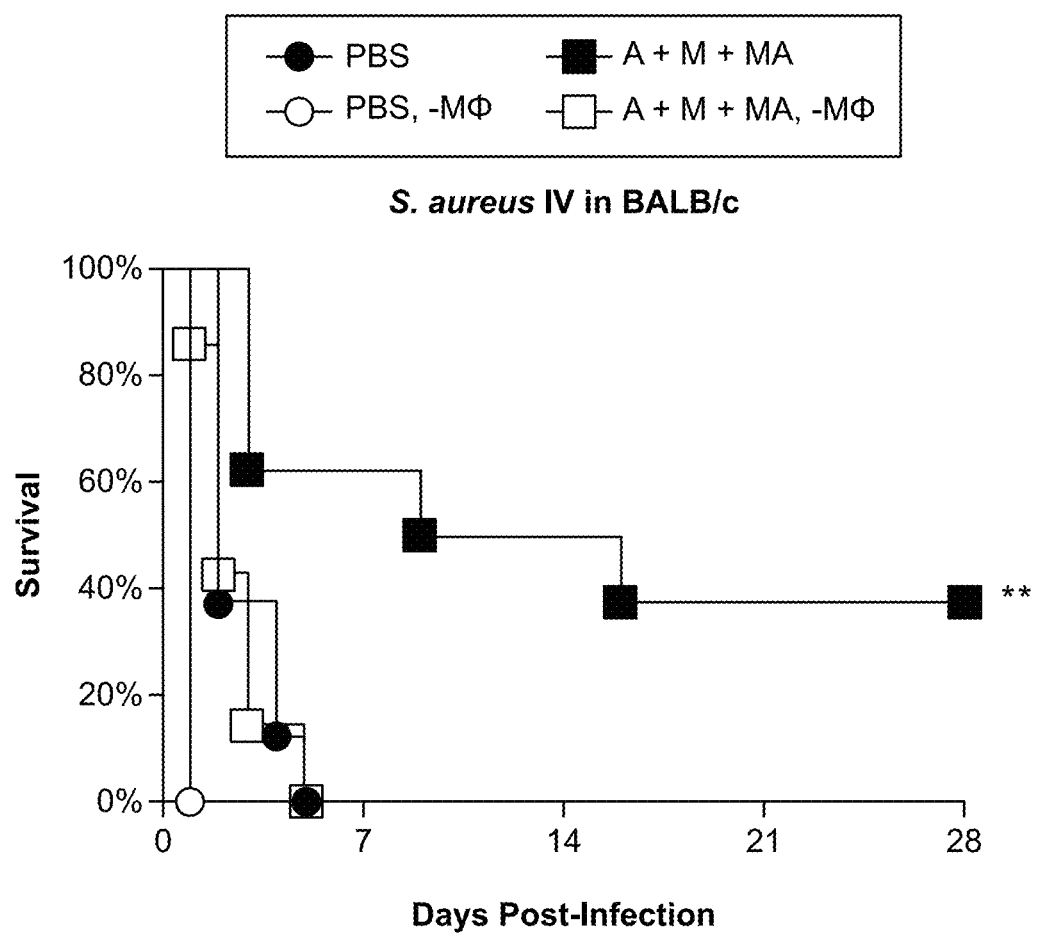

The lack of antibody-mediated immunity (FIG. 3C) and the rapid, overnight induction of protective immunity (FIG. 3D) suggested that the vaccine mediated protection through the innate immune system. Applicant thus hypothesized that only the innate immune system was necessary to provide protection. Recombination activating gene 1 (RAG1) is critical for V(D)J recombination, and mice with nonfunctional RAG1 lack mature B and T lymphocytes (11). To determine if lymphocytes played a role in MMA mediated protection, Applicant immunized wild-type (WT) and RAG1-knockout (RAG1-KO) mice with MMA and challenged them with *A. baumannii* bacteremia three days post-immunization. Even in the absence of mature B and T lymphocytes, the MMA vaccine successfully protected mice from an otherwise lethal infection (FIG. 5A). These results demonstrated that the adjuvants provided short-term protection via innate immune cells, with no participation of lymphocytes, consistent with Trained Immunity (12, 13).

To identify the potential key innate immune cells that provide MMA-mediated protection, Applicant selectively depleted mice of innate immune cells, immunized them with MMA, and then challenged mice three days later. Specifically, neutrophils were depleted with cyclophosphamide, macrophages/monocytes were depleted with liposomal clodronate, and NK cells were depleted with anti-Asialo-GM1 antibody. Immunized mice were able to survive without neutrophils or NK cells, but mice without macrophages succumbed to both S.aureus and A.baumannii infections (FIGS. 5B-F).

Figure 5F:
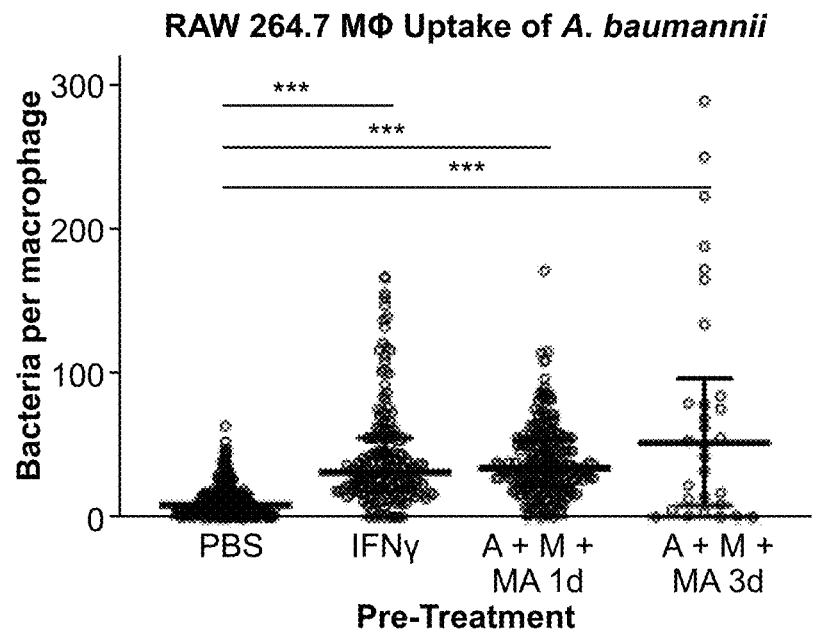
Figure 5G:
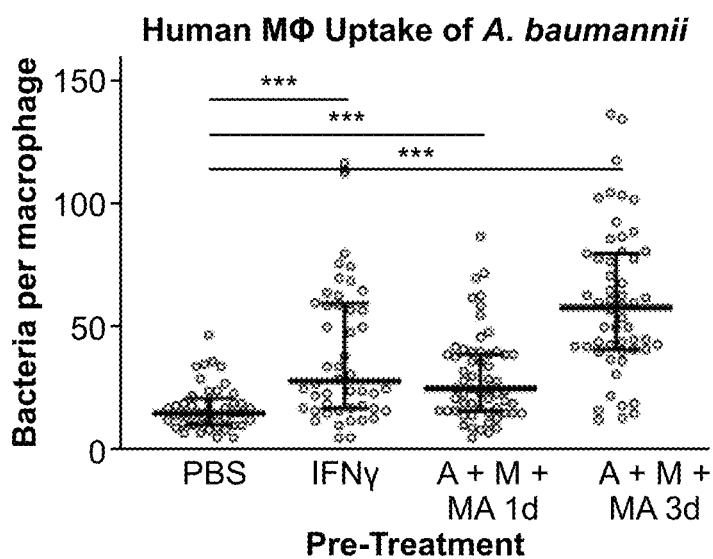

Since macrophages/monocytes proved most important in protecting mice from lethal infection, Applicant then investigated whether MMA could differentiate RAW 264.7 macrophage-like cells and primary human monocyte in vitro by assessing macrophage phagocytosis of A. baumannii after MMA stimulation. Both RAW 264.7 macrophage-like cells incubated with MMA one or three days before uptake assay mediated similar phagocytosis as following the positive control, IFNγ stimulation (FIG. 5F).

Experiment 6: Immunomodulatory Mechanism of Protection

Figure 6A:
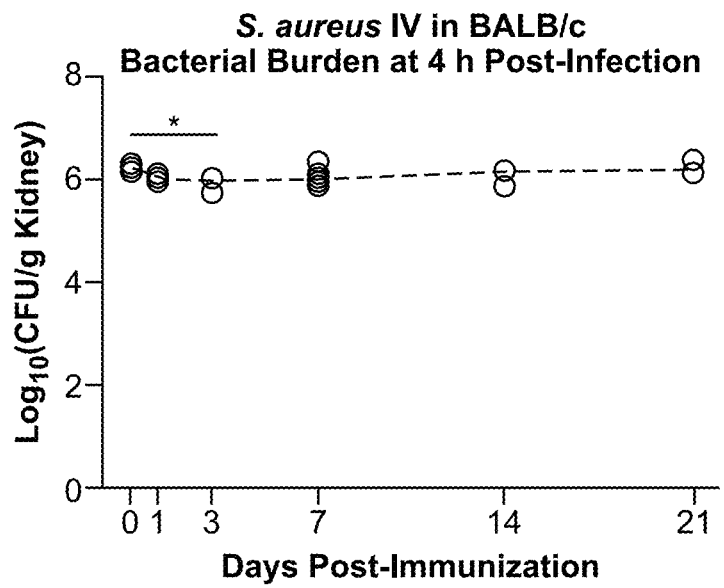
FIGS. 6A-6D show the decrease in pro-inflammatory cytokines after infection in MMA-immunized mice. Mice were immunized SC with a 0.2 ml suspension in PBS containing MMA (100 μg Mannan, 10 μg MPL, and 0.2 mg Al(OH)$_3$) one, three, seven, 14 or 21 days before infection.
Figure 6B:
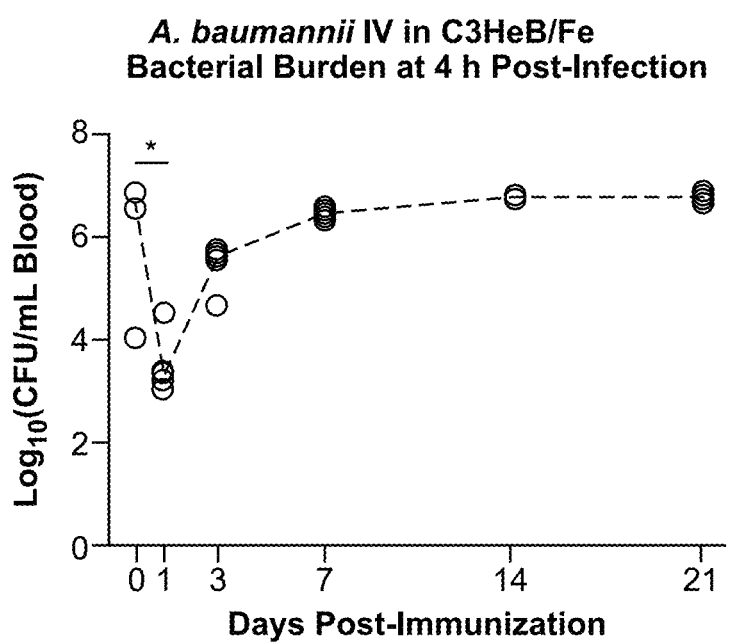

After uncovering the importance of macrophages in conferring protection, Applicant investigated the immunomodulatory properties of the vaccine by evaluating bacterial burden and cytokine profiles of immunized mice. Applicant first analyzed bacterial burden in MMA-immunized mice challenged with lethal S. aureus or A. baumannii bacteremia, four hours post-infection (FIGS. 6A-B). In mice infected with S. aureus, bacterial burden was essentially unchanged, regardless of how long or whether mice were immunized (FIG. 6A). In mice infected with A. baumannii, bacterial burden was significantly lower in mice infected one or three days post-immunization, compared to non-immunized mice (FIGS. 6B). Despite statistically non-significant changes in the bacterial burden of most immunized mice, survival outcomes of immunized mice were significantly improved compared to non-immunized mice (FIGS. 2A-B, FIGS. 3A-B, D-E). These data indicate that a reduction in bacterial burden was not the only driving factor for adjuvant-based protection.

Figure 6C:
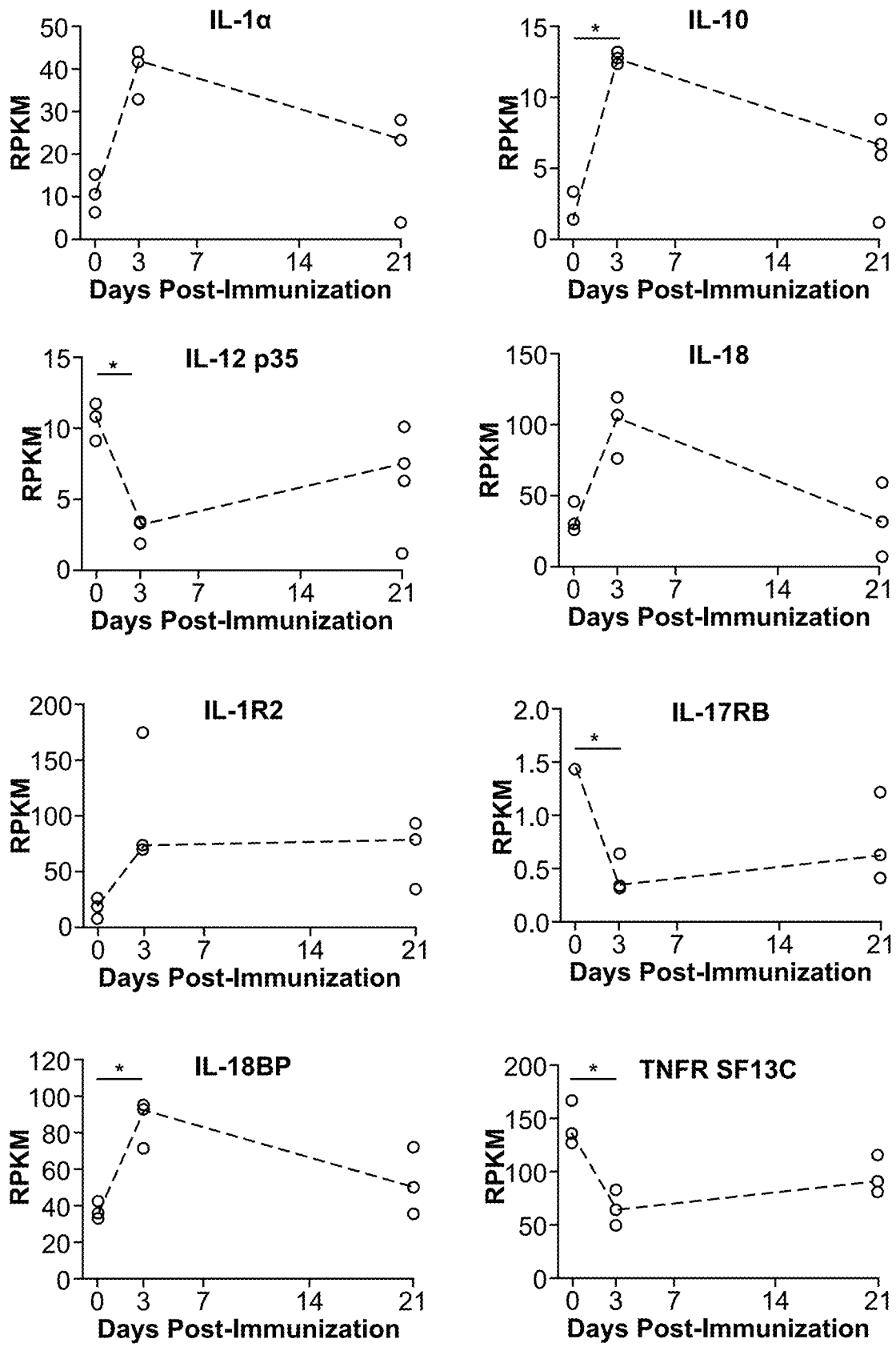
Figure 6D:
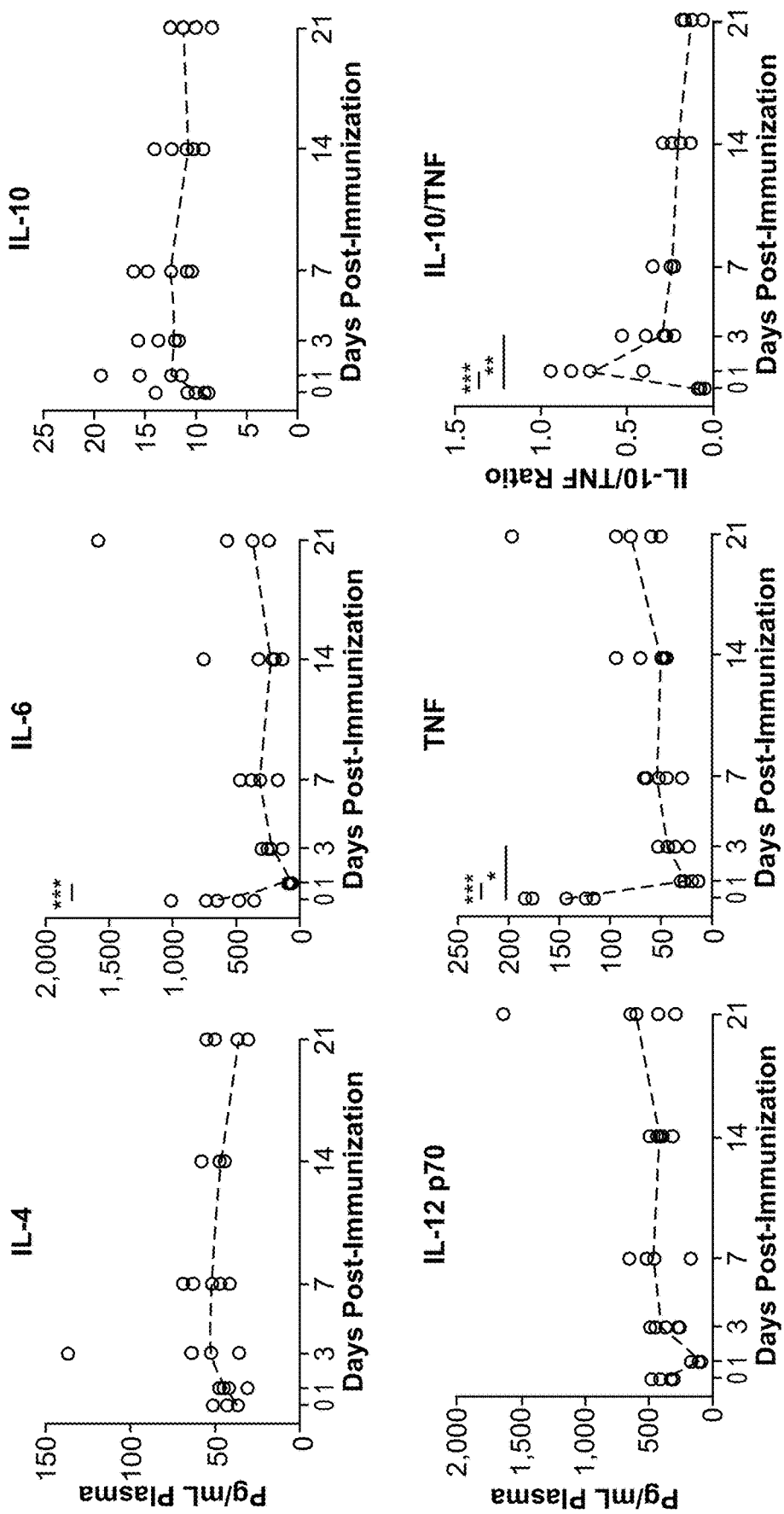
Figure 6D:
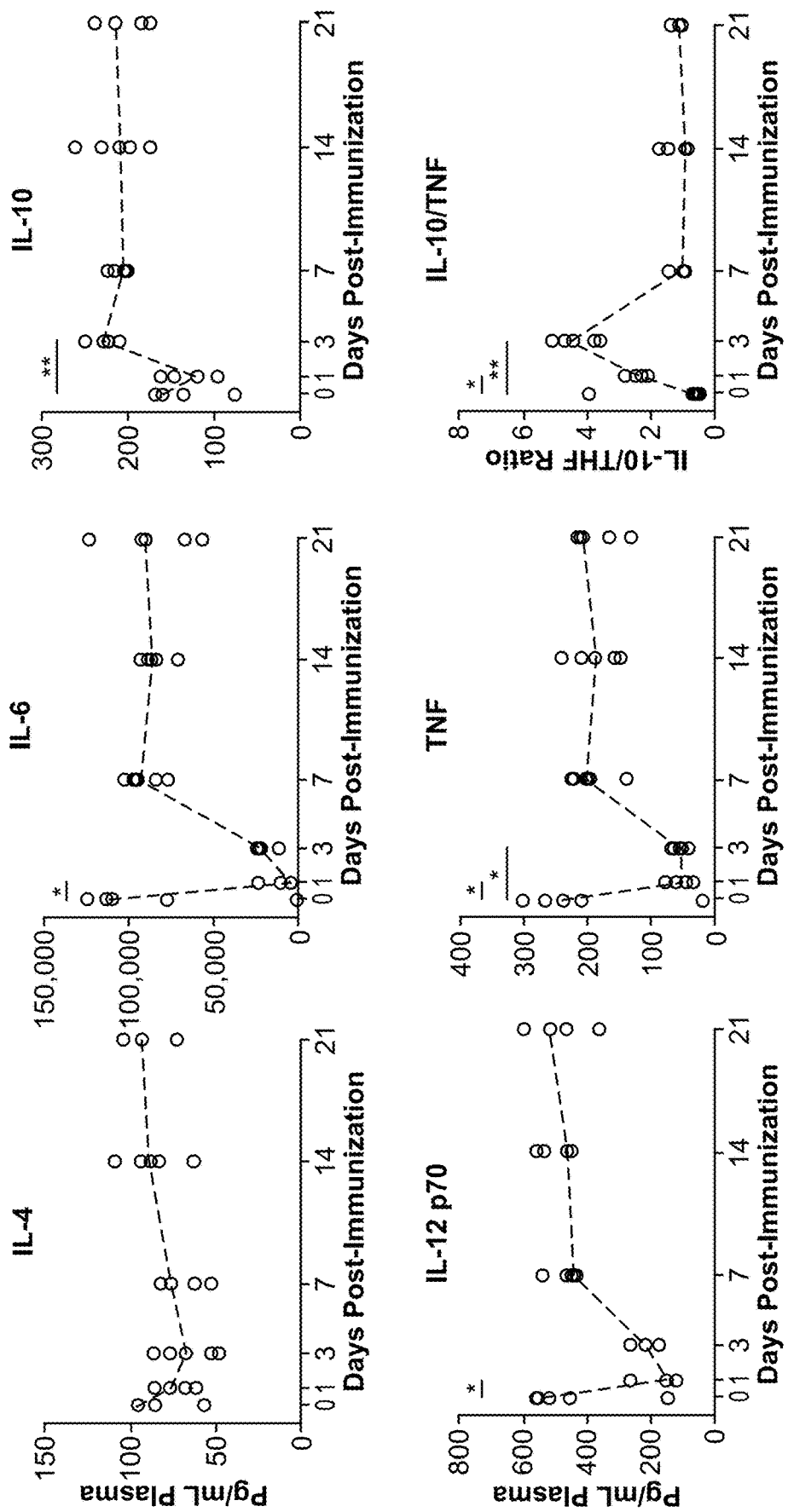
Figure 7:
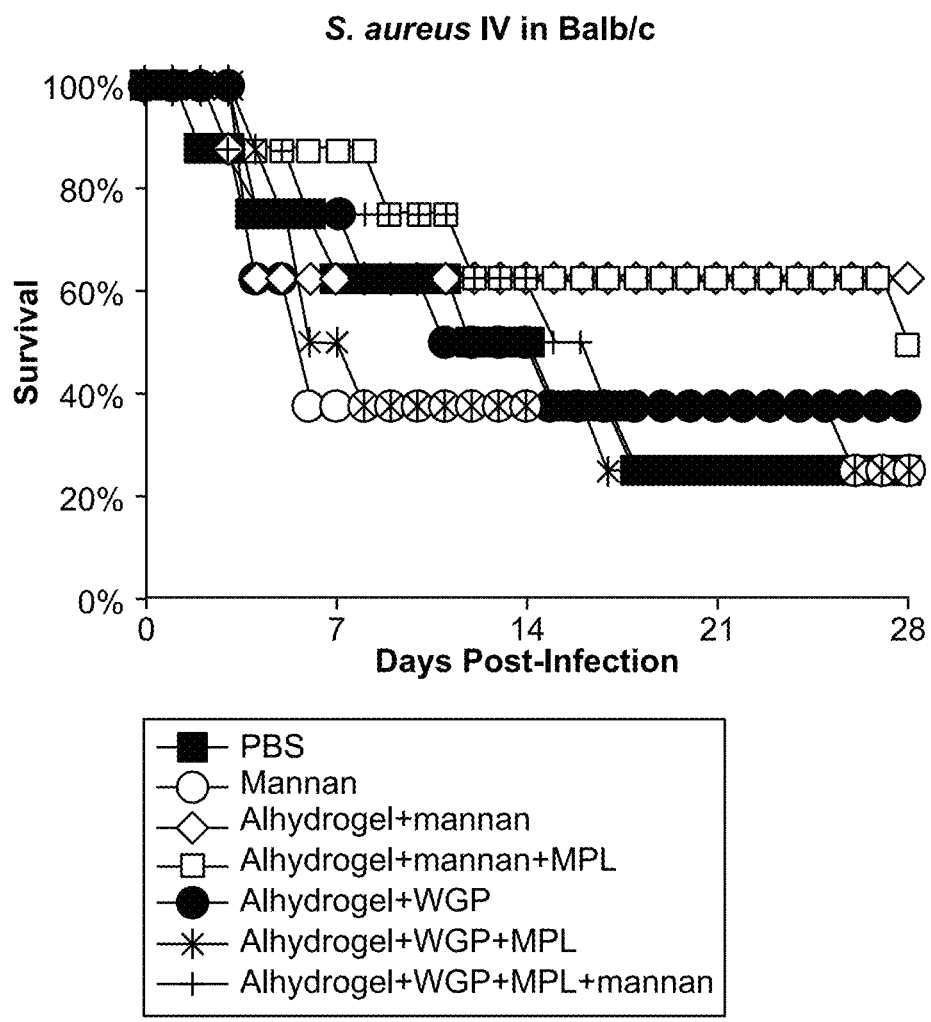
FIG. 7 shows that 0.2 ml SC vaccination with PBS containing the MMA triple vaccine (100 μg Mannan, 10 μg MPL, and 0.2 mg Al(OH)$_3$) is more effective than other vaccine combinations, including double vaccine combinations, the original MWA triple combination (containing Whole Glucan Particles [WGP] instead of Mannan with aluminum hydroxide and MPL), or even quadruple vaccination containing MMA+WGP (mannan, aluminum hydroxide, MPL and WGP). Mice (n=8 mice per group)
Figure 8:
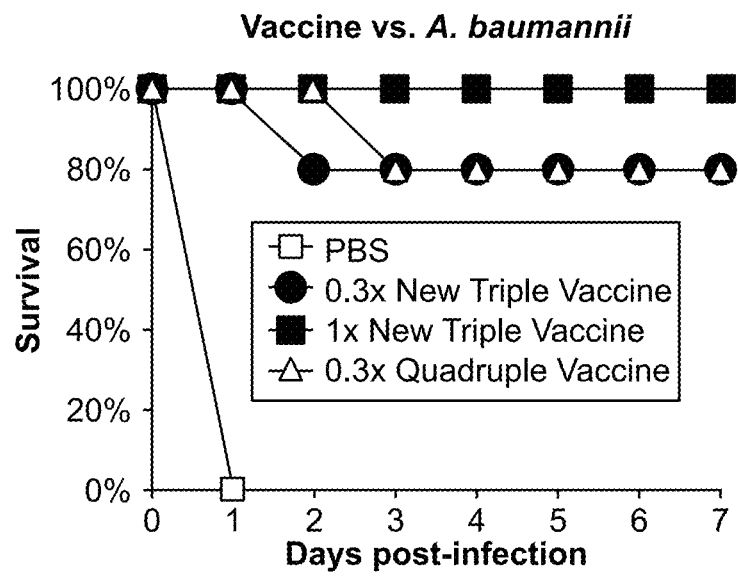
FIG. 8 shows that 0.2 ml SC vaccination with PBS containing the MMA triple vaccine (1×=100 µg Mannan, 10 µg MPL, and 0.2 mg Al(OH)$_3$; 0.3×=30 µg Mannan, 3 µg MPL, 200 µg Al(OH)$_3$) is at least as effective as quadruple adjuvant (MMA+WGP) against *A. baumannii* bloodstream infection (n=5 mice per group).
Figure 9:
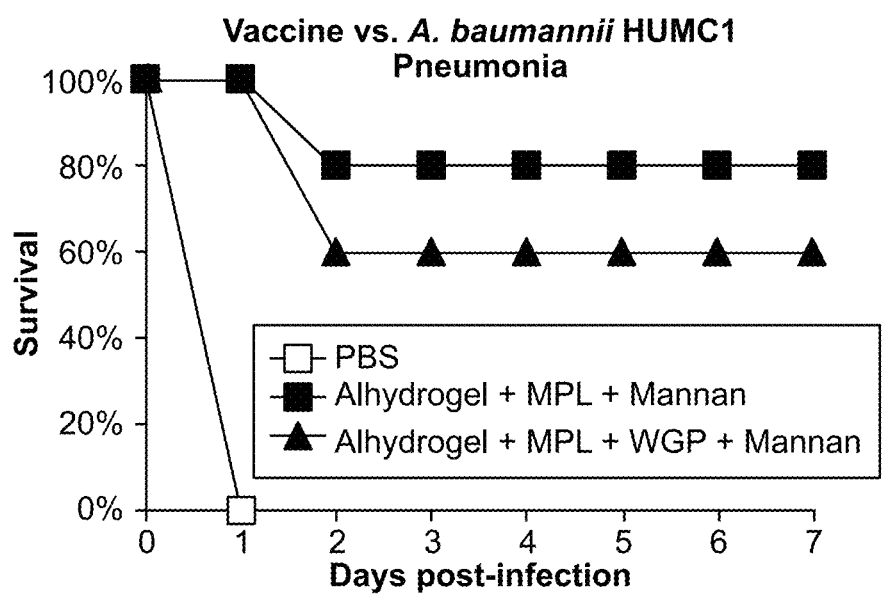
FIG. 9 shows that 0.2 ml SC vaccination with PBS containing the MMA triple vaccine (100 µg Mannan, 10 µg MPL, and 0.2 mg Al(OH)$_3$) is more effective than quadruple vaccine (MMA+WGP) against pneumonia caused by *A baumannii*. (n=5 mice per group).
Figure 10:
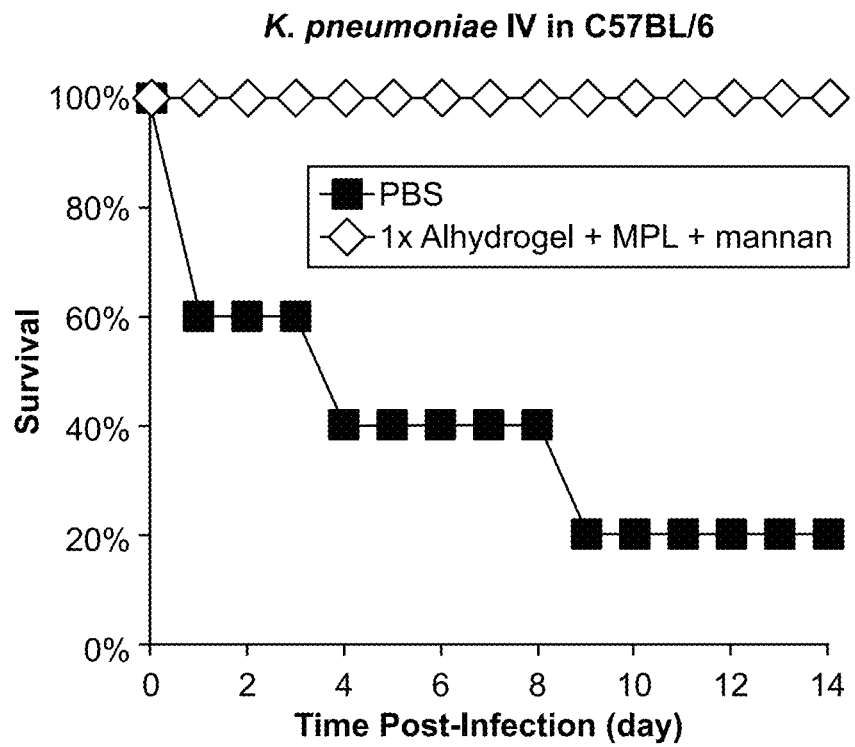
FIG. 10 shows that 0.2 ml SC vaccination with PBS containing the MMA triple vaccine (100 µg Mannan, 10 µg MPL, and 0.2 mg Al(OH)$_3$) protects against PDR *K. pneumoniae*. PDR *K. pneumoniae* KPCKP1 (2×10$^8$ inoculum) in bloodstream infection.
Figure 11:
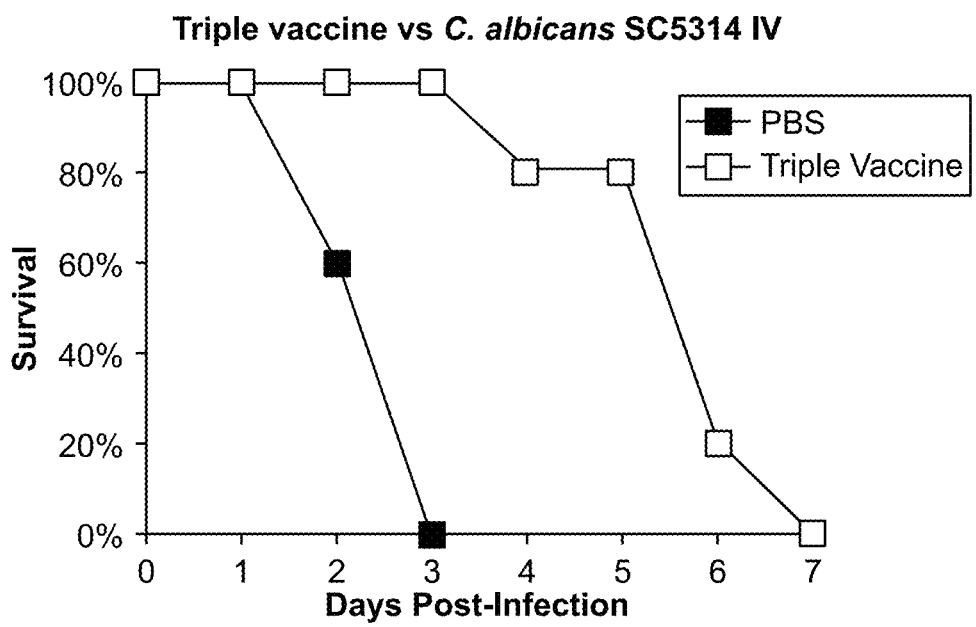
FIG. 11 shows that 0.2 ml SC vaccination with PBS containing the MMA triple vaccine (100 µg Mannan, 10 µg MPL, and 0.2 mg Al(OH)$_3$) protects against *Candida albicans*. Hyper-virulent *C. albicans* SC5314 (2×10$^5$ inoculum) in bloodstream infection was tested. Balb/c mice were vaccinated and infected. Inoculum can be lowered 4-fold from 2×10$^5$ and still result in 100% mortality in unvaccinated mice, so this is an aggressive challenge. N=5 mice per group. P<0.05 vs. phosphate buffered saline.
Figure 12A:
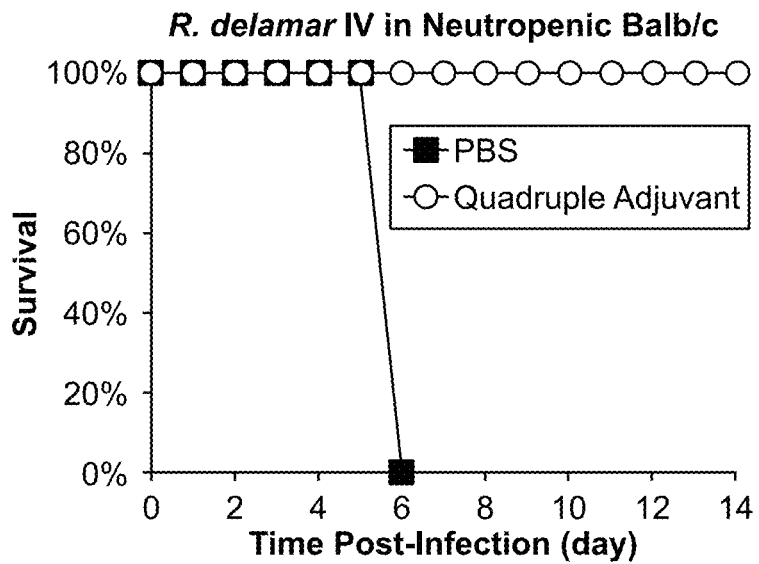
FIGS. 12A and 12B show that 0.2 ml SC vaccination with PBS containing the MMA vaccine (100 µg Mannan, 10 µg MPL, and 0.2 mg Al(OH)$_3$) protects against the fungal disease mucormycosis, caused by *Rhizopus delamar* in neutropenic mice, and was more effective than quadruple vaccine (MMA+WGP). Balb/c mice were made neutropenic with cyclophosphamide, immunized, and infected IV 3 days later with the mold, *Rhizopus delamar*.
Figure 12B:
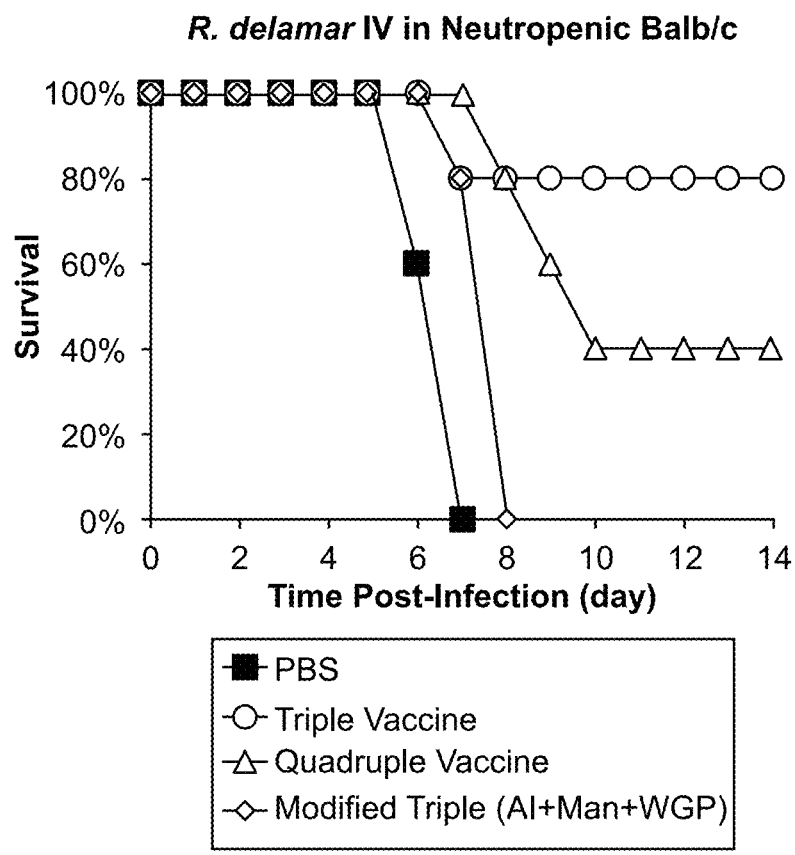
Figure 13:
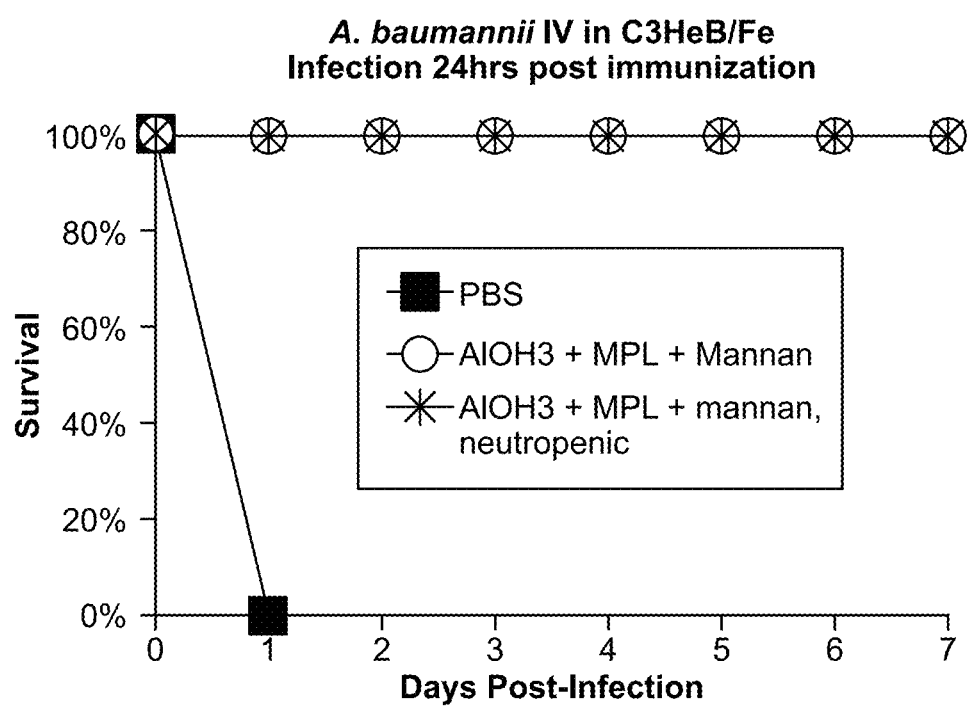
FIG. 13 shows that 0.2 ml SC vaccination with PBS containing the MMA vaccine protects by 24 hours even in neutropenic mice. Hypervirulent *A. baumannii* HUMC1 in bloodstream infection was tested. C3H mice (half made neutropenic/immune compromised with cyclophosphamide at day −3) were immunized at day −1 with 100 µg Mannan, 10 µg MPL, and 0.2 mg Al(OH)$_3$, and infected 24 h later (day 0) with *A. baumannii* HUMC1. *p≤0.05 vs. PBS.
Figure 14A:
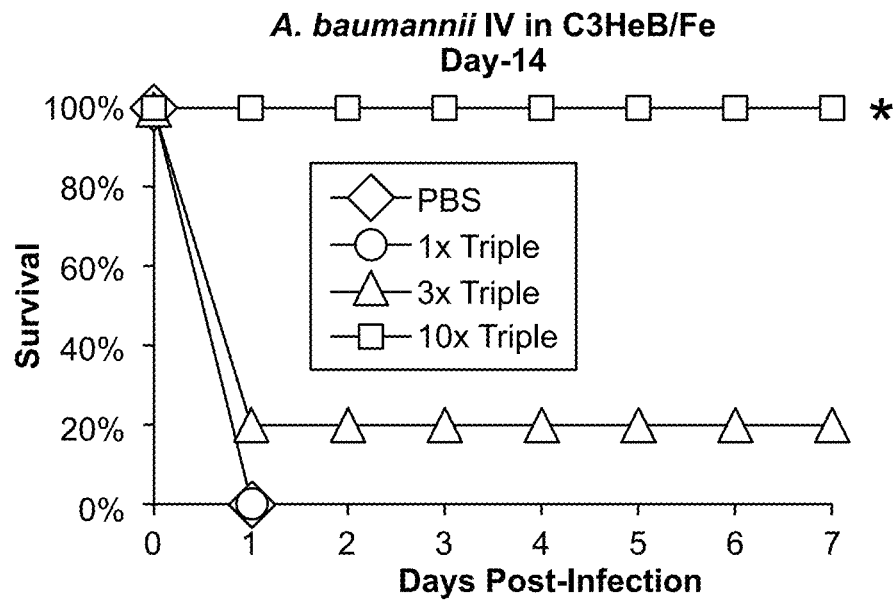
FIGS. 14A and 14B show that higher dose MMA triple vaccine administered SC as a 0.2 ml suspension in PBS protects against *A. baumannii* up to 21 days. HUMC1 (2.9×10$^7$ Inoculum) in bloodstream infection was tested. C3HeB/FeJ mice (n=5/group) were infected IV via the tail-vein with *A. baumannii* HUMC1, 14 days (FIG. 14A) or 21 days (FIG. 14B) after 1×(100 µg Mannan, 10 µg MPL, and 0.2 mg Al(OH)$_3$), 3×(300 µg Mannan, 30 µg MPL, and 0.2 mg Al(OH)$_3$) or 10× dose (1000 µg Mannan, 100 µg MPL, and 0.2 mg Al(OH)$_3$) of the MMA triple vaccine regimen.
Figure 14B:
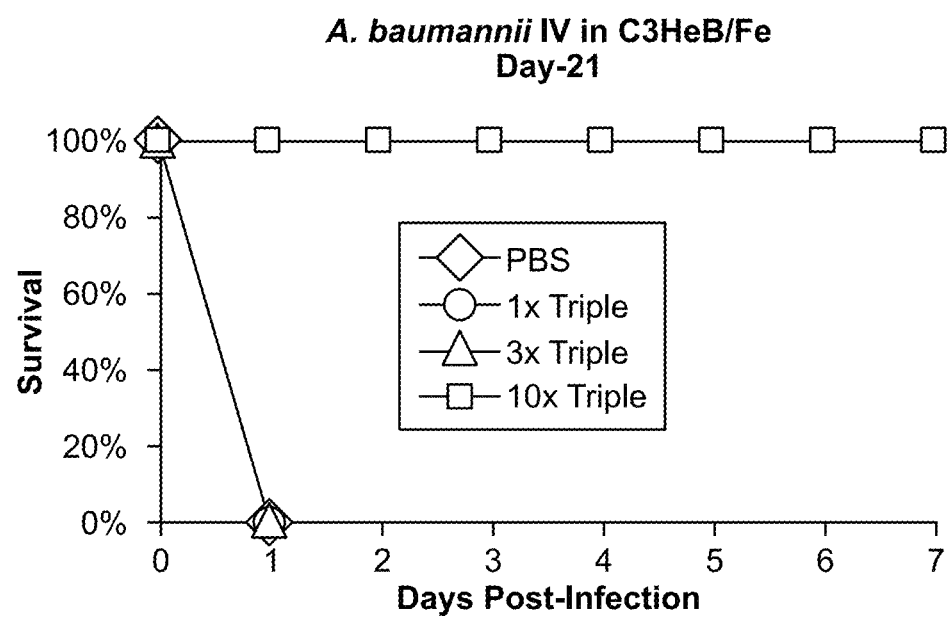
Figure 15A:
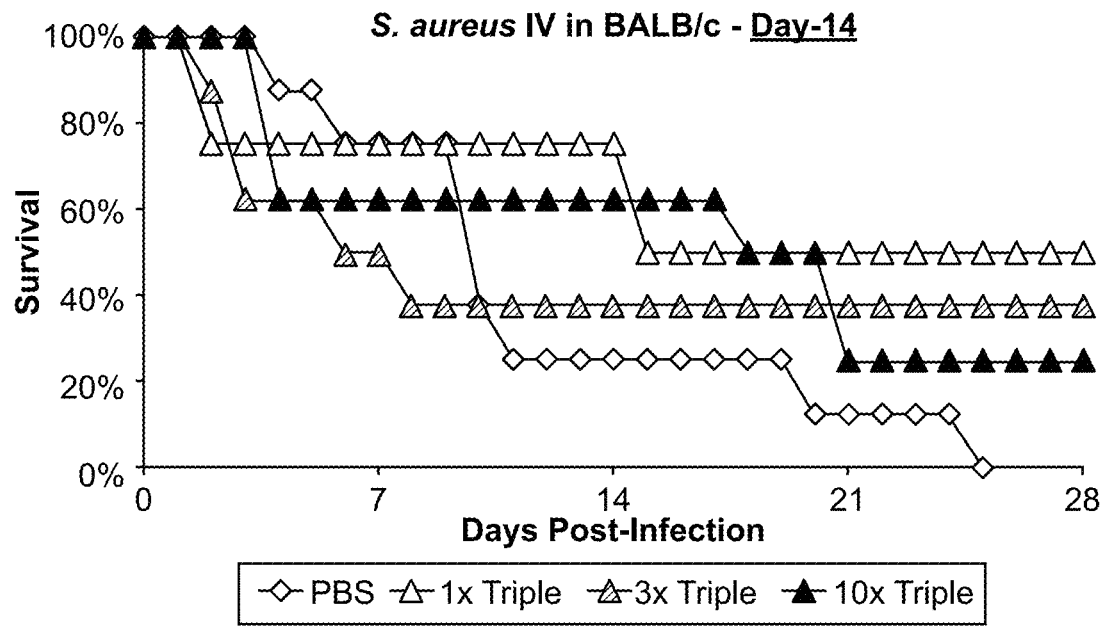
FIGS. 15A and 15B show that higher dose MMA triple vaccine administered SC as a 0.2 ml suspension in PBS protects against *S. aureus* up to 21 days. LAC (2.4×10$^7$ Inoculum) in bloodstream infection were tested. BALB/c mice (n=8/group) were infected IV via the tail-vein with *S. aureus* LAC, 14 days (FIG. 15A) or 21 days (FIG. 15B) after 1×(100 µg Mannan, 10 µg MPL, and 0.2 mg Al(OH)$_3$), 3×(300 µg Mannan, 30 µg MPL, and 0.2 mg Al(OH)$_3$) or 10× dose (1000 µg Mannan, 100 µg MPL, and 0.2 mg Al(OH)$_3$) of the MAA triple vaccine regimen.
Figure 15B:
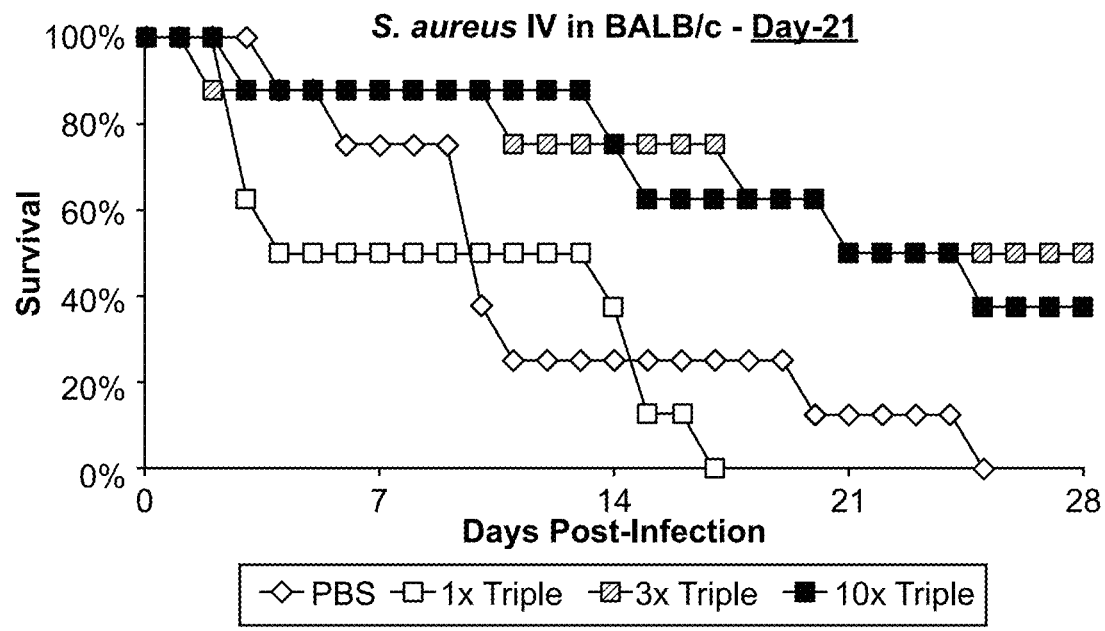
Figure 16:
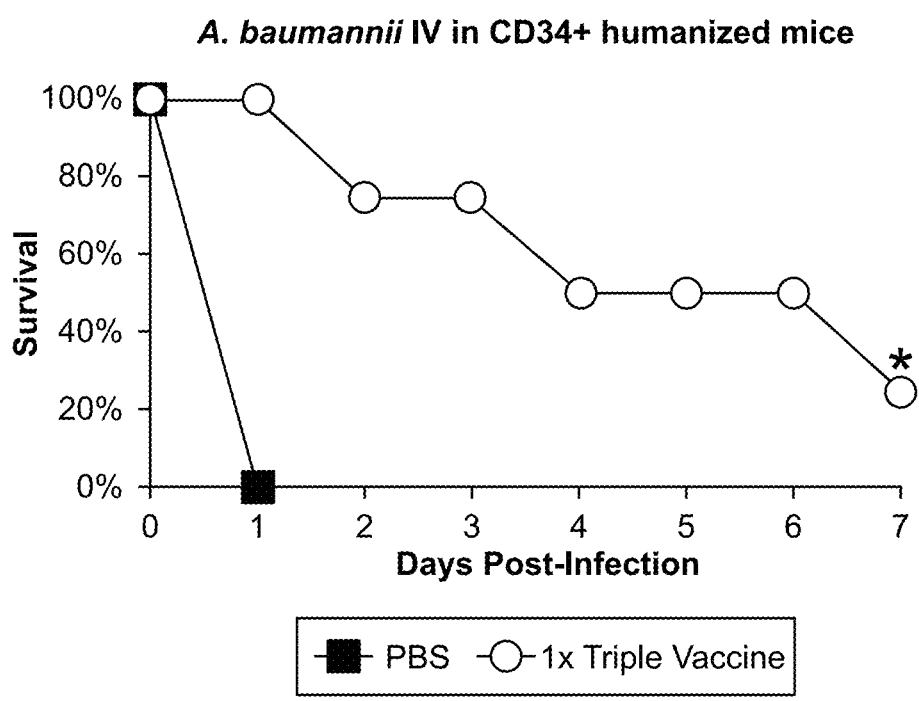
FIG. 16 shows efficacy in humanized mice: CD34+ human stem cell transplants, infected with *A. baumannii*. HUMC1 in bloodstream infection was tested. Human immune stem cell transplanted mice (n=5/group) were infected IV via the tail-vein with *A. baumannii* HUMC1 3 days after 1× dose of the MMA triple vaccine administered SC as a 0.2 ml suspension in PBS (100 µg Mannan, 10 µg MPL, and 0.2 mg Al(OH)$_3$). p≤0.05 vs. control.

Applicant have previously observed that cytokine profiles are a better indicator of survival outcomes than bacterial burden (14). As such, Applicant analyzed cytokines in the plasma of the very same immunized mice challenged with lethal S. aureus or A. baumannii bacteremia four hours post-infection. For both pathogens, immunized mice had lower proinflammatory cytokines (IL-6, IL-12, TNF) and elevated IL-10/TNF ratios that persisted for three weeks (FIGS. 6C-D). This trend was especially pronounced in mice challenged one or three days post-immunization. Several cytokines were below the limit of detection (IFNγ, IL-1β, IL-13, IL-17A) or did not change (IL-4).

Experiment 7: Comparative MMA Vaccine Efficacy

Applicant's MMA triple vaccine was compared to prior art MPL triple vaccine, alone or in combination with MPL+ mannan vaccine. The MPL alone or in combination with mannan is disclosed in WO 2018/089475, incorporated herein by reference.

Briefly the MPL triple vaccine comprises comprising, or alternatively consisting essentially of, or yet further consisting of, an effective amount of each of: an aluminum hydroxide, a mono-phosphoryl lipid (MPL), and whole glucan particles (WGP), with the proviso that the composition does not comprise an antigen effective to induce an immune response against a fungal or bacterial pathogen. In a further aspect, the composition further comprises, or consists essentially of, or consists of an effective amount of a mannan.

Experiments 8 and 9 extend the studies reported in Experiments 1 to 7 (above).

Experiment 8: Discovery and Defining of Vaccine Components

Applicant first explored the contributions of the individual components of the tripartite vaccine to protection against S. aureus bacteremia. Applicant immunized mice with each individual component or dual or triple combinations of $Al(OH)_3$, MPL, and WGP. All mice were then challenged intravenously (IV) with a USA300 clinical blood isolate of MRSA, LAC. Compared to individual ($Al(OH)_3$) and double combinations ($Al(OH)_3$+MPL or $Al(OH)_3$+WGP), a mixture of $Al(OH)_3$, MPL, and WGP (MWA) provided the best protection (FIG. 1A).

To evaluate the impact of a repeat dose on vaccine efficacy, Applicant immunized mice with phosphate-buffered saline (PBS) or MWA. Three weeks later, half of the mice were vaccinated again. Mice were then challenged IV with S. aureus LAC three, seven, or 21 days after the final immunization. For the single-dose recipients, protection against infection persisted for three (log-rank, p=0.02) and seven days (log-rank, p=0.05) after the dose, but had waned by 21 days post-immunization (FIG. 1B). The second dose restored protection for a further three days (log-rank, p=0.02), but not a further seven or 21 days (FIG. 1B).

Since the immunostimulatory components of the MMA vaccine were not specific to S. aureus, Applicant investigated the ability of the vaccine to protect against bacteremia caused by the Gram-negative bacterium, Acinetobacter baumannii. Applicant immunized mice with PBS or MWA and infected them intravenously either three or seven days post-immunization with an extremely drug-resistant ( )CDR), clinical lung and blood isolate of A. baumannii, HUMC1. Groups immunized with MWA were fully protected against otherwise lethal bacteremia (log-rank, p=0.0009) (FIG. 1C).

Similar to S. aureus, Applicant tested whether all three components were necessary to protect against A. baumannii bacteremia. Applicant immunized mice with zero, one, two, or all three components and challenged them three days later with a larger inoculum of A. baumannii, enabling differentiation between the survival benefits conferred on each immunization group. Compared to other groups, MWA provided the greatest protection (log-rank, p=0.0001) (FIG. 1D).

Having established the superiority of MWA, Applicant next considered whether the tripartite vaccine could protect against infections from another common route of infection in hospitalized patients-pneumonia-using Applicant's previously described oropharyngeal aspiration (OA) pneumonia model (7). Despite protecting against bacteremia, MWA did not protect against A. baumannii pneumonia infection (FIG. 1E).

Applicant also assessed the ability of the vaccine to protect against lethal bloodstream infection from Klebsiella pneumoniae, another Gram-negative bacterium. Although no mice survived, immunized groups experienced significantly delayed mortality (log-rank, p=0.001) (FIG. 1F). Finally, Applicant explored the effect of lower doses, finding that reduced doses resulted in reduced efficacy in a dose-dependent manner (FIGS. 1G-1H).

Optimizing the Protein-Free Vaccine with Mannan

Based on prior experience working with a mannosylated protein vaccine (8), we sought to enhance vaccine efficacy by incorporating mannan, an oligosaccharide shown to have immunomodulating properties. Mice were immunized with either a quadruple regimen with in which mannan was added to the MPL+Whole Glucan Particles+aluminum hydroxide (MWA) combination, creating a new quadruple combination (MMWA), or the new triple regimen with mannan replacing WGP, consisting of Mannan+MPL+aluminum hydroxide (MMA). Three days later, mice were challenged with a normally lethal inoculum of MRSA, carbapenem-resistant *A. baumannii*, carbapenem-resistant *K. pneumoniae*, *Rhizopus delemar* (in neutropenic mice), or *Candida albicans*. Overall, the vaccine in which mannan substituted for WGP (MMA) provided superior protection against lethal infections of four of the pathogens, including the neutropenic mouse model of *R. delemar* mucormycosis (FIGS. 17A-17E). Furthermore, in contrast to the vaccine with WGP, which did not protect against *A. baumannii* pneumonia, inclusion of mannan helped confer a dramatic survival advantage in mice infected with *A. baumannii* pneumonia (log-rank, p=0.003) (FIGS. 17F vs 17E) and protect against carbapenem-resistant *P. aeruginosa* pneumonia (FIG. 17G).

Finally, Applicant also tested the vaccine against bacteremia caused by the highly antibiotic resistant bacterium vancomycin-resistant *Enterococcus* (VRE). Because VRE tends to be of lower virulence, an unrealistically high inoculum is required to achieve a lethal dose in immunocompetent mice (i.e. >5×10$^8$ CFU). Applicant therefore evaluated bacterial blood density rather that survival. Mice immunized with MMA had a significantly lower blood bacterial burden than control mice (Mann-Whitney, p=0.04) (FIG. 17H).

Optimization of Vaccine Dosage

Figure 18A:
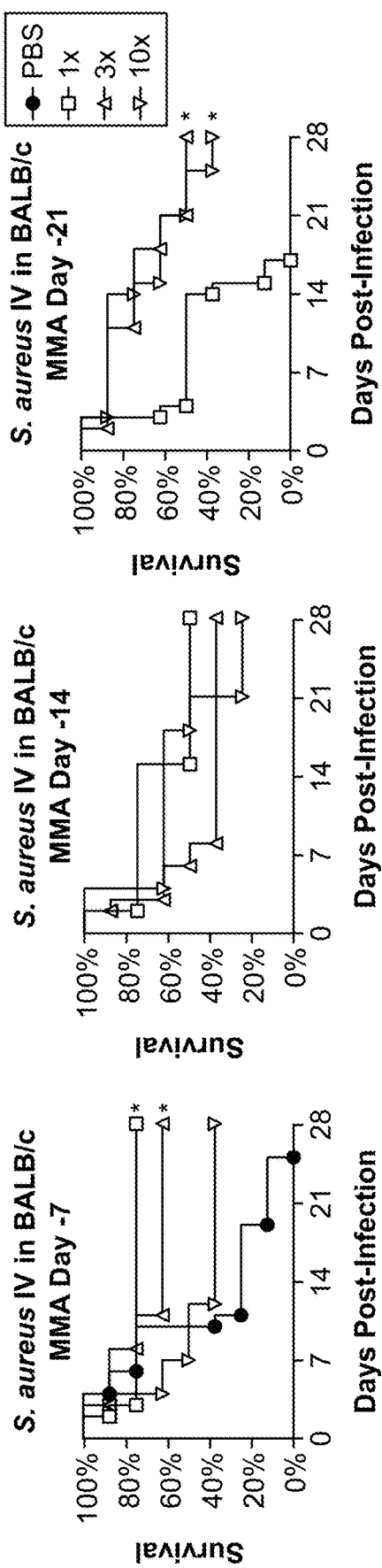

Having established that MMA was superior to prior formulations, and that MMA protection lasted for three days post-immunization, Applicant next sought to evaluate duration of protection and whether increased doses could enhance protection. Applicant immunized mice with three (3×) or ten times (10×) the prior doses of mannan and MPL (3×=300 µg Mannan, 30 µg MPL, 200 µg aluminum hydroxide; 10×=1000 µg Mannan, 100 µg MPL, 200 µg aluminum hydroxide), and challenged them one, two, or three weeks later with lethal *S. aureus* or *A. baumannii* bacteremia. At one and two weeks post-immunization, the smallest dose (1×=100 µg Mannan, 10 µg MPL, 200 µg aluminum hydroxide) provided the greatest protection against MRSA (FIG. 18A). However, the trend flipped at three weeks post-immunization with the largest dose (10×) providing the greatest protection and the lowest dose (1×) performing no better than placebo (FIG. 18A).

Figure 18B:
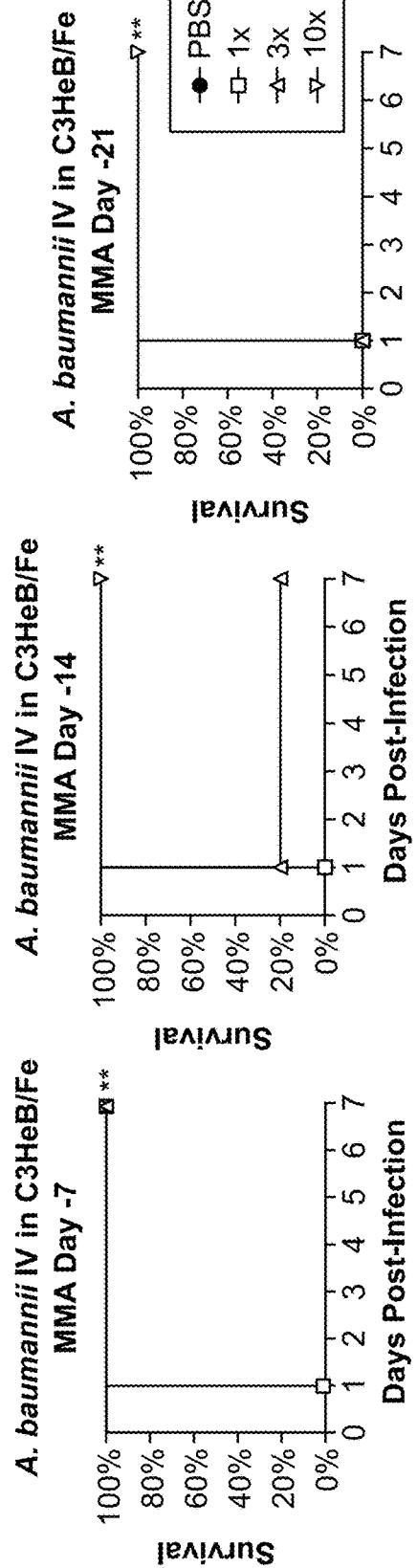

For *A. baumannii* bacteremia, all three doses provided full protection when mice were challenged one week post-immunization (FIG. 18B). However, only the largest dose (10×) provided full protection when mice were challenged two or three weeks post-immunization (FIG. 18B). To be sure that the protective effects were not due to antibody-mediated immunity, Applicant analyzed the plasma of vaccinated mice and confirmed that immunizations did not result in antibodies specific to *A. baumannii* or *S. aureus* (Table 3).

Applicant next sought to define how soon the onset of protection occurs. To this end, Applicant immunized mice with the standard (1×) dose of MMA and challenged them with lethal *S. aureus* or *A. baumannii* bacteremia 24 hours post-immunization. MMA provided either complete protection or protection that was similar to the three-day immunizations (log-rank, p=0.005 *S. aureus* and p=0.003 *A. baumannii*) (FIG. 17A vs FIG. 18C and FIG. 17B vs FIG. 18D).

To assess its translatability to humans, mice were immunized that had undergone whole-body irradiation followed by CD34+human stem-cell transplantation with MMA three days prior to infection (9, 10). Despite being severely immunocompromised, the vaccine still provided considerable protection against *A. baumannii* bacteremia (log-rank, p =0.008) (FIG. 18E). To support potential future clinical use in humans Applicant also tested Good Manufacturing Practice (GMP)-compliant Al(OH)$_3$ and MPL and Good Laboratory Practice (GLP)-compliant mannan by immunizing mice with GMP/GLP-grade MMA (G-MMA) three days prior to infection. The GMP/GLP-grade material provided the same protection as the non-GMP/GLP-grade material (log-rank, p=0.004 *S. aureus* and p=0.003 *A. baumannii*) (FIGS. 18F-18G).

Cellular Source of Protection

Figure 19:
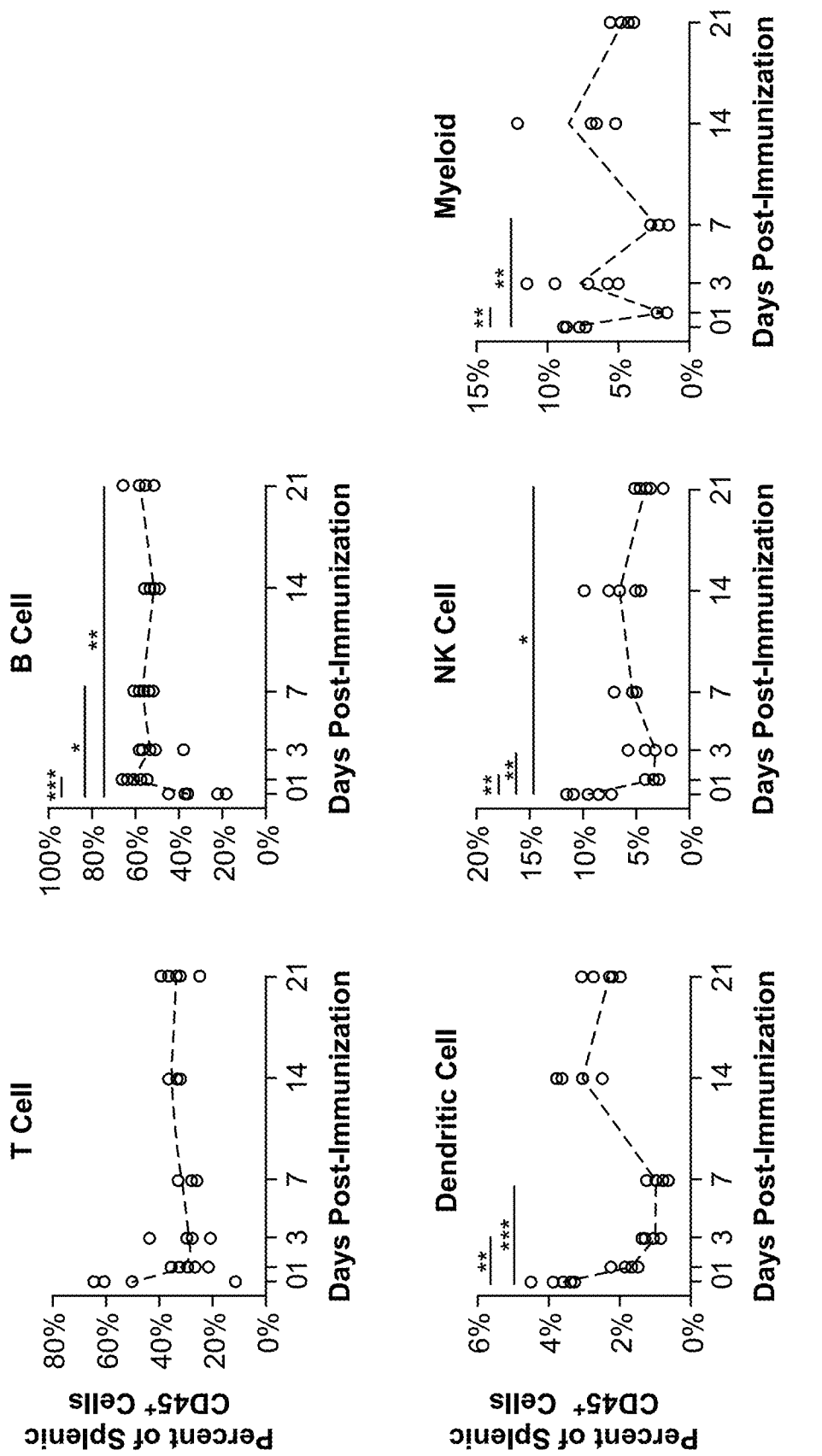
FIG. 19 (8 panels) CD45$^+$ immune cell population changes in response to MMA immunization. Male C3HeB/Fe mice (N=5) were immunized SC with a 0.2 ml suspension in PBS containing MMA (100 µg Mannan, 10 µg MPL, and 0.2 mg Al(OH)$_3$). Splenocytes were harvested from naïve mice (Day 0) and mice immunized one, three, seven, 14, or 21 days prior. Proportion of CD45$^+$ cells that are T cells (TCRβ$^+$), B cells (CD19$^+$), dendritic cells (CD11C$^+$), natural killer (NK) cells (NKp46$^+$CD49b$^+$) and proportion of myeloid cells (CD45$^+$CD11b$^+$) that are neutrophils (Ly6C$^+$Ly6G$^+$), monocytes (Ly6C$^+$Ly6G), and macrophages (Ly6C$^-$Ly6G). Cell population was compared by Kruskal-Wallis test with α=0.05. *p≤0.05, p≤0.01, and *p≤0.001 vs naïve mice (0 day post-immunization).
Figure 19:
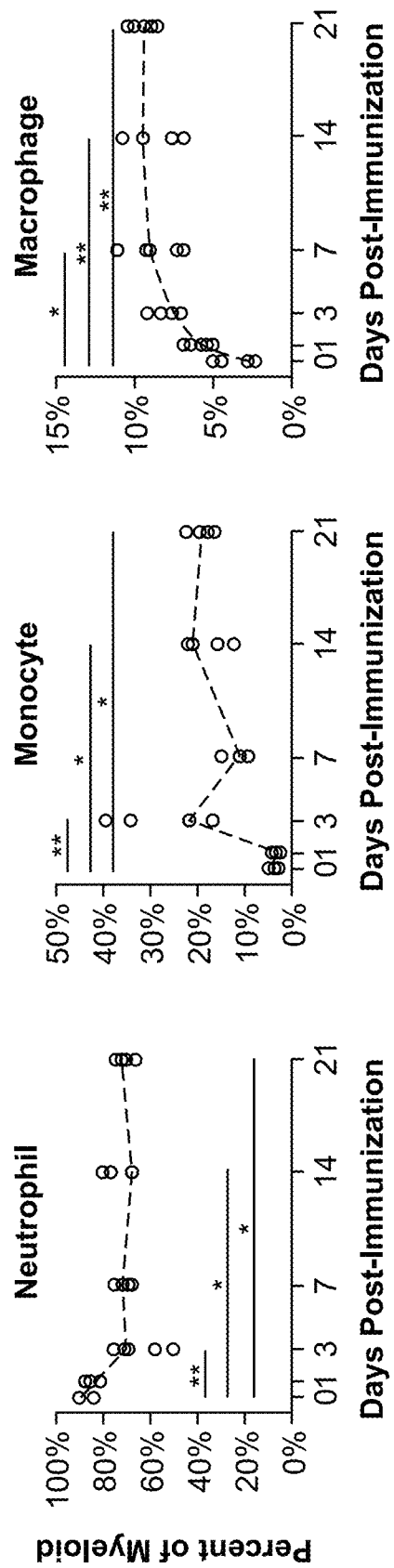

To begin to define the mechanism of protection, Applicant evaluated changes over a 21-day period following immunization in eight immune cell populations sourced from the spleens of immunized and non-immunized mice: T cells, B cells, dendritic cells, NK cells, myeloid cells, neutrophils, monocytes, and macrophages. No significant change was observed in the proportion of CD45$^+$ cells that were T cells (FIG. 19). Conversely, the proportion of CD45$^+$ cells that were B cells was elevated by the first day post-immunization and persisted for at least three weeks (FIG. 19). Dendritic and natural killer (NK) cell populations decreased proportionately by the first day post-immunization as a proportion of CD45$^+$ cells, beginning to increase by three to seven days post-immunization (FIG. 19). No trend was observed for the change in proportion of CD45$^+$ cells that were of the myeloid lineage (FIG. 4). However, by the first day post-immunization there was a change in the proportion of myeloid cell types, including neutrophils, monocytes, and macrophages (FIG. 19). Specifically, the proportion of neutrophils decreased, remaining below baseline for at least three weeks, as the proportion of monocytes and macrophages increased (FIG. 19).

The lack of antibody-mediated immunity (Table 3) and the rapid, <24 h induction of protective immunity (FIG. 18C-18D) suggested that the vaccine mediated protection through the innate immune system rather than through adaptive immunity. Applicant thus hypothesized that only the innate immune system was necessary to provide protection. Recombination activating gene 1 (RAG1) is critical for V(D)J recombination, and mice with nonfunctional RAG1 lack mature B and T lymphocytes, consistent with a Severe Combined Immunodeficiency (SCID) disorders (11-14). To determine if lymphocytes played a role in protection mediated by MMA, Applicant immunized wild-type and RAG1-knockout (RAG1-KO) mice with MMA and challenged them with *A. baumannii* bacteremia three days post-immunization. Even in the absence of B and T lymphocytes in the RAG1-KO mice, the MMA vaccine successfully protected them from an otherwise lethal infection (log-rank, p=0.0009 RAG 1-KO, PBS vs RAG 1-KO, MMA) (FIG. 20A). Thus, the vaccine does not induce protection via T and/or B lymphocytes, as traditional vaccines do.

Figure 20D:
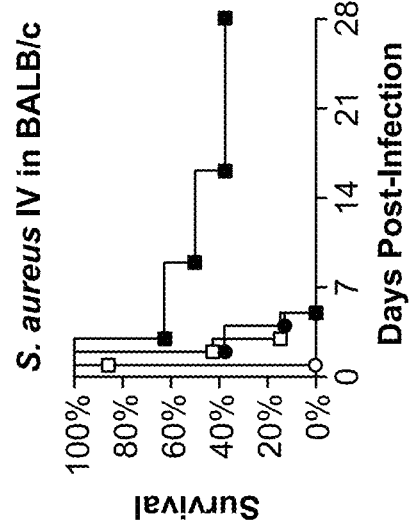
Figure 20E:
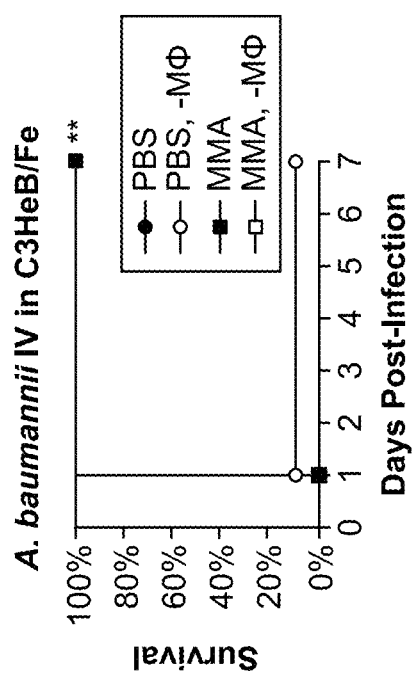

Applicant therefore hypothesized that innate immune cells were essential in protection mediated by MMA. To identify the innate immune cell type(s) essential in MMA medicated protection, Applicant immunized mice them with MMA, and selectively depleted mice of their NK cells, or monocytes/macrophages as studies have shown that NK cells, monocytes, and macrophages are key to inducing trained immunity (15-17). Depletion of NK cells partially ablated protective efficacy of the vaccine against *S. aureus*, but not *A. baumannii*, bacteremia (log-rank, p=0.003), but not *S. aureus* bacteremia (FIGS. 20B-20C). Depleted of monocytes and macrophages completely ablated vaccine protection against both *S. aureus* and *A. baumannii* bacteremia (FIGS. 20D-20E).

Figure 20F:
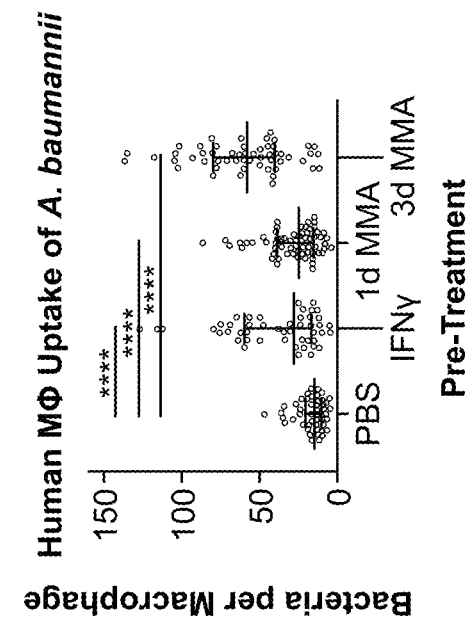
Figure 20G:
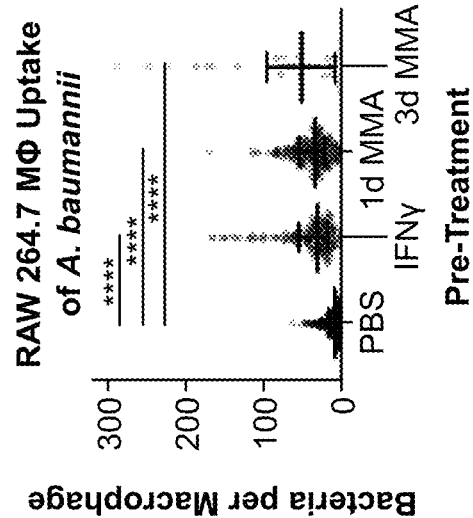

Applicant then investigated whether MMA could activate murine macrophage-like RAW 264.7 cells in vitro and primary human monocytes ex vivo in a manner similar to interferon-γ (IFNγ), by measuring macrophage uptake of *A. baumannii*. For both cell types, one day of stimulation with MMA resulted in phagocytosis at least as effectively ash IFNγ stimulation (Kruskal-Wallis, PBS vs MMA 1 day p≤0.0001 RAW 264.7 and p=0.006 primary human monocytes) (FIGS. 20F-20G).

Immunomodulatory Mechanism of Protection

Figure 22A:
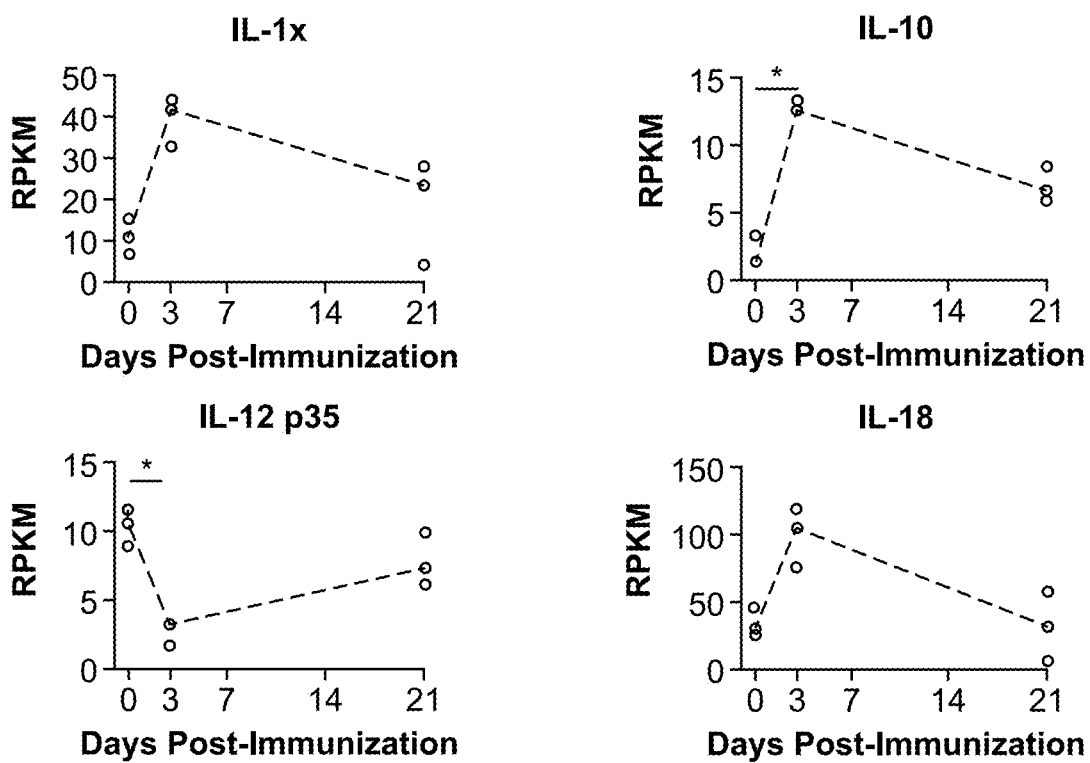
Figure 22B:
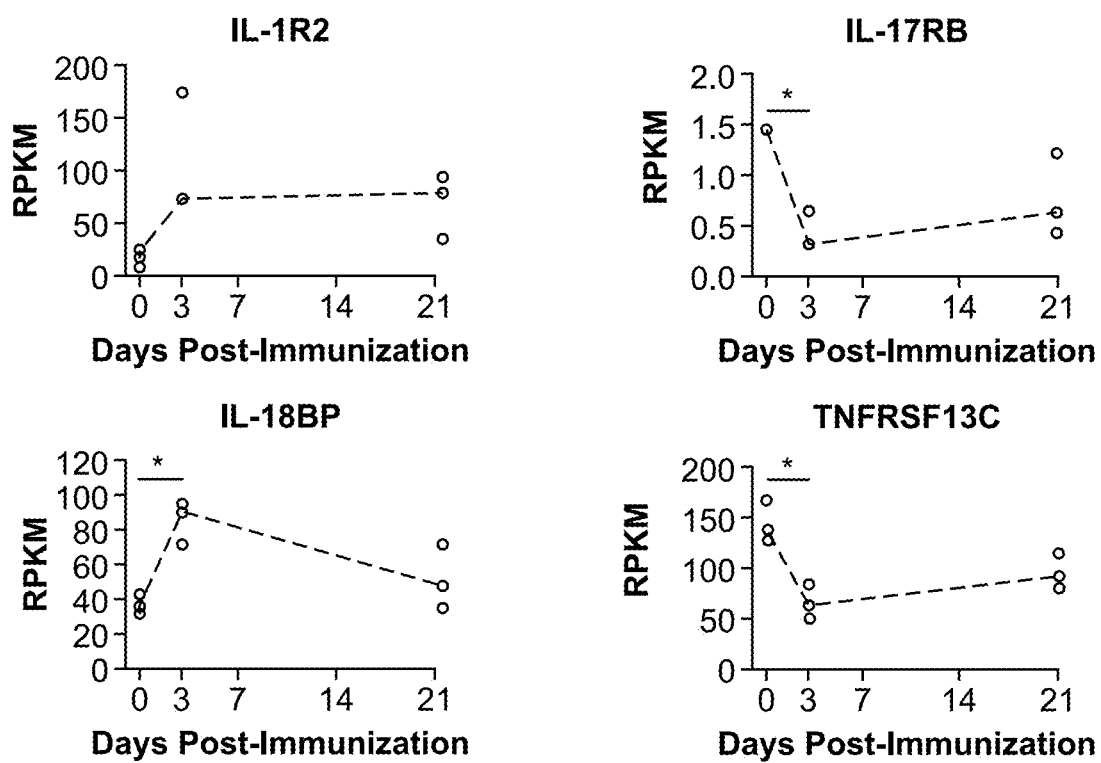

Having established the importance of monocytes and macrophages, Applicant investigated their immunomodulatory properties by evaluating cytokine-related gene expression, bacterial burden, and cytokine profiles in mice immunized with MMA, before and after being infected with *S. aureus* or *A. baumannii* bacteremia. Initially, Applicant attempted to analyze cytokine concentrations in the plasma of immunized mice. However, cytokines (IFNγ, TNF, IL-113, IL-4, IL-6, IL-10, IL 12 p70, IL-13, IL-17A) were below the limit of detection. Applicant then assessed cytokine-associated gene expression, and found that three days post-immunization mice had lower expression of the genes encoding the pro-inflammatory cytokines IL-12 p35 (Kruskal-Wallis, p=0.02), IL-17RB (Kruskal-Wallis, p =0.03), and TNFRSF 13C (Kruskal-Wallis, p=0.02), as well as higher expression of the anti-inflammatory cytokine-associated genes IL-10 (Kruskal-Wallis, p=0.02) and IL-18BP (Kruskal-Wallis,p=0.03). IL-la and IL-1R2, both associated with pro-inflammatory cytokine IL-1, also increased in immunized mice but were not statistically significantly different (FIGS. 22A-22B).

Figures 21A, 21B:
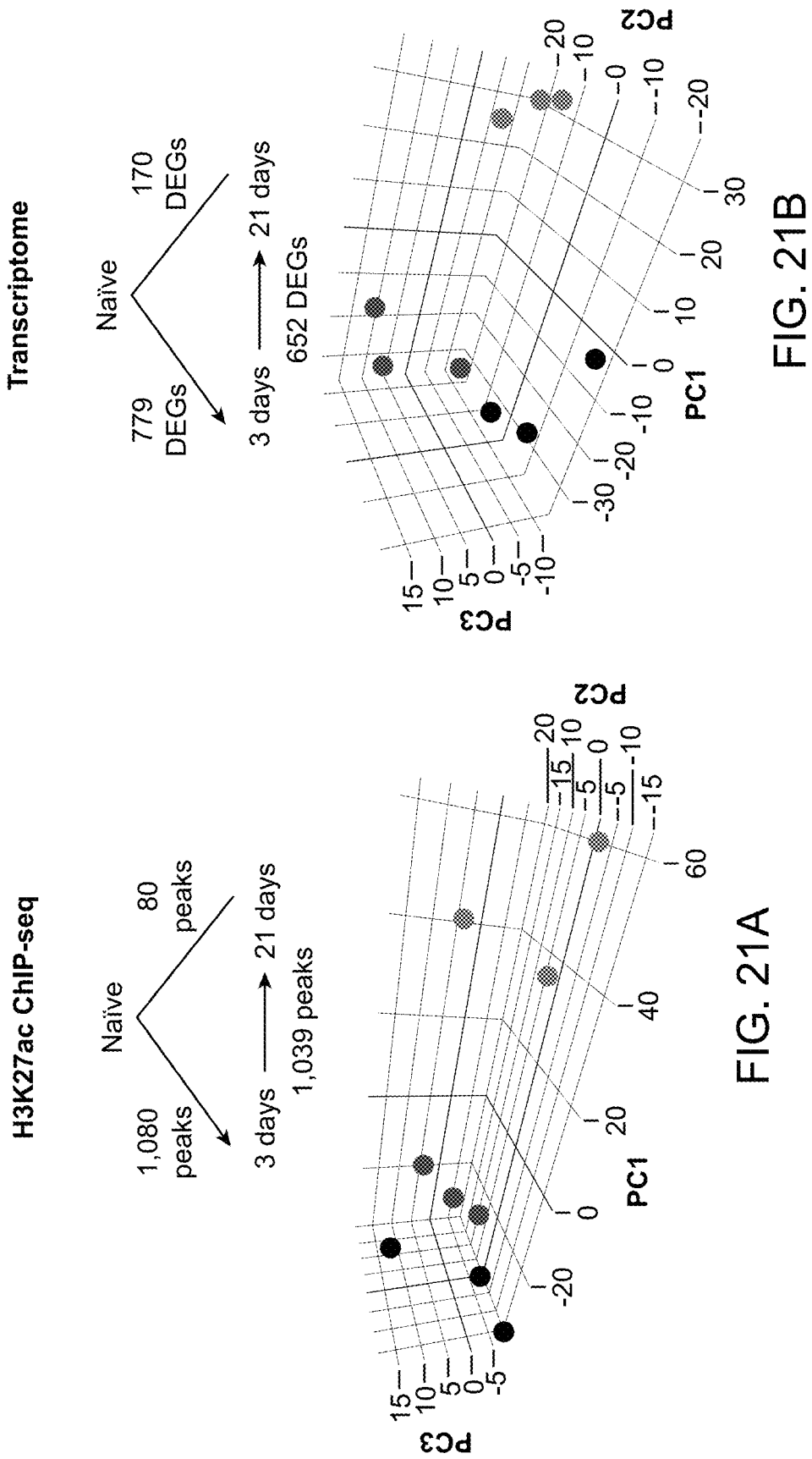
FIGS. 21A-21D Induction of epigenetic reprograming resulted in gene expression changes.
Figures 21C, 21D:
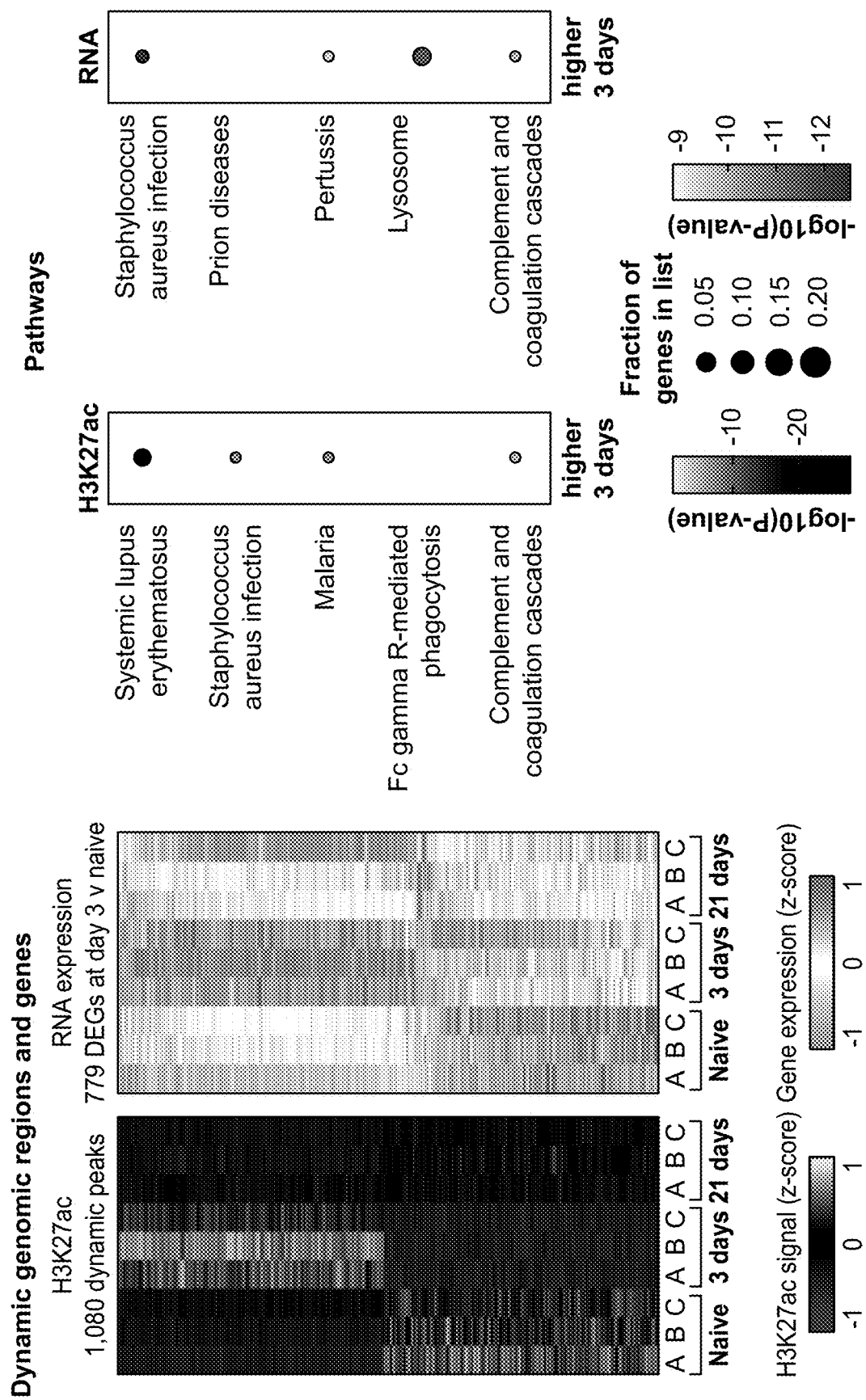

Applicant then analyzed bacterial burden in immunized mice challenged with lethal *S. aureus* or *A. baumannii* bacteremia, four hours post-infection (FIGS. 22C-22D). In mice infected with *S. aureus*, changes in bacterial burden were small, regardless of whether mice had been immunized or how long they had been immunized (FIG. 21C). In mice infected with *A. baumannii*, bacterial burden was significantly lower when infected one day post-immunization, compared to non-immunized mice (FIG. 22D). Despite bacterial burden not being statistically significantly different between most immunized mice compared to naïve mice, survival outcomes significantly improved for immunized mice (FIG. 22C vs FIG. 18A & FIG. 18C, FIG. 22D vs FIG. 18B & FIG. 18D). These data indicated that a reduction in bacterial burden was not the only driving factor for vaccine-mediated protection.

Figure 22E:
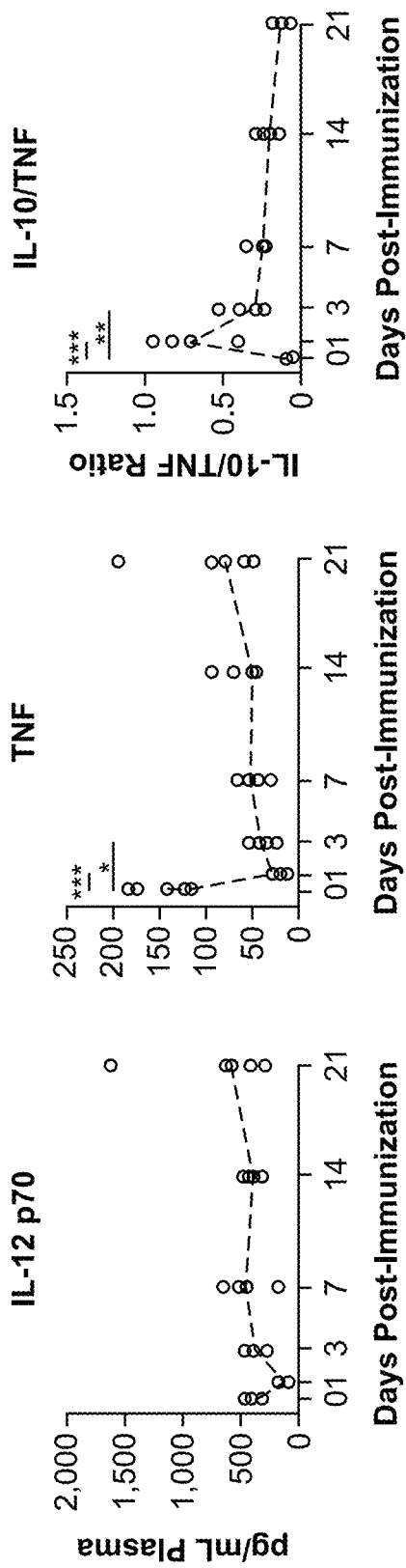
Figure 22F:
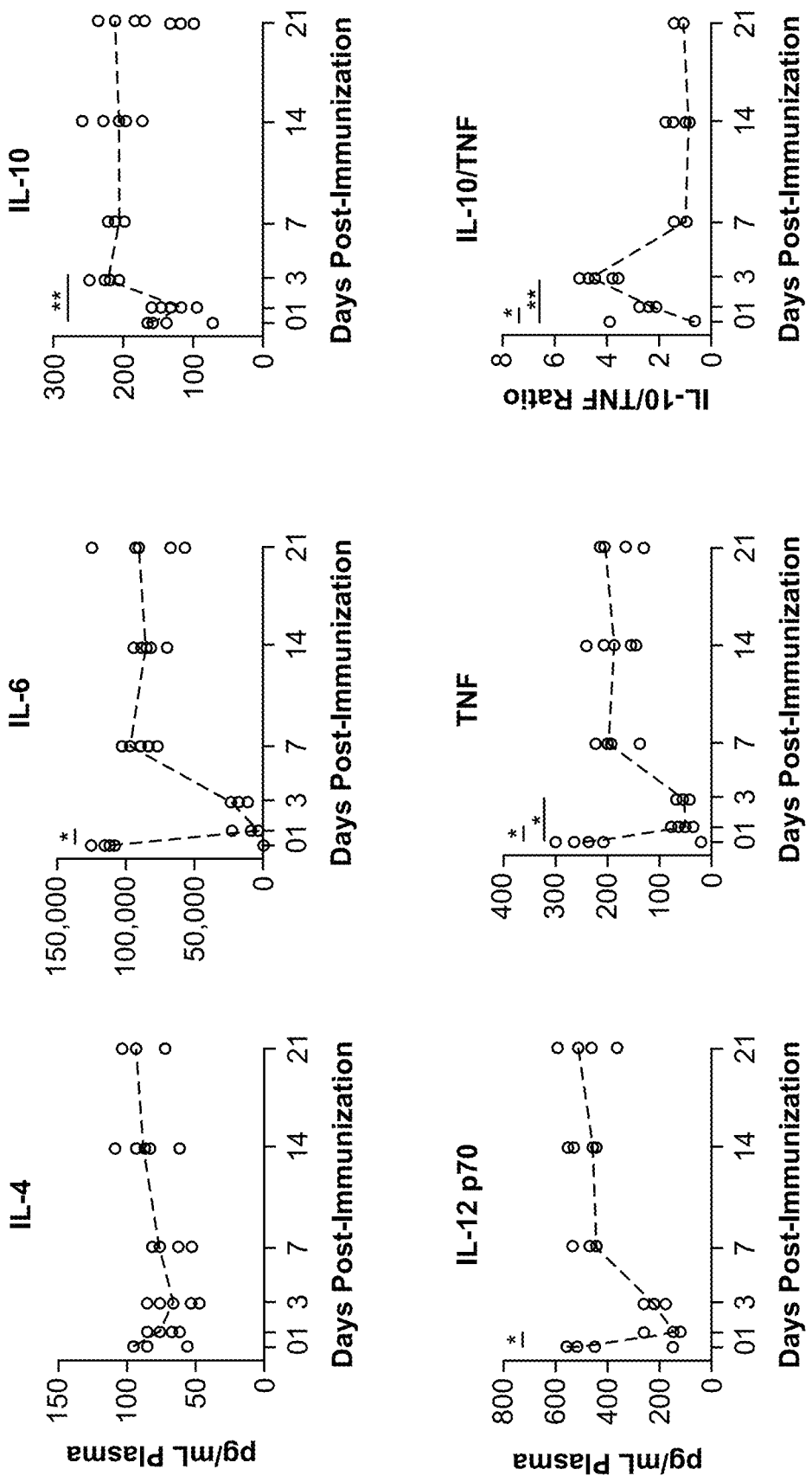

Applicant have previously observed that cytokine profiles may be a better indicator of survival outcomes than changes in bacterial burden (18-20). As such, Applicant analyzed cytokine concentrations in the plasma of the very same immunized mice challenged with lethal *S. aureus* or *A. baumannii* bacteremia at four hours post-infection. For both pathogens, immunized mice had lower concentrations of the pro-inflammatory cytokines IL-6, IL-12, and TNF; higher concentration of the anti-inflammatory cytokine IL-10; and elevated IL-10/TNF ratios that persisted even when infected weeks after immunization (FIGS. 22E-22F). This trend matched with the gene expression analysis performed in immunized mice, and it was especially pronounced in mice challenged one or three days post-immunization. Several cytokines were below the limit of detection (IFNγ, IL-1β, IL-13, IL-17A) or did not change (IL-4).

MMA Vaccination Induce Epigenetic and Gene Expression Changes

To further understand the mechanism of protection mediated by MMA and evaluate whether the vaccine induces epigenetic biomarkers of trained immunity, Applicant studied histone reprogramming and transcription changes in immunized mice. Epigenetic reprogramming has been shown to be a key characteristic of trained immunity (16, 21), with acetylation of histone 3 lysine 27 (H3K27ac) as a key marker for activation of promoters and enhancers (22). To test this, Applicant isolated splenic macrophages from mice that were immunized with MMA three or 21 days prior, and then performed H3K27ac chromatin immunoprecipitation sequencing (ChIP-seq) and RNA sequencing (RNA-seq). With mice immunized for three days, H3K27ac ChIP-seq revealed 1,080 differential peaks compared to naïve control mice and 1,039 differential peaks compared to mice immunized for 21 days (FIG. 21A). Naïve control mice and mice immunized for 21 days showed few differential peaks (FIG. 21A).

Similarly, RNA-seq identified 779 differentially expressed genes (DEGs) between naïve mice and mice immunized three days prior, 652 DEGs between mice immunized three days prior and mice immunized 21 days prior, but only 170 DEGs between naïve mice and mice immunized 21 days prior (FIG. 21B). The majority of highly acetylated H3K27 regions in mice immunized three days prior returned to baseline by 21 days post-immunization. Most regions with low H3K27 acetylation in mice immunized three days prior had increased by 21 days post-immunization, although not all returned to baseline (FIG. 21C). Similar gene-expression changes were observed by RNA-seq (FIG. 21C), indicating changes in H3K27ac resulted in gene expression in the manner we expected.

To understand the biological processes influenced by MMA immunization, Applicant conducted pathway analyses on DEGs. The analysis found that many genes highly upregulated at three days post-immunization were associated with host defense against various infections, such as those caused by *S. aureus*, *Bordetella pertussis*, *Plasmodium* spp., and prions, as well as pathways known to be related to activation of the innate immune system such as lysosome formation and the complement cascade (FIG. 21D).

Experiment 9: Vaccine Immunization Materials and Protocols

The following materials and methods relate to and support the data reporting in Experiment 8.

Mannan (Sigma, M3640), Monophosphoryl lipid A (MPL) (InvivoGen, tlrl-mpls), whole glucan particles (WGP) (InvivoGen, tlrl-wgp), and 2% aluminum hydroxide (Al(OH)$_3$) (Accurate Chemical & Scientific Corporation, A1090S) were prepared and stored according to the manufacturer's protocol. Mannan (MedicaPharma, mannan), PHAD® (Avanti Polar Lipids, 699800P), and 2% Al(OH)$_3$ (Croda, AJV3012) were used in GMP/GLP-grade MMA. Vaccine is freshly prepared each time. Mice were immunized with 200 µL administered subcutaneously (SC) in the scruff of the neck with pre-mixed vaccine in phosphate-buffered saline (PBS). Unless specificized other wise, each mice were give single or combinations of 0.1% Al(OH)$_3$, 100 µg WGP, and 10 µg MPL, and 100 µg Mannan. Mice immunized with MWA 30% were immunized with 0.1% Al(OH)$_3$, 3 µg MPL, and 30 µg WGP. Mice immunized with MWA 10% were immunized with 0.1% Al(OH)$_3$, 1 μg MPL, and 10 μg WGP. Mice immunized with or MWA 1% were immunized with 0.1% Al(OH)$_3$, 0.1 μg MPL, and 1 μg WGP.

Intravenous (IV) Infection

Frozen stocks of *A. baumannii* and *K pneumoniae* bacteria grown to mid-log phase were prepared as previously described (35). Inocula were prepared by diluting these concentrated frozen stocks of bacteria in PBS. Inocula were confirmed by plating serial dilutions on tryptic soy agar (TSA) plates and incubating overnight at 37° C. Mice infected with *A. baumannii* were monitored for seven days and mice infected with *K pneumoniae* were monitored for 14 days, after which they were euthanized according to the IACUC protocol.

*S. aureus* and *E. faecalis* inocula were prepared from mid-log phase subcultures of overnight cultures for each infection. Briefly, *S. aureus* and *E. faecalis* inoculated into tryptic soy broth (TSB) and incubated overnight at 37° C. with shaking set to 200 rpm. A subculture was set up from a 1:100 dilution of the overnight culture into sterile TSB and incubated for 3 h at 37° C. with shaking set to 200 rpm. The subculture was rinsed by pelleting in a refrigerated centrifuge at 4,000×g for 5 min and resuspending the pellet in PBS. After two more rinses (three total), the pellet was resuspended in PBS and the optical density at 600 nm (OD$_{600}$) was adjusted to 0.5 using PBS. Inocula were confirmed by plating serial dilutions on TSA plates and incubating overnight at 37° C. Mice infected with *S. aureus* were monitored for 28 days, after which they were euthanized according to the IACUC protocol. Mice infected with *E. faecalis* were monitored for seven days, after which they were euthanized according to the IACUC protocol.

101581 *Rhizopus delemar* were cultured on plates with Potato dextrose agar for 8 days at 37° C. and harvested with PBS with 0.05% TWEENT™ 80. The conidial density was determined with a hemocytometer, and the viability of conidial suspensions was determined by plating on Sabouraud's dextrose agar. Mice infected with *R. delemar* were monitored for 14 days, after which they were euthanized according to the IACUC protocol.

*Candida albicans* was serially passaged three times in yeast peptone dextrose broth and washed twice with PBS prior to infection. The infectious inoculum was prepared by counting in a hemacytometer. Mice infected with *C. albicans* were monitored for 7 days, after which they were euthanized according to the IACUC protocol.

Oral Aspiration (OA) Infection

Mice were infected using the aspiration pneumonia model as previously described (7). Briefly, inocula of *A. baumannii* and *P. aeruginosa* were prepared from subcultures of overnight cultures, as stated above, mice were infected by aspirating 50 μL of bacteria suspended in PBS. Mice infected via OA were monitored for up to seven days, after which they were euthanized according to the IACUC protocol.

Innate Immune Cell Depletion

Macrophages were depleted by injecting liposomal clodronate (Foundation Clodronate Liposomes, C-010) intraperitoneally (IP) at 50 mg/kg three days before infection (36). Neutrophils were depleted by injecting cyclophosphamide (Baxter) IP at 230 mg/kg three days before infection (18, 37).

Flow Cytometry Analysis

The spleens of mice were collected, mashed through a 70-μm cell strainer with a 35-mL syringe plunger, and rinsed with Dulbecco's modified Eagle medium (DMEM) supplemented with 10% fetal bovine serum (FBS) by volume (DMEM+10% FBS). Splenocytes were pelleted in a room-temperature centrifuge at 300×g for 5 min, and the supernatant was discarded. After three rinses with PBS, red blood cells (RBC) were lysed using RBC lysis buffer (BioLegend, 420301) according to the manufacture's protocol. Splenocytes were resuspended in PBS with 5% Fetal Bovine Serum (FACS buffer), counted with a hemacytometer, and incubated with Fc blocker (BD Biosciences, 553141) for 30 min on ice. Splenocytes were pelleted in a room-temperature centrifuge at 300×g for 5 min, resuspended in FACS buffer, and incubated with fluorophore-conjugated antibodies for OMIP-032, a two-panel, multi-color immunophenotyping assey to assess innate and adaptive immune cell populations as previously described (38). After incubation, splenocytes were pelleted in a room-temperature centrifuge at 300×g for 5 min, rinsed with PBS twice, and resuspended in FACS buffer. Samples were analyzed using a BD FACS Canto II flow cytometer.

Bacteria binding flow analysis was performed by incubating diluted HUMC1 (1: 100) or LAC (1:100,000) with mouse plasma or 10 μg/mL isotype (Fisher, MAB002) or plasma from mouse recovered from HUMC1 or LAC infection for 30 min. Bacteria were pelleted in a room-temperature centrifuge at 10,000×g for 1 min and rinsed with PBS twice. Then, samples were incubated with anti-mouse secondary antibody (Thermo Fisher, A21235) for 30 min, pelleted, rinsed with PBS twice, and resuspended in FACS buffer. Samples were analyzed using a BD Accuri™ C6 Plus flow cytometer.

In Vitro Macrophage Opsonophagocytosis Assays

Applicant used RAW 264.7 murine macrophages (ATCC) cultured with DMEM+10% FBS stimulated with either mixture of 10 ng/mL Al(OH)$_3$, 0.5 μg/mL MPL and 5 μg/mL Mannan ("MMA") for one or three days. RAW 264.7 stimulated with 100 μg/mL IFN-γ (Peprotech, 315-05) and PBS overnight were used as positive and negative controls, as previously described (39). Once cells were ready, Applicant performed macrophage opsonophagocytosis assay as follows. Bacteria were prepared from overnight cultures of *A. baumannii* subcultured to log phase, washed in PBS, and resuspended in Hanks' balanced salt solution (HBSS). Cells were rinsed three times with HBSS, bacteria were added to wells at a ratio of 20:1 (bacteria to macrophages) in the presence of 10% CD-1 mouse serum (Innovative Research Inc, IMSCD1-COMPL), and centrifuged at 300×g for 5 min. Macrophages were washed three times with HBSS, fixed with 100% methanol, and Hema-3 stained according to the manufacturer's protocol (Fisher Scientific). To quantitate bacteria per macrophage, coverslips were imaged on a Leica DMLS clinical microscope with a Leica ICC50 HD digital camera.

Ex Vivo Macrophage Opsonophagocytosis Assay

Applicant used ex vivo macrophages differentiated from human peripheral blood mononuclear cells (PBMC). Fresh PBMC were purchased from UCLA/CFAR virology core laboratory. Monocytes were isolated (StemCell Technologies, 19359) and differentiated to M1 macrophages (StemCell Technologies, 10961) according to the manufacture's protocol. We stimulated with either mixture of 10 ng/mL Al(OH)$_3$, 0.5 μg/mL MPL and 5 μg/mL Mannan for one or three days. Macrophages stimulated with 50 ng/mL IFN-γ (StemCell Technologies, 78020) and PBS three days were used as positive and negative controls. Macrophage opsonophagocytosis assay was performed and numerated as mentioned above.

Chromatin Immunoprecipitation Sequencing

Spleens were harvested from C3HeB/Fe mice and splenocytes were isolated as above. Splenocytes were rinsed in PBS and resuspended in PBS containing 2% FBS and 1 mM EDTA. Following the manufacturer's protocol (StemCell Technologies, 100-0659), f4/80+ macrophages were isolated. H3K27ac chromatin immunoprecipitation (ChIP) was performed using anti-H3K27ac polyclonal antibody (Diagenode, C15410196) and iDeal ChIP-seq kit for Histones (Diagenode, C01010051). Azenta Life Sciences performed DNA library preparation and Illumina HiSeq 150-bp paired-end sequencing. ChIP-sequencing reads were aligned to mouse genome assembly mm39 (based on NCBI GRCm39) using bwa (PMID: 19451168). BAM files were filtered to remove duplicate reads and those with poor mapping quality using SAMtools (PMID: 19505943). MACS2 was used to call H3K27ac peaks using the default (narrow) setting (PMID: 18798982). The quality of the ChIP-seq data was visualized by making bigwig files using deepTools (PMID: 27079975) in the UCSC Genome browser. For differential peak calling, data (H3K27ac reads/peak) were normalized using the R package DESeq2 (PMID: 25516281), and then pairwise comparisons were performed between the PBS, day 3 and day 21 groups. Differential peaks were identified as adjusted p value <0.05, fold change >2, reads/peak >50. Peaks were then merged into one file to generate principal component analysis (PCA) plots.

RNA Sequencing

Splenic f4/80+macrophages were harvested from C3HeB/Fe mice as mentioned above. Azenta Life Sciences performed RNA isolation, rRNA depletion, library preparation, and Illumina HiSeq 150-bp paired-end sequencing. To infer gene expression levels, RNA-seq reads were aligned to mm39 mouse transcriptome using Bowtie (PMID: 19261174). Quantification of gene expression was performed using MMSEQ (PMID: 21310039). Statistical analysis was performed using DESeq2, with pairwise comparisons performed between the PBS, day 3 and day 21 groups. Differentially expressed genes were identified as those showing p value <0.05, FC >2 and RPKM >1. Differential gene lists from all comparisons were then merged, and the combined list of differential genes was used for plotting Statistics Survival was compared by the non-parametric log-rank test with $\alpha=0.05$. Bacterial burden, cell population, macrophage assay, and cytokine were compared by Wilcoxon-Mann-Whitney test or Kruskal-Wallis test with $\alpha=0.05$.

TABLE 3

Immunization did not result in pathogen specific antibodies production. Male C3HeB/Fe and female BALB/c mice (N = 5 per group) immunized with MMA did not develop antibodies specific to *S. aureus* or *A. baumannii*.

| | Median Binding | |
|---|---|---|
| | S. aureus | A. baumannii |
| Mouse IgG$_1$ | 1% | 0% |
| Naïve | 1% | 0% |
| Day 1 | 1% | 0% |
| Day 3 | 1% | 0% |
| Day 7 | 1% | 0% |
| Day 14 | 1% | 0% |
| Day 21 | 1% | 0% |
| Immune Plasma | 57% | 94% |

DISCUSSION

Applicant discovered that a protein-free, tripartite vaccine mediated cross-kingdom protection against high priority, AMR bacterial and fungal bloodstream and lung infections in mice, including in CD34$^+$ humanized mice. Protection started within 24 hours after vaccination, lasted up to three weeks, and protection was mediated by the innate rather than the adaptive immune system. Protection required macrophages, but not lymphocytes or neutrophils. NK cells were required for optimal protection against *S. aureus* infection, but not for the Gram-negative pathogen, *A. baumannii*. Furthermore, vaccination significantly increased the number of monocytes and macrophages in the blood, and the vaccine directly induced monocyte to macrophage differentiation, and markedly enhanced phagocytosis, in in vitro and ex vivo. Macrophages were shown to mediate protection in a manner that involved cytokine modulation via epigenetic reprogramming. Applicant also demonstrated that the tripartite vaccine induced H3K27ac epigenetic changes and gene expression changes in splenic macrophages. Collectively, these data confirm that the mechanism of protection of the vaccine was induction of trained immunity (23).

Traditional vaccines are "vertical" infection prevention approaches (4), which activate antigen-specific lymphocytes that target one pathogen at a time. This single-pathogen targeting makes such vaccines difficult to develop or deploy for the prevention of HAIs, which are caused by myriad bacterial and fungal pathogens. In contrast, trained immunity offers a much broader targeting of pathogens and is reflective of a "horizontal" infection prevention approach, rather than being pathogen specific. The cost of the horizontal targeting of many pathogens from one vaccine via trained immunity is that protection lasts for a much shorter period of time than it does for adaptive immune-mediated traditional, pathogen-specific vaccines. However, given that the average duration of acute care hospitalization is 5 days, and 95% of hospitalizations last less than 21 days (31), the shorter duration of protection offered by trained immunity is not a detriment to vaccine efficacy or deployment.

The global crisis of AMR infections continues to expand, while the pipeline of new antibiotics to combat the threat cannot keep pace (32). This study utilized models for two common routes of infections caused by AMR nosocomial pathogens: central line-associated bloodstream infections and ventilator-associated pneumonia (33). Many such infections are extremely drug-resistant with few effective prevention or treatment options. The most AMR pathogens are found in hospitals, and new strategies are critically needed to prevent such infections (34). Described herein is a novel, trained immunity vaccine that can be used to prevent blood and lung infections caused by the most dangerous, highest priority, AMR pathogens that cause HAIs. The wide breadth and robustness of protection offered by our vaccine against these infections suggests it carries substantial promise to reduce antimicrobial usage and revolutionize infection prevention in healthcare.

EQUIVALENTS

It is to be understood that while the disclosure has been described in conjunction with the above embodiments, that the foregoing description and examples are intended to illustrate and not limit the scope of the disclosure. Other aspects, advantages and modifications within the scope of the disclosure will be apparent to those skilled in the art to which the disclosure pertains.

The inventions illustratively described herein may suitably be practiced in the absence of any element or elements, limitation or limitations, not specifically disclosed herein. Thus, for example, the terms "comprising", "including," "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed.

Thus, it should be understood that although the present invention has been specifically disclosed by preferred embodiments and optional features, modification, improvement and variation of the inventions embodied therein herein disclosed may be resorted to by those skilled in the art, and that such modifications, improvements and variations are considered to be within the scope of this invention. The materials, methods, and examples provided here are representative of preferred embodiments, are exemplary, and are not intended as limitations on the scope of the invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

In addition, where features or aspects of the invention are described in terms of Markush groups, those skilled in the art will recognize that the invention is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

References—Experiments 1 to 7
1. W. H. Organization.
2. S. S. Magill et al., Multistate point-prevalence survey of health care-associated infections. *N Engl J Med* 370, 1198-1208 (2014).
3. A. Marchetti, R. Rossiter, Economic burden of healthcare-associated infection in US acute care hospitals: societal perspective. *J Med Econ* 16, 1399-1404 (2013).
4. L. M. Weiner et al., *Antimicrobial-Resistant Pathogens Associated With Healthcare-Associated Infections: Summary of Data Reported to the National Healthcare Safety Network at the Centers for Disease Control and Prevention, 2011-2014. Infect Control Hosp Epidemiol* 37, 1288-1301 (2016).
5. R. P. Wenzel, M. B. Edmond, Infection control: the case for horizontal rather than vertical interventional programs. *Int J Infect Dis* 14 Suppl 4, S3-5 (2010).
6. E. Septimus, R. A. Weinstein, T. M. Perl, D. A. Goldmann, D. S. Yokoe, Approaches for preventing healthcare-associated infections: go long or go wide? *Infect Control Hosp Epidemiol* 35, 797-801 (2014).
7. Baylor NW, Egan W, Richman P. Aluminum salts in vaccines—US perspective. Vaccine 2002;20 Suppl 3:S18-23.
8. B. M. Luna et al., Vaccines targeting *Staphylococcus aureus* skin and bloodstream infections require different composition. *PLoS One* 14, e0217439 (2019).
9. T. B. Nielsen, J. Yan, B. Luna, B. Spellberg, Murine Oropharyngeal Aspiration Model of Ventilator-associated and Hospital-acquired Bacterial Pneumonia. Journal of visualized experiments: JoVE, (2018).
10. B. Spellberg et al., The antifungal vaccine derived from the recombinant N terminus of Als3p protects mice against the bacterium *Staphylococcus aureus*. *Infect Immun* 76, 4574-4580 (2008).
11. P. Mombaerts et al., RAG-1-deficient mice have no mature B and T lymphocytes. *Cell* 68, 869-877 (1992).
12. M. G. Netea, J. Quintin, J. W. van der Meer, Trained immunity: a memory for innate host defense. Cell Host Microbe 9, 355-361 (2011).
13. E. Kaufmann et al., BCG Educates Hematopoietic Stem Cells to Generate Protective Innate Immunity against Tuberculosis. *Cell* 172, 176-190.e119 (2018).
14. T. B. Nielsen et al., Monoclonal antibody requires immunomodulation for efficacy against *Acinetobacter baumannii* infection. *J Infect Dis*, (2021).
15. T. B. Nielsen, K. W. Bruhn, P. Pantapalangkoor, J. L. Junus, B. Spellberg, Cryopreservation of virulent *Acinetobacter baumannii* to reduce variability of in vivo studies. *BMC Microbiol* 15, 252 (2015).
16. H. H. Mostafa, P. Vogel, A. Srinivasan, C. J. Russell, Non-invasive Imaging of Sendai Virus Infection in Pharmacologically Immunocompromised Mice: NK and T Cells, but not Neutrophils, Promote Viral Clearance after Therapy with Cyclophosphamide and Dexamethasone. *PLoS Pathog* 12, e1005875 (2016).
17. J. P. Bottcher et al., NK Cells Stimulate Recruitment of cDC1 into the Tumor Microenvironment Promoting Cancer Immune Control. *Cell* 172, 1022-1037.e1014 (2018).
18. A. Unsworth, R. Anderson, N. Haynes, K. Britt, OMIP-032: Two multi-color immunophenotyping panels for assessing the innate and adaptive immune cells in the mouse mammary gland. Cytometry A 89, 527-530 (2016).

References for Experiment Nos. 8 and 9:
1. A. Marchetti, R. Rossiter, Economic burden of healthcare-associated infection in US acute care hospitals: societal perspective. *J Med Econ* 16, 1399-1404 (2013).
2. S. S. Magill et al., Multistate point-prevalence survey of health care-associated infections. *N Engl J Med* 370, 1198-1208 (2014).
3. L. M. Weiner et al., *Antimicrobial-Resistant Pathogens Associated With Healthcare-Associated Infections: Summary of Data Reported to the National Healthcare Safety Network at the Centers for Disease Control and Prevention, 2011-2014. Infection control and hospital epidemiology: the official journal of the Society of Hospital Epidemiologists of America* 37, 1288-1301 (2016).
4. R. P. Wenzel, M. B. Edmond, Infection control: the case for horizontal rather than vertical interventional programs. International journal of infectious diseases: IJID: official publication of the International Society for Infectious Diseases 14 Suppl 4, S3-5 (2010).
5. E. Septimus, R. A. Weinstein, T. M. Perl, D. A. Goldmann, D. S. Yokoe, Approaches for preventing healthcare-associated infections: go long or go wide? *Infect Control Hosp Epidemiol* 35, 797-801 (2014).
6. B. M. Luna et al., Vaccines targeting *Staphylococcus aureus* skin and bloodstream infections require different composition. *PLoS One* 14, e0217439 (2019).
7. T. B. Nielsen, J. Yan, B. Luna, B. Spellberg, Murine Oropharyngeal Aspiration Model of Ventilator-associated and Hospital-acquired Bacterial Pneumonia. Journal of visualized experiments: JoVE, (2018).

8. B. Spellberg et al., The antifungal vaccine derived from the recombinant N terminus of Als3p protects mice against the bacterium *Staphylococcus aureus. Infect Immun* 76, 4574-4580 (2008).
9. F. Ishikawa et al., Development of functional human blood and immune systems in NOD/SCID/IL2 receptor {gamma} chain(null) mice. Blood 106, 1565-1573 (2005).
10. A. M. Coughlan et al., Myeloid Engraftment in Humanized Mice: Impact of Granulocyte-Colony Stimulating Factor Treatment and Transgenic Mouse Strain. *Stem Cells Dev* 25, 530-541 (2016).
11. P. Mombaerts et al., RAG-1-deficient mice have no mature B and T lymphocytes. *Cell* 68, 869-877 (1992).
12. J. G. Noordzij et al., The immunophenotypic and immunogenotypic B-cell differentiation arrest in bone marrow of RAG-deficient SCID patients corresponds to residual recombination activities of mutated RAG proteins. *Blood* 100, 2145-2152 (2002).
13. Y. Shinkai et al., RAG-2-deficient mice lack mature lymphocytes owing to inability to initiate V(D)J rearrangement. *Cell* 68, 855-867 (1992).
14. W. G. Glass, K. Subbarao, B. Murphy, P. M. Murphy, Mechanisms of host defense following severe acute respiratory syndrome-coronavirus (SARS-CoV) pulmonary infection of mice. *J Immunol* 173, 4030-4039 (2004).
15. J. G. O'Leary, M. Goodarzi, D. L. Drayton, U. H. von Andrian, T cell- and B cell-independent adaptive immunity mediated by natural killer cells. *Nat Immunol* 7, 507-516 (2006).
16. S. Saeed et al., Epigenetic programming of monocyte-to-macrophage differentiation and trained innate immunity. *Science* 345, 1251086 (2014).
17. C. Covian et al., BCG-Induced Cross-Protection and Development of Trained Immunity: Implication for Vaccine Design. *Front Immunol* 10, 2806 (2019).
18. T. B. Nielsen et al., Monoclonal antibody requires immunomodulation for efficacy against *Acinetobacter baumannii* infection. *J Infect Dis*, (2021).
19. L. A. Pirofski, A. Casadevall, The damage-response framework of microbial pathogenesis and infectious diseases. *Adv Exp Med Biol* 635, 135-146 (2008).
20. P. L. Fidel, Jr., J. Yano, S. K. Esher, M. C. Noverr, Applying the Host-Microbe Damage Response Framework to *Candida* Pathogenesis: Current and Prospective Strategies to Reduce Damage. J Fungi (Basel) 6, (2020).
21. B. de Laval et al., C/EBPβ-Dependent Epigenetic Memory Induces Trained Immunity in Hematopoietic Stem Cells. *Cell Stem Cell* 26, 657-674.e658 (2020).
22. A. Rada-Iglesias et al., A unique chromatin signature uncovers early developmental enhancers in humans. *Nature* 470, 279-283 (2011).
23. M. G. Netea, J. Quintin, J. W. van der Meer, Trained immunity: a memory for innate host defense. Cell Host Microbe 9, 355-361 (2011).
24. E. Kaufmann et al., BCG Educates Hematopoietic Stem Cells to Generate Protective Innate Immunity against Tuberculosis. *Cell* 172, 176-190.e119 (2018).
25. M. G. Daskalaki, C. Tsatsanis, S. C. Kampranis, Histone methylation and acetylation in macrophages as a mechanism for regulation of inflammatory responses. *J Cell Physiol* 233, 6495-6507 (2018).
26. J. J. Seeley et al., Induction of innate immune memory via microRNA targeting of chromatin remodelling factors. *Nature* 559, 114-119 (2018).
27. E. J. Giamarellos-Bourboulis et al., Activate: Randomized Clinical Trial of BCG Vaccination against Infection in the Elderly. *Cell* 183, 315-323.e319 (2020).
28. S. Sanchez-Ramon et al., Trained Immunity-Based Vaccines: A New Paradigm for the Development of Broad-Spectrum Anti-infectious Formulations. *Front Immunol* 9, 2936 (2018).
29. E. Ciarlo et al., Trained Immunity Confers Broad-Spectrum Protection Against Bacterial Infections. *J Infect Dis* 222, 1869-1881 (2020).
30. L. Martin-Cruz et al., A Combination of Polybacterial MV140 and *Candida albicans* V132 as a Potential Novel Trained Immunity-Based Vaccine for Genitourinary Tract Infections. *Front Immunol* 11, 612269 (2020).
31. H. Baek et al., Analysis of length of hospital stay using electronic health records: A statistical and data mining approach. *PLoS One* 13, e0195901 (2018).
32. J. A. Al-Tawfiq et al., Antibiotics in the pipeline: a literature review (2017-2020). Infection 50, 553-564 (2022).
33. A. Sikora, F. Zahra, in StatPearls. (StatPearls Publishing Copyright (c) 2022, StatPearls Publishing LLC., Treasure Island (FL), 2022).
34. B. Spellberg, J. G. Bartlett, D. N. Gilbert, The future of antibiotics and resistance. *N Engl J Med* 368, 299-302 (2013).
35. T. B. Nielsen, K. W. Bruhn, P. Pantapalangkoor, J. L. Junus, B. Spellberg, Cryopreservation of virulent *Acinetobacter baumannii* to reduce variability of in vivo studies. *BMC Microbiol* 15, 252 (2015).
36. K. W. Bruhn et al., Host Fate is Rapidly Determined by Innate Effector-Microbial Interactions During *Acinetobacter baumannii* Bacteremia. *J Infect Dis* 211, 1296 1305 (2015).
37. H. H. Mostafa, P. Vogel, A. Srinivasan, C. J. Russell, Non-invasive Imaging of Sendai Virus Infection in Pharmacologically Immunocompromised Mice: NK and T Cells, but not Neutrophils, Promote Viral Clearance after Therapy with Cyclophosphamide and Dexamethasone. *PLoS Pathog* 12, e1005875 (2016).
38. A. Unsworth, R. Anderson, N. Haynes, K. Britt, OMIP-032: Two multi-color immunophenotyping panels for assessing the innate and adaptive immune cells in the mouse mammary gland. Cytometry A 89, 527-530 (2016).
39. B. Baquir et al., Macrophage killing of bacterial and fungal pathogens is not inhibited by intense intracellular accumulation of the lipoglycopeptide antibiotic oritavancin. *Clin Infect Dis* 54 Suppl 3, S229-232 (2012).

What is claimed is:

1. A method of enhancing innate immunity against an infection caused by a bacterial pathogen or a fungal pathogen in a mammalian subject in need thereof, the method comprising administering to the subject an effective amount of a combination
immunostimulatory composition comprising an effective amount of each of monophosphoryl lipid A (MPL), mannan, and aluminum hydroxide, with the proviso that the composition does not comprise whole glucan particles (WGP) and an antigen that is effective to induce an immune response against the bacterial pathogen or the fungal pathogen.

2. The method of claim 1, wherein the bacterial pathogen is *Staphylococcus aureus, Acinetobacter baumannii, Klebsiella pneumoniae, Pseudomonas aeruginosa*, and *Enterococcus faecalis*, and wherein the fungal pathogen is *Candida albicans* or *Rhizopus delemar*.

3. The method of claim 1, wherein the composition is administered by inhalation, intramuscular, subcutaneous, or intravenous administration.

4. The method of claim 1, wherein the composition is administered once, twice, or three times over a period of one to three months.

5. The method of claim 1, wherein the mammalian subject is at risk of the infection caused by the bacterial pathogen or the fungal pathogen, or wherein the subject is infected with the bacterial pathogen or the fungal pathogen.

6. The method of claim 1, further comprising assaying a sample from the mammalian subject for infection with the bacterial pathogen or the fungal pathogen.

7. The method of claim 1, wherein the immune response is an adaptive immune response mediated by T-cell and/or B-cell lymphocytes against the bacterial pathogen or the fungal pathogen.

8. The method of claim 1, wherein the effective amount of each of the aluminum hydroxide, the MPL, and the mannan is collectively effective to enhance the innate immunity to the bacterial pathogen or to the fungal pathogen in the mammalian subject.

9. The method of claim 1, wherein the antigen is selected from a peptide, a protein, or a glycoprotein.

10. The method of claim 1, wherein the aluminum hydroxide is an aluminum hydroxide wet suspension, optionally a 2% aluminum hydroxide wet suspension, or a 1% aluminum hydroxide wet suspension.

11. The method of claim 1, wherein the effective amount comprises:

(a) from about 0.1 mg/ml to about 10 mg/ml of the aluminum hydroxide;
(b) from about 0.1 mg/ml to about 10 mg/ml of the MPL; and
(c) from about 0.1 mg/ml to about 10 mg/ml of the mannan.

12. The method of claim 1, further comprising a pharmaceutically acceptable carrier, optionally saline or phosphate buffered saline.

13. The method of claim 1, wherein the effective amount of each of the aluminum hydroxide, the MPL, and the mannan collectively does not induce antibodies specific to the bacterial pathogen or to the fungal pathogen in the subject.

14. The method of claim 1, wherein the mammalian subject is immunocompromised or neutropenic.

15. A method of enhancing innate immunity against an infection caused by a bacterial pathogen or a fungal pathogen in a mammalian subject in need thereof, the method comprising administering to the subject an effective amount of a combination immunostimulatory composition consisting essentially of an effective amount of each of monophosphoryl lipid A (MPL), mannan, and aluminum hydroxide, with the proviso that the composition does not comprise whole glucan particles (WGP) and an antigen that is effective to induce an immune response against the bacterial pathogen or the fungal pathogen.

* * * * *

UNITED STATES PATENT AND TRADEMARK OFFICE
CERTIFICATE OF CORRECTION

PATENT NO. : 11,957,750 B2
APPLICATION NO. : 18/213127
DATED : April 16, 2024
INVENTOR(S) : Brad Spellberg et al.

Page 1 of 1

It is certified that error appears in the above-identified patent and that said Letters Patent is hereby corrected as shown below:

In the Specification

In Column 1, Lines 17-20, please delete "This invention was made with government support under Grant Nos. AI145759, AI130060, AI106375, and AI139052, awarded by the National Institutes of Health (NIH). The government has certain rights in the invention." and insert -- This invention was made with government support under Grant Nos. AI139052 and AI145759, awarded by the National Institutes of Health (NIH). The government has certain rights in the invention. --

Signed and Sealed this
Twenty-first Day of January, 2025

Coke Morgan Stewart
*Acting Director of the United States Patent and Trademark Office*